US010364282B2

(12) United States Patent
Mahr et al.

(10) Patent No.: US 10,364,282 B2
(45) Date of Patent: Jul. 30, 2019

(54) PEPTIDES AND COMBINATION OF PEPTIDES FOR USE IN IMMUNOTHERAPY AGAINST ESOPHAGEAL CANCER AND OTHER CANCERS

(71) Applicant: Immatics Biotechnologies GmbH, Tuebingen (DE)

(72) Inventors: Andrea Mahr, Tuebingen (DE); Toni Weinschenk, Aichwald (DE); Colette Song, Ostfildern (DE); Oliver Schoor, Tuebingen (DE); Jens Fritsche, Dusslingen (DE); Harpreet Singh, Munich (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 16/281,155

(22) Filed: Feb. 21, 2019

(65) Prior Publication Data
US 2019/0177397 A1    Jun. 13, 2019

Related U.S. Application Data

(63) Continuation of application No. 16/137,489, filed on Sep. 20, 2018, which is a continuation of application No. 15/965,305, filed on Apr. 27, 2018, which is a continuation of application No. 15/202,388, filed on Jul. 5, 2016, now Pat. No. 10,011,645.

(60) Provisional application No. 62/188,870, filed on Jul. 6, 2015.

(30) Foreign Application Priority Data

Jul. 6, 2015  (GB) .................. 1511792.2

(51) Int. Cl.
| | | |
|---|---|---|
| *A61K 39/00* | (2006.01) | |
| *C07K 14/74* | (2006.01) | |
| *C07K 14/635* | (2006.01) | |
| *C07K 14/47* | (2006.01) | |
| *C07K 16/28* | (2006.01) | |
| *C07K 14/725* | (2006.01) | |
| *C12N 5/0783* | (2010.01) | |
| *C12Q 1/6886* | (2018.01) | |
| *G01N 33/574* | (2006.01) | |
| *A61K 38/00* | (2006.01) | |

(52) U.S. Cl.
CPC .... *C07K 14/70539* (2013.01); *A61K 39/0011* (2013.01); *C07K 14/4748* (2013.01); *C07K 14/635* (2013.01); *C07K 14/7051* (2013.01); *C07K 16/2833* (2013.01); *C12N 5/0638* (2013.01); *C12Q 1/6886* (2013.01); *G01N 33/57484* (2013.01); *A61K 38/00* (2013.01); *A61K 39/00* (2013.01); *C07K 2319/70* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 2004/0220094 A1 | 11/2004 | Skinner |
| 2005/0033023 A1 | 2/2005 | Correale et al. |
| 2009/0274714 A1 | 11/2009 | Singh et al. |
| 2013/0096016 A1 | 4/2013 | Weinschenk et al. |
| 2013/0177525 A1 | 7/2013 | Singh et al. |

FOREIGN PATENT DOCUMENTS

| | | |
|---|---|---|
| EP | 1760089 A1 | 3/2007 |
| WO | 2007028573 A1 | 3/2007 |
| WO | 2008/013934 A2 | 1/2008 |
| WO | 2011151403 A1 | 12/2011 |

OTHER PUBLICATIONS

Great Britain Search Report dated Apr. 21, 2016 in counterpart Great Britain Application No. GB1511792.2.
Walter S. et al., "Multipeptide immune response to cancer vaccine IMA901 after single dose cyclophosphamide associates with longer patient survival" Natural Medicine, (2012) vol. 18: 1254-1261.
PCT International Search Report for PCT/EP2016/065812, dated Jan. 10, 2017.
Rizzolo, et al., "Conventional and microwave-assisted SPPS approach: a comparative synthesis of PTHrP(I-34) NH2," J. Peptide Science, (2011), vol. 17, No. 10: 708-714.
Kiessling, et al., "Tumor-Associated Antigens for Specific Immunotherapy of Prostate Cancer," Cancers, (2012), vol. 4, No. 4: 193-217.

*Primary Examiner* — Lei Yao
(74) *Attorney, Agent, or Firm* — McBee Moore Woodward & Vanik IP, LLC

(57) ABSTRACT

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

20 Claims, 29 Drawing Sheets
(12 of 29 Drawing Sheet(s) Filed in Color)
Specification includes a Sequence Listing.

Peptide: STYGGGLSV (A*02)
SEQ ID NO: 1

Figure 1B

Peptide: SIFEGLLSGV (A*02)
SEQ ID NO: 7

Relative Presentation [Arbitrary Units]

238 normal tissues: 1 adipose tissues, 3 adrenal glands, 8 arteries, 5 bone marrows, 7 brains, 5 breasts, 2 cartilages, 1 central nerve, 13 colons, 1 duodenum, 2 gallbladders, 5 hearts, 14 kidneys, 21 livers, 44 lungs, 4 lymph nodes, 4 leukocyte samples, 2 ovaries, 7 pancreas, 4 peripheral nerves, 1 peritoneum, 3 pituitary glands, 4 placentas, 3 pleuras, 3 prostates, 6 recti, 7 salivary glands, 4 skeletal muscles, 6 skins, 2 small intestines, 4 spleens, 5 stomachs, 6 testis, 3 thymi, 3 thyroid glands, 6 tracheas, 2 ureters, 6 urinary bladders, 2 uteri, 2 veins, 7 esophagi 16 Esoph. cancer tissues

Figure 1C

Peptide: SLVSEQLEPA (A*02)
SEQ ID NO: 34

Relative Presentation [Arbitrary Units]

238 normal tissues
1 adipose tissues, 3 adrenal glands, 8 arteries, 5 bone marrows, 7 brains, 5 breasts, 2 cartilages, 1 central nerve, 13 colons, 1 duodenum, 2 gallbladders, 5 hearts, 14 kidneys, 21 livers, 44 lungs, 4 lymph nodes, 4 leukocyte samples, 2 ovaries, 7 pancreas, 4 peripheral nerves, 1 peritoneum, 3 pituitary glands, 4 placentas, 3 pleuras, 3 prostates, 6 recti, 7 salivary glands, 4 skeletal muscles, 6 skins, 2 small intestines, 4 spleens, 5 stomachs, 6 testis, 3 thymi, 3 thyroid glands, 6 tracheas, 2 ureters, 6 urinary bladders, 2 uteri, 2 veins, 7 esophagi 16 Esoph. cancer tissues

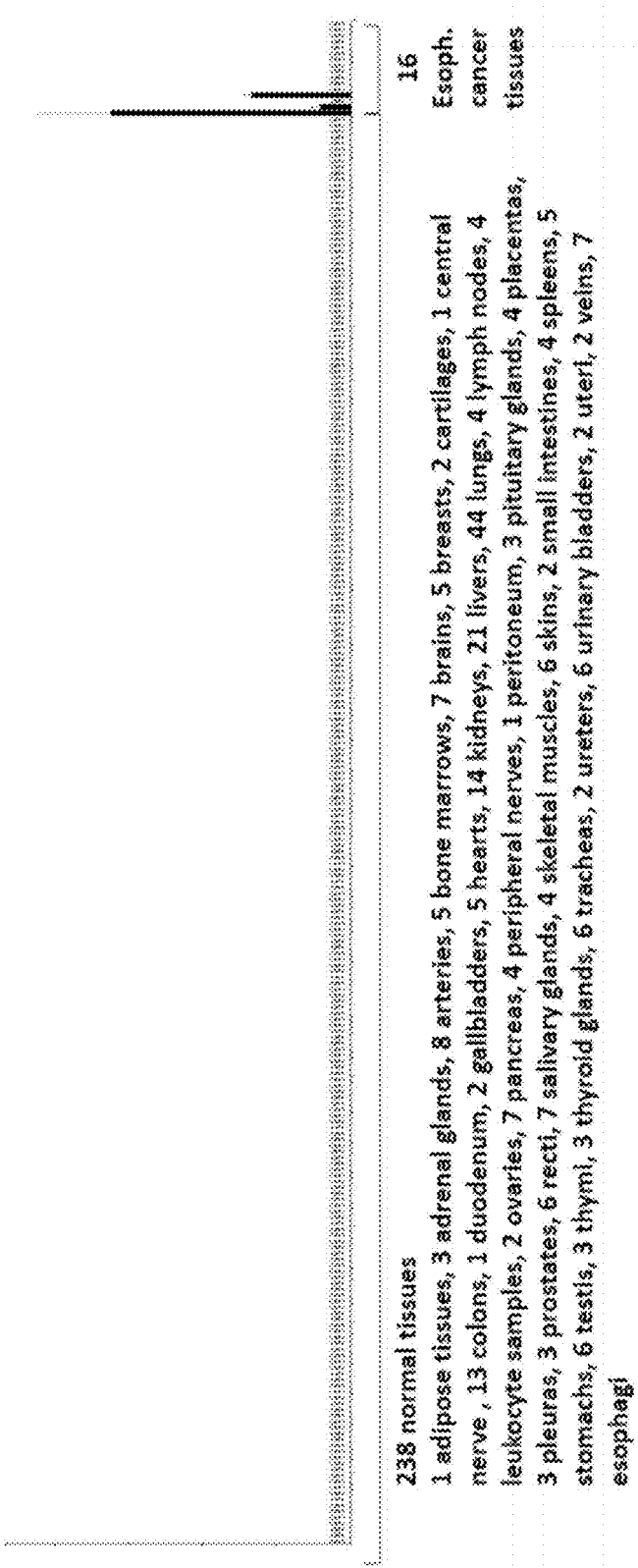

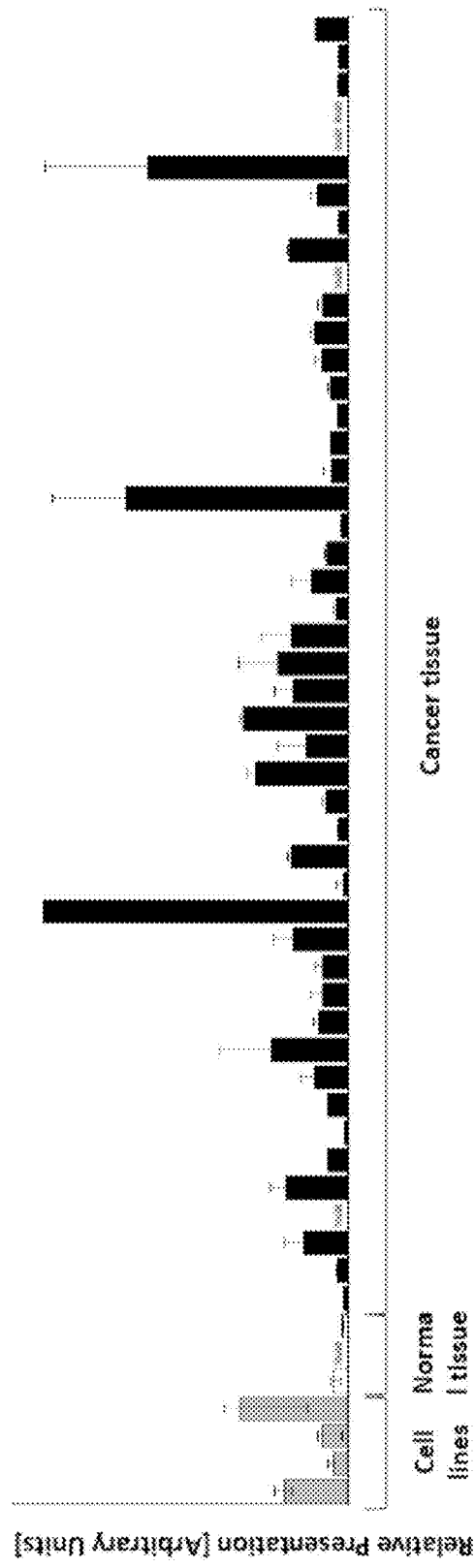

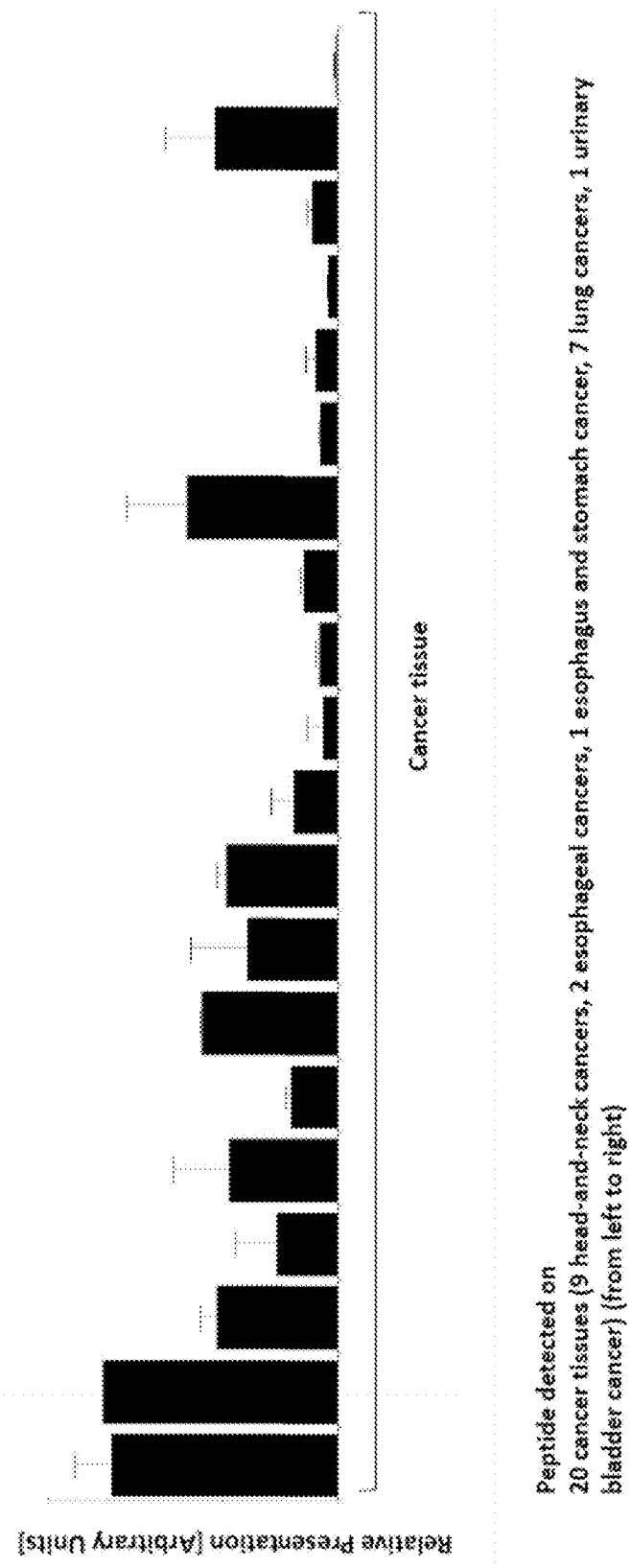

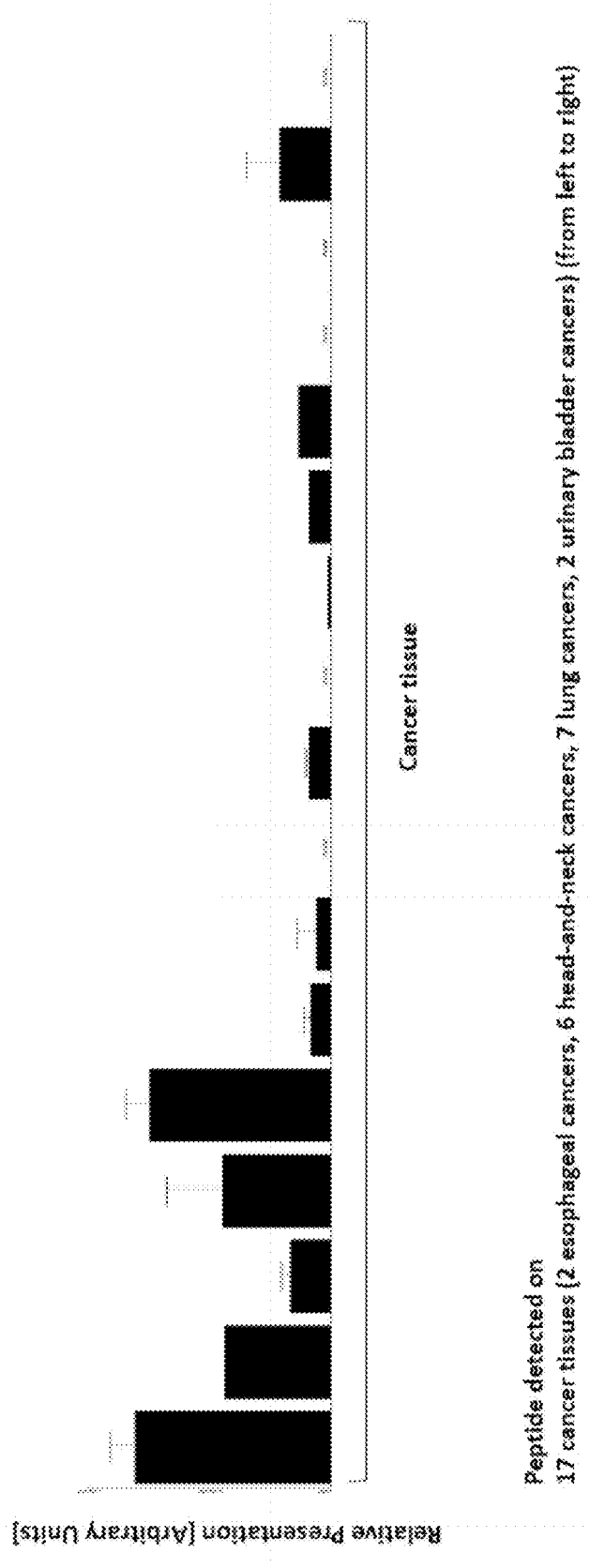

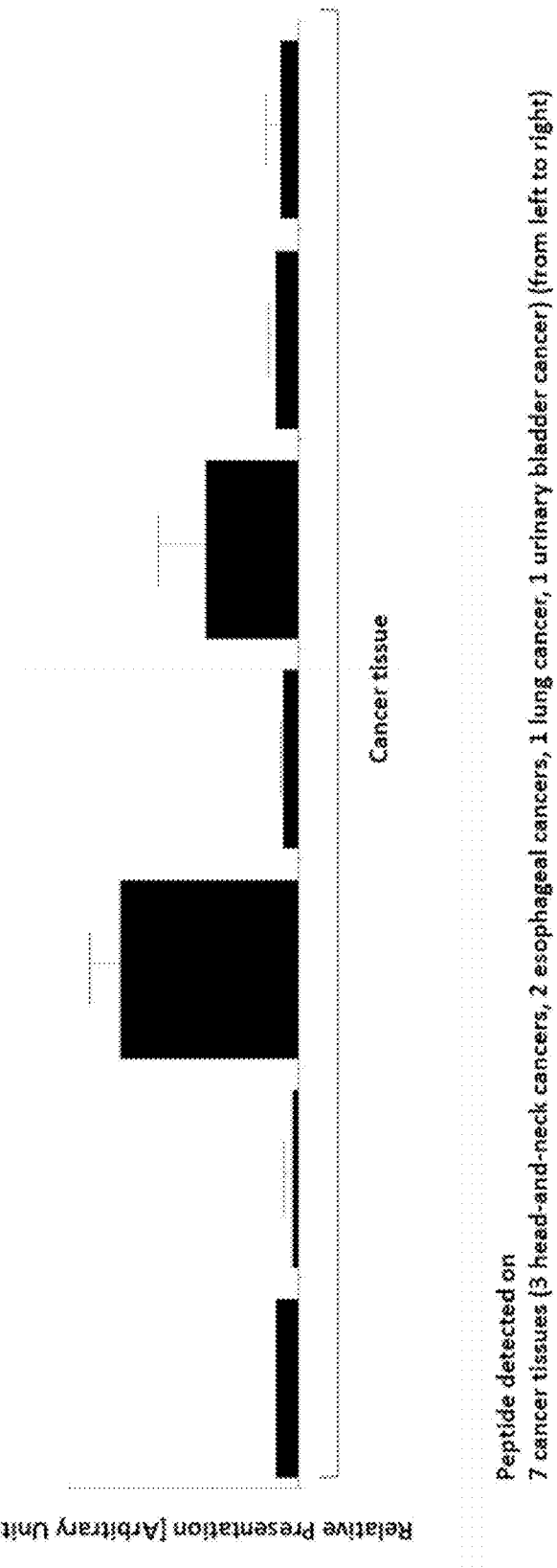

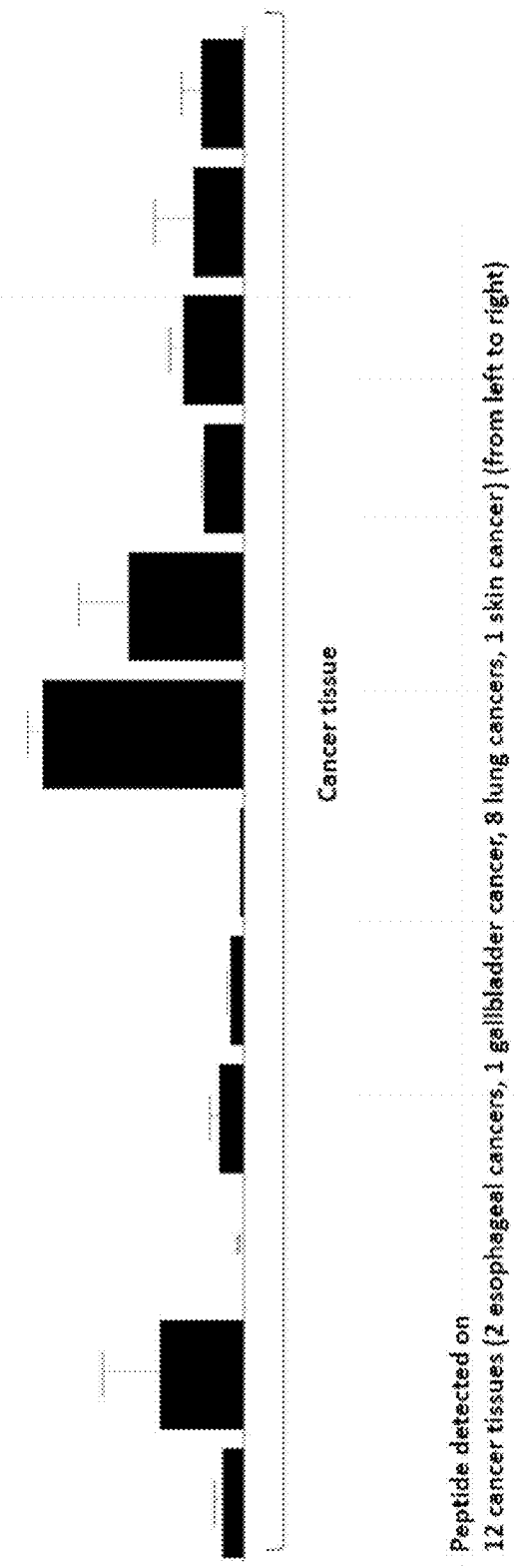

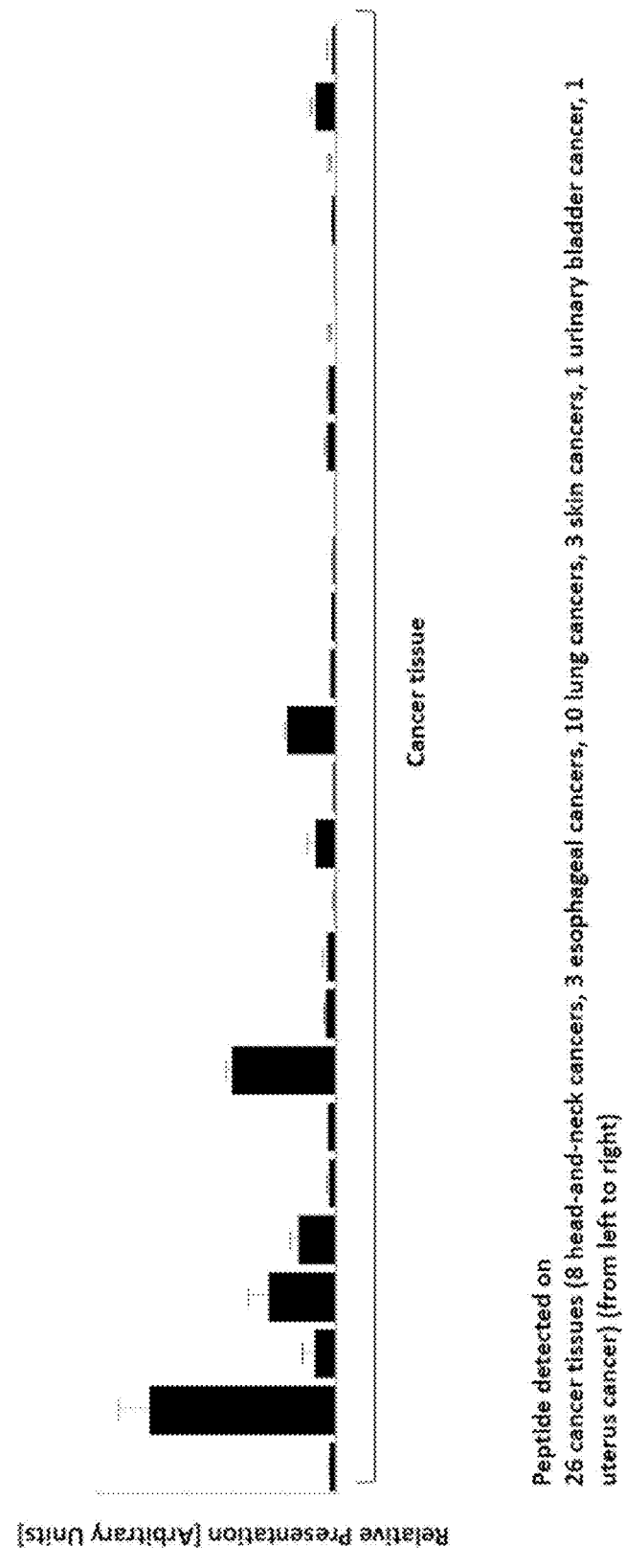

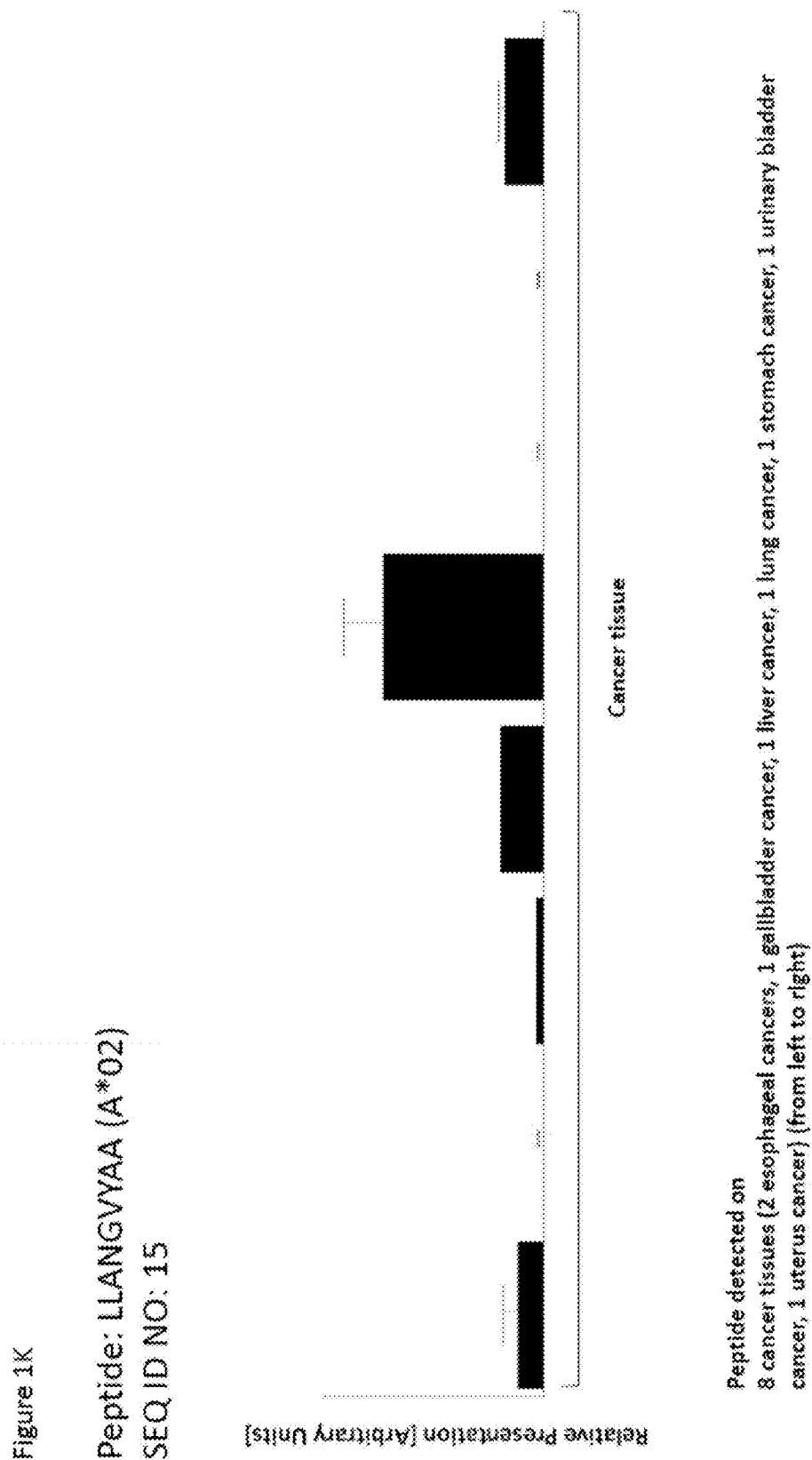

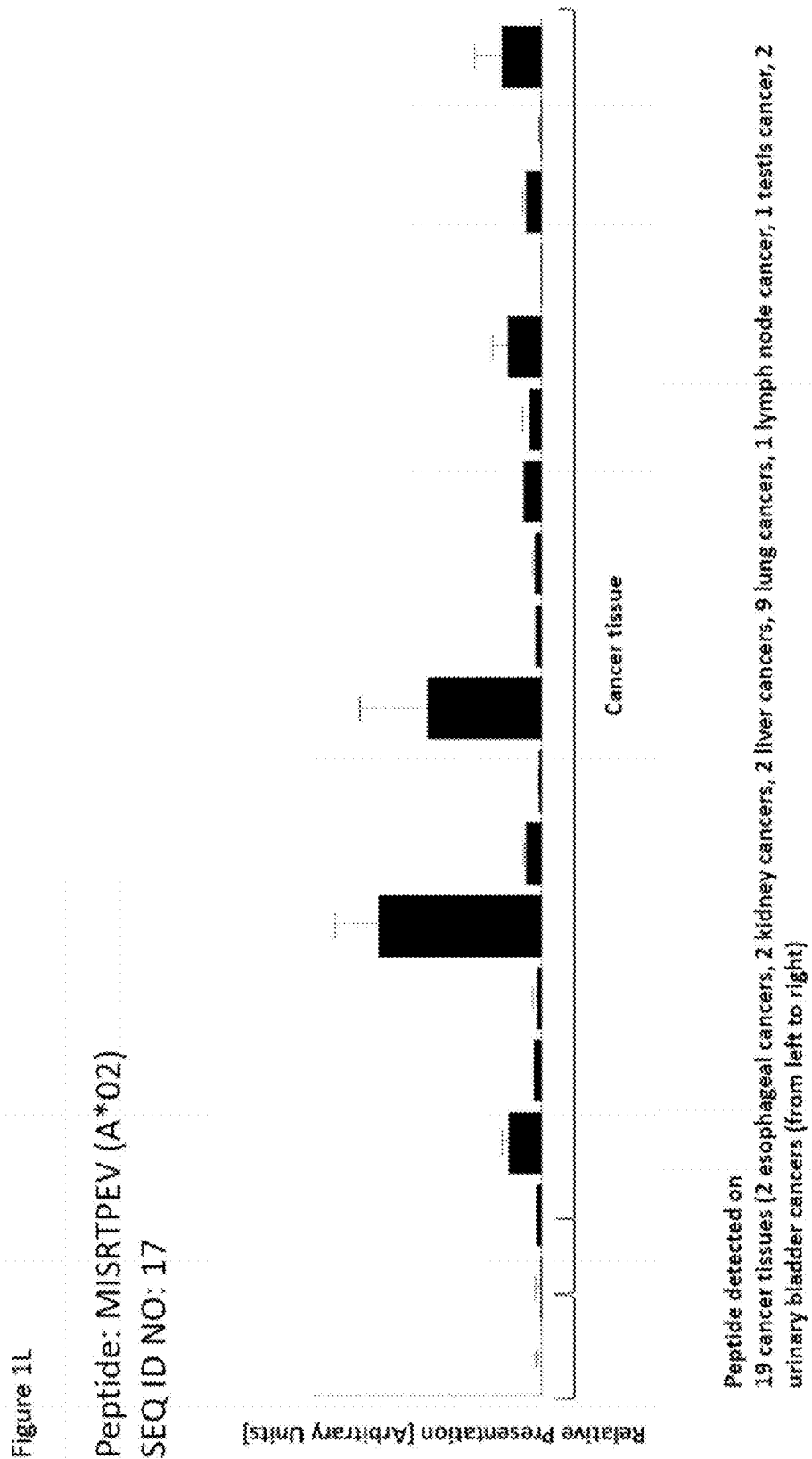

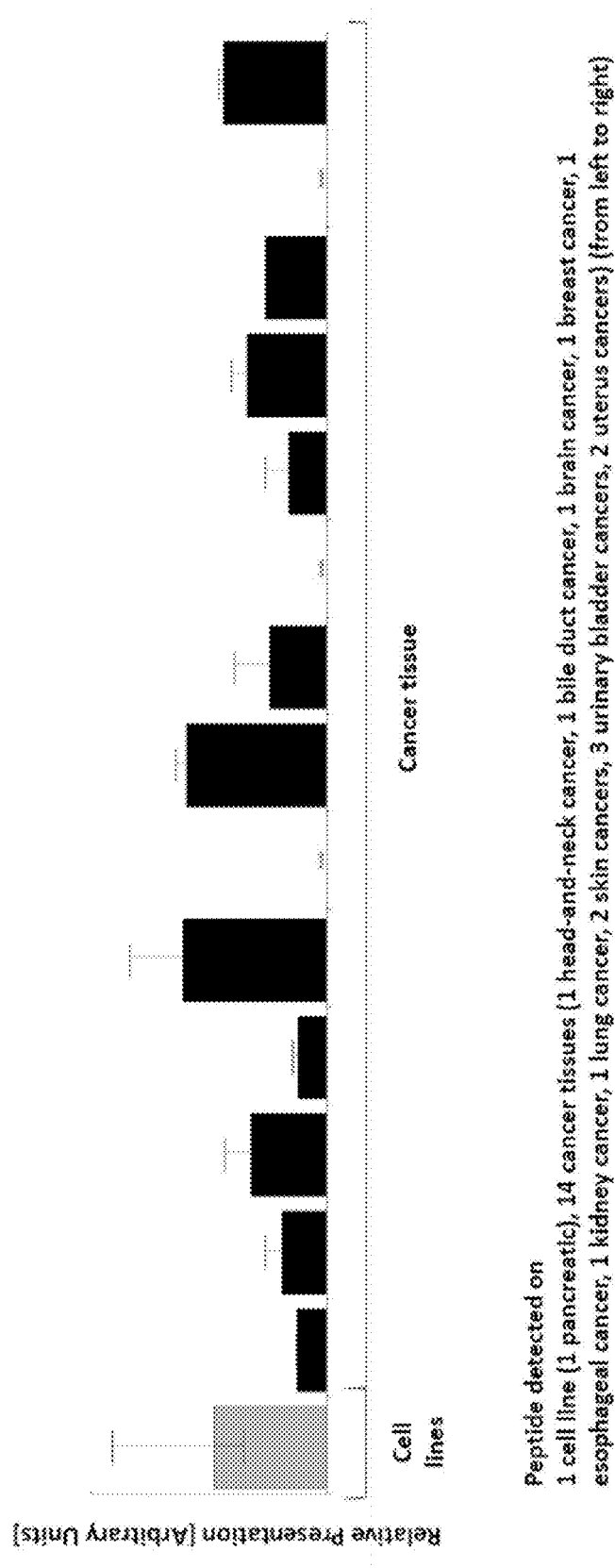

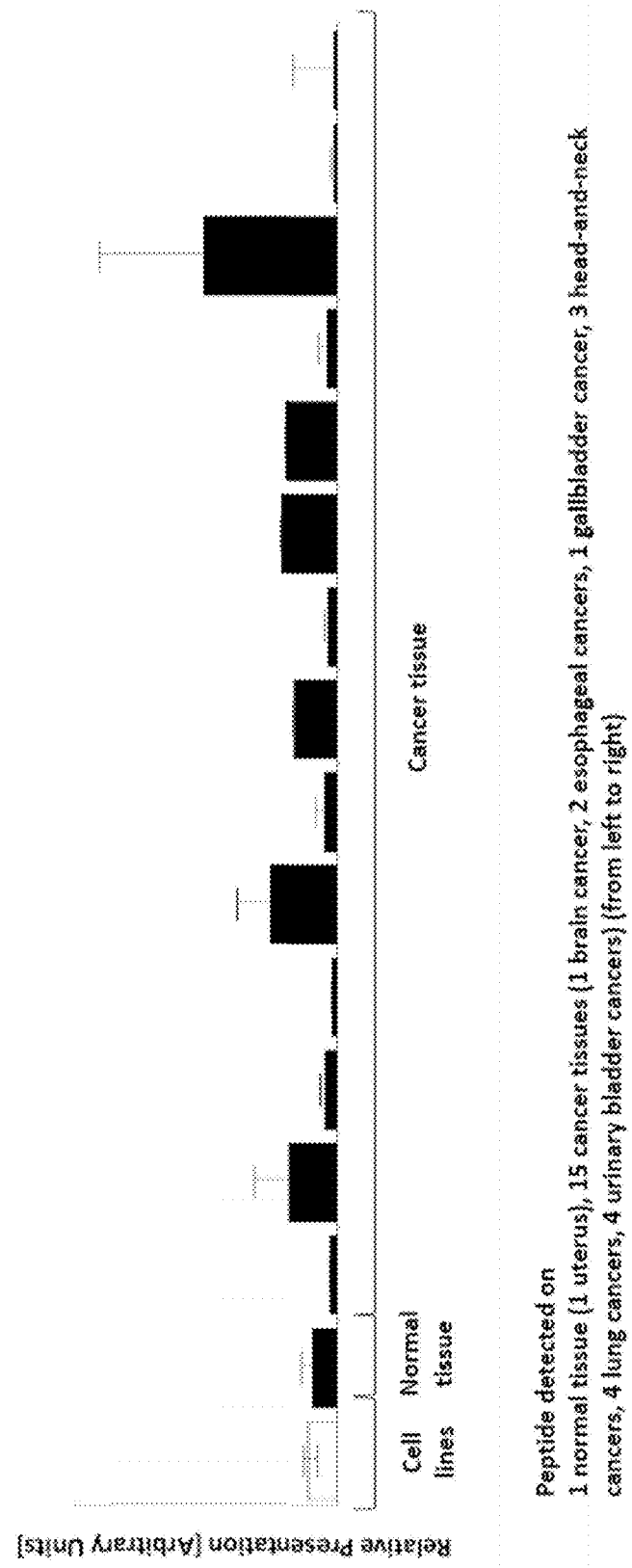

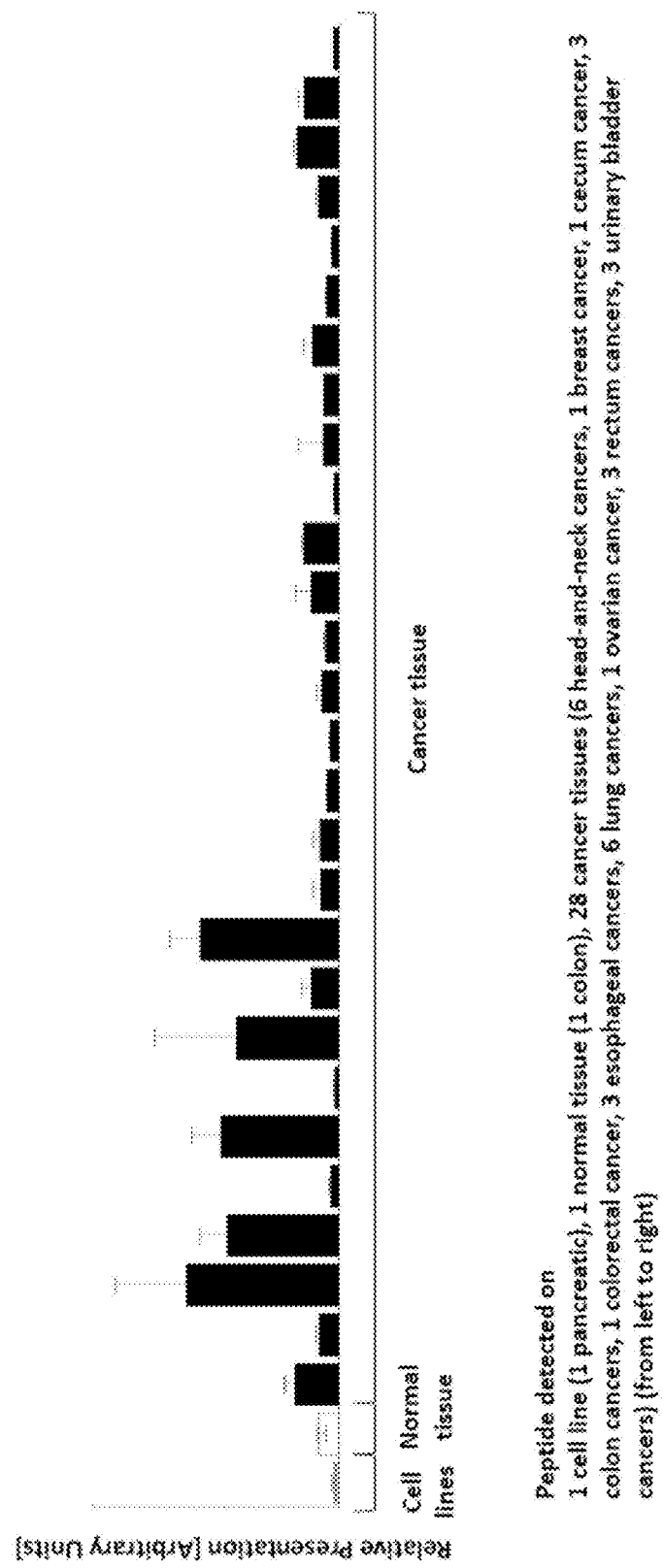

Peptide: GLAFSLYQA (A*02)
SEQ ID NO: 40

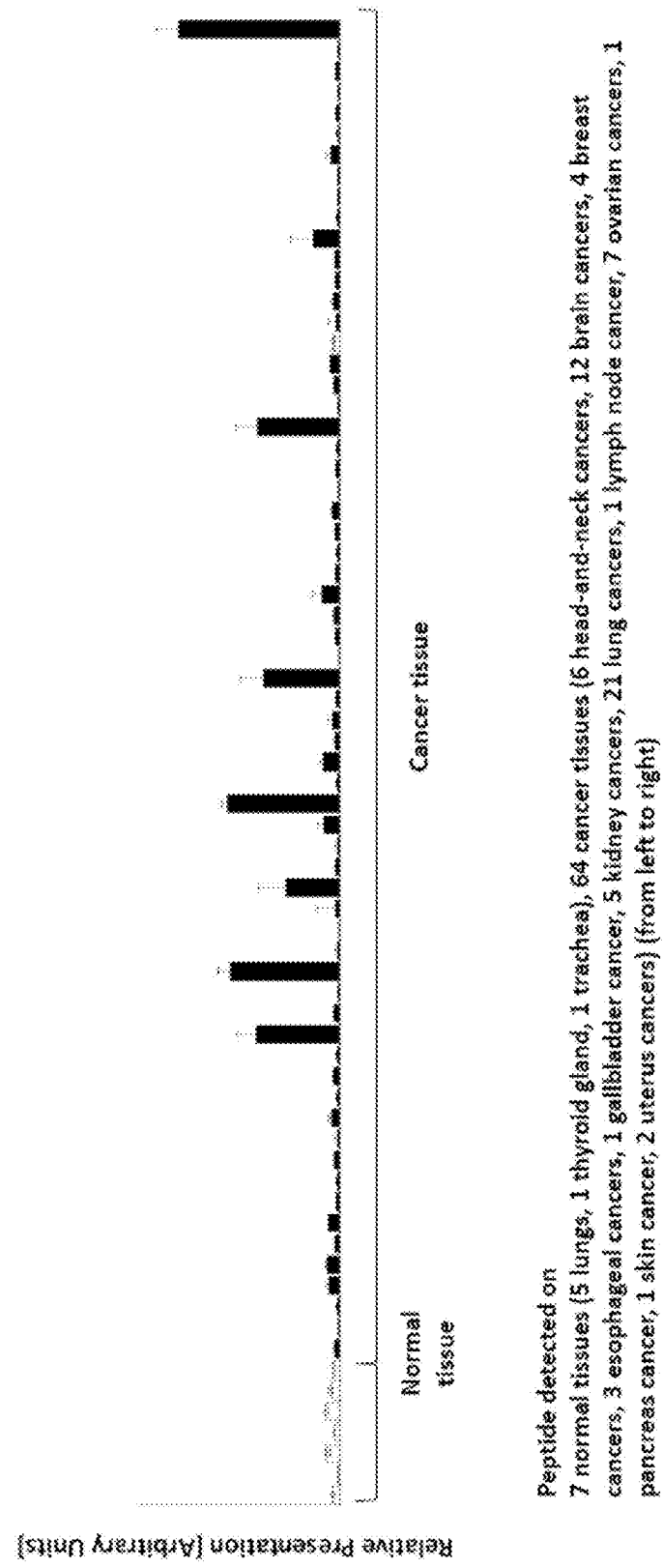

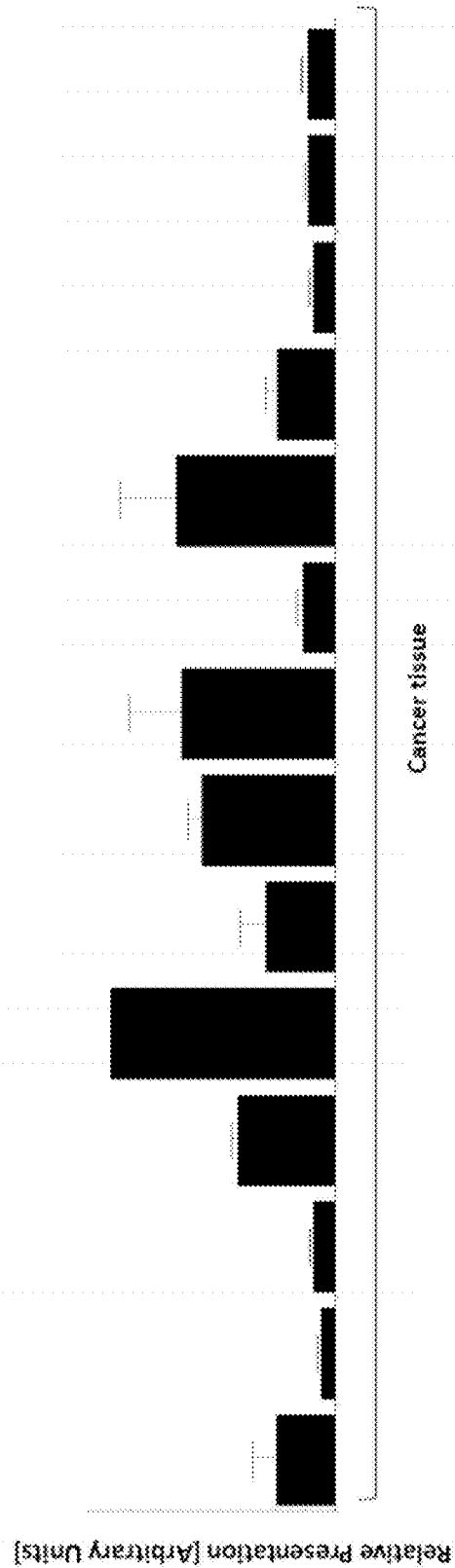

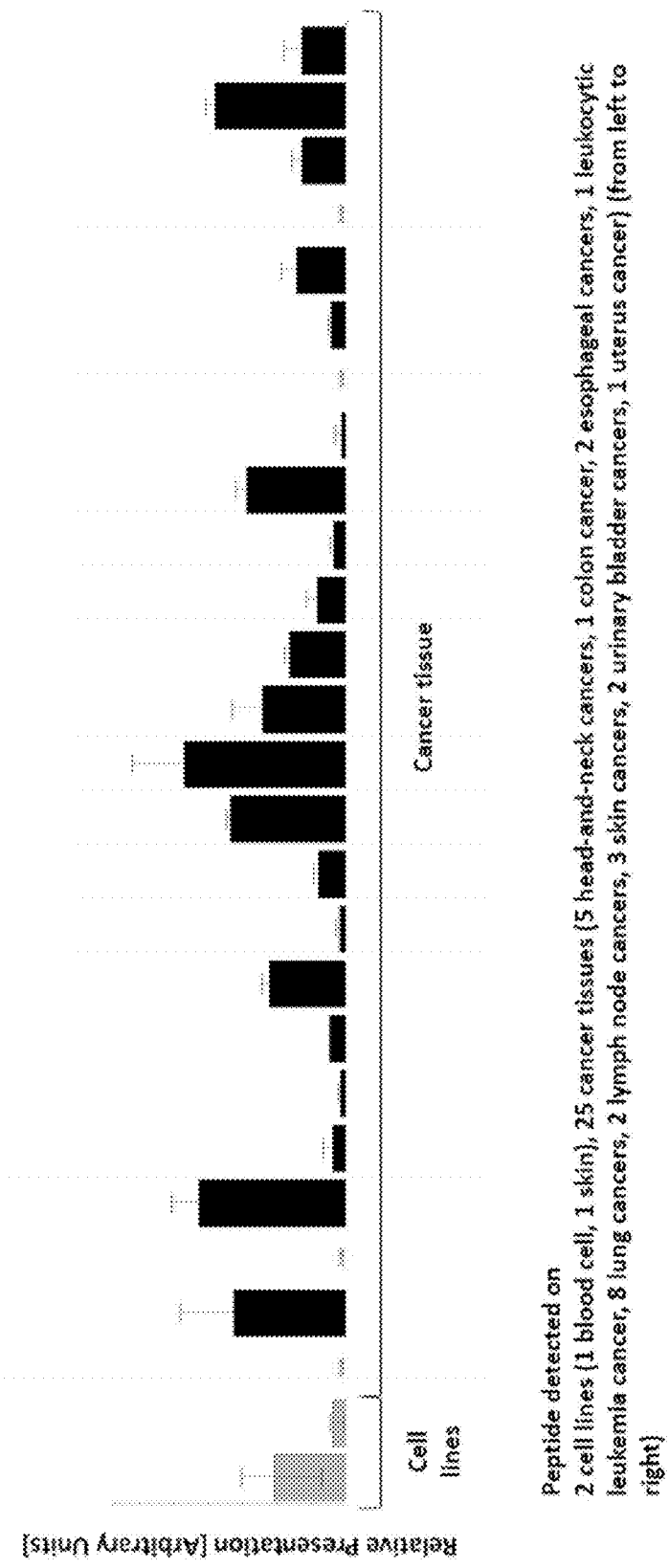

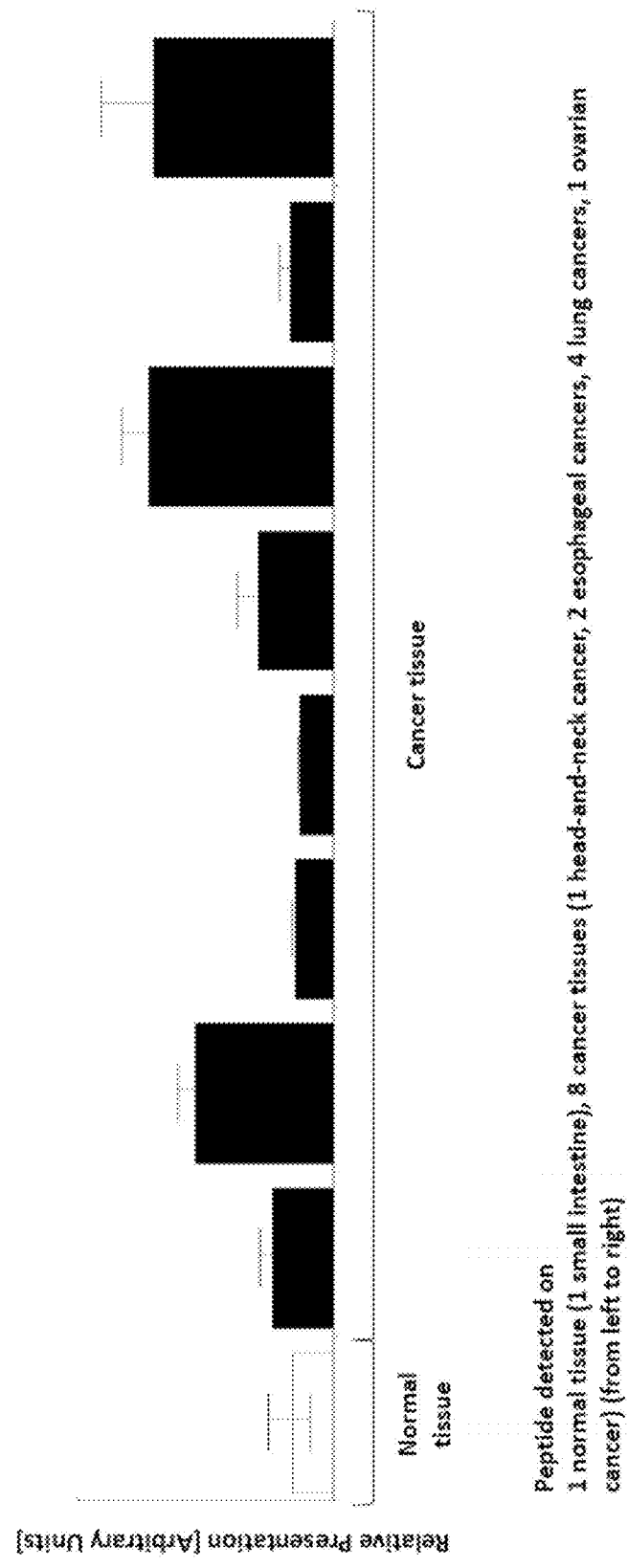

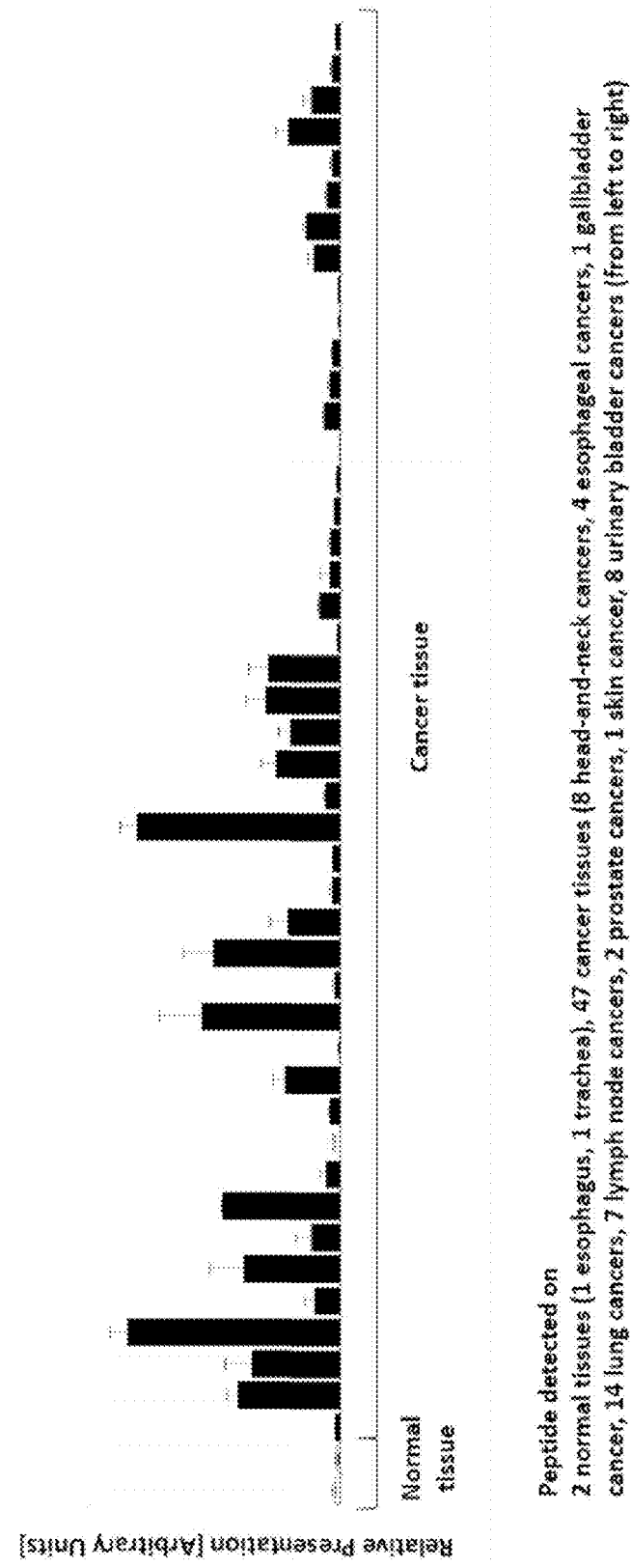

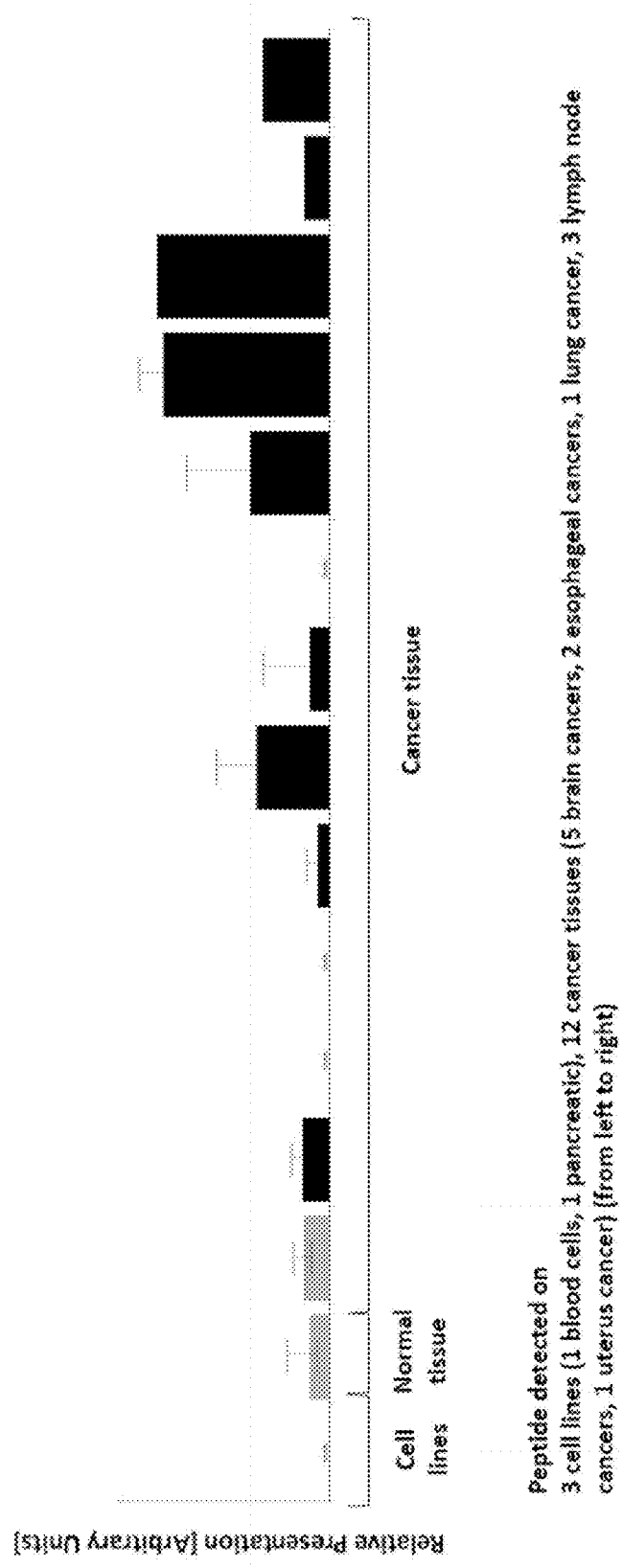

Gene: PTHLH
Peptide: HLIAEIHTA
SEQ ID NO: 9

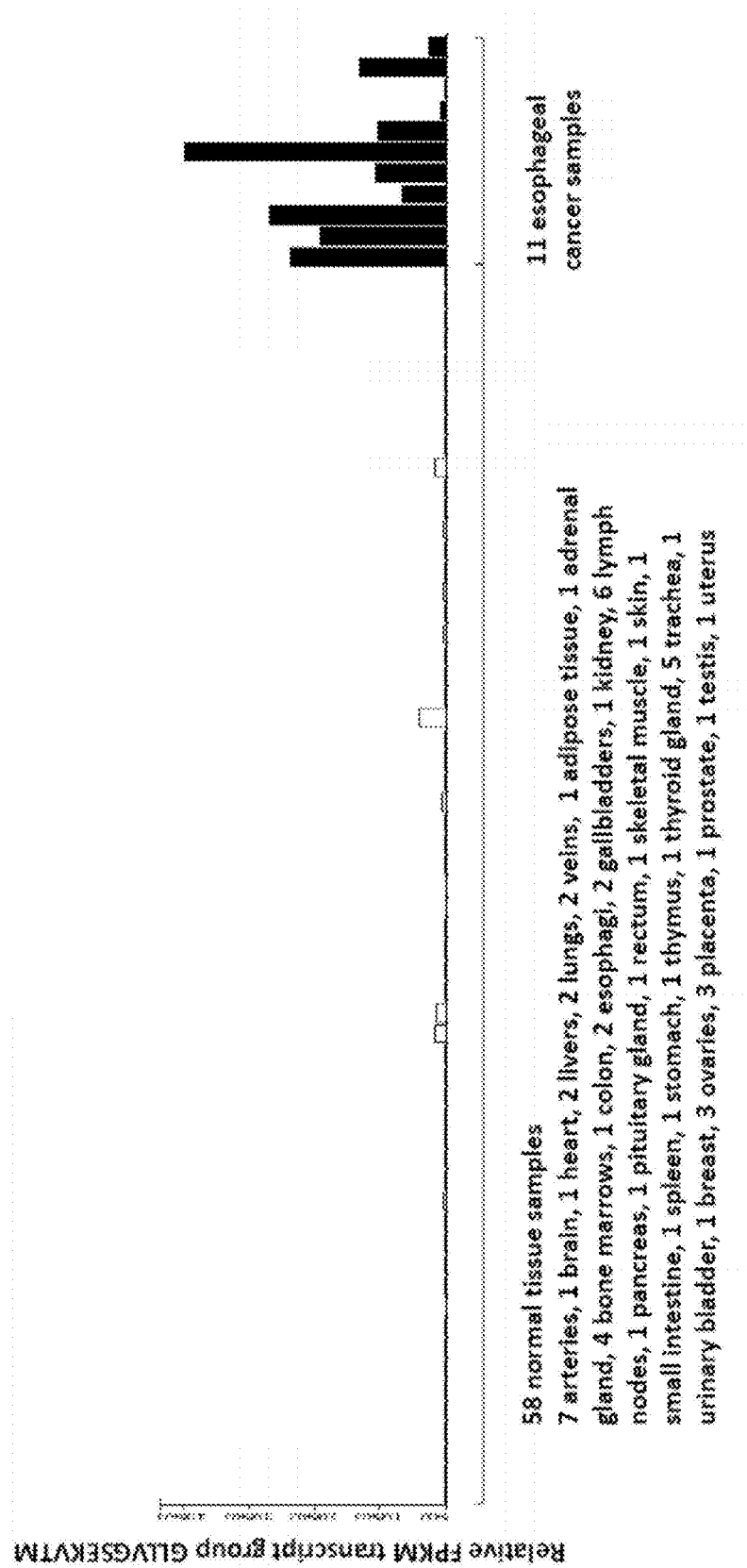

Gene: FAM83A
Peptide: ALLDGGSEAYWRV
SEQ ID NO: 8

Gene: PDPN
Peptide: VLAEGGEGV
SEQ ID NO: 16

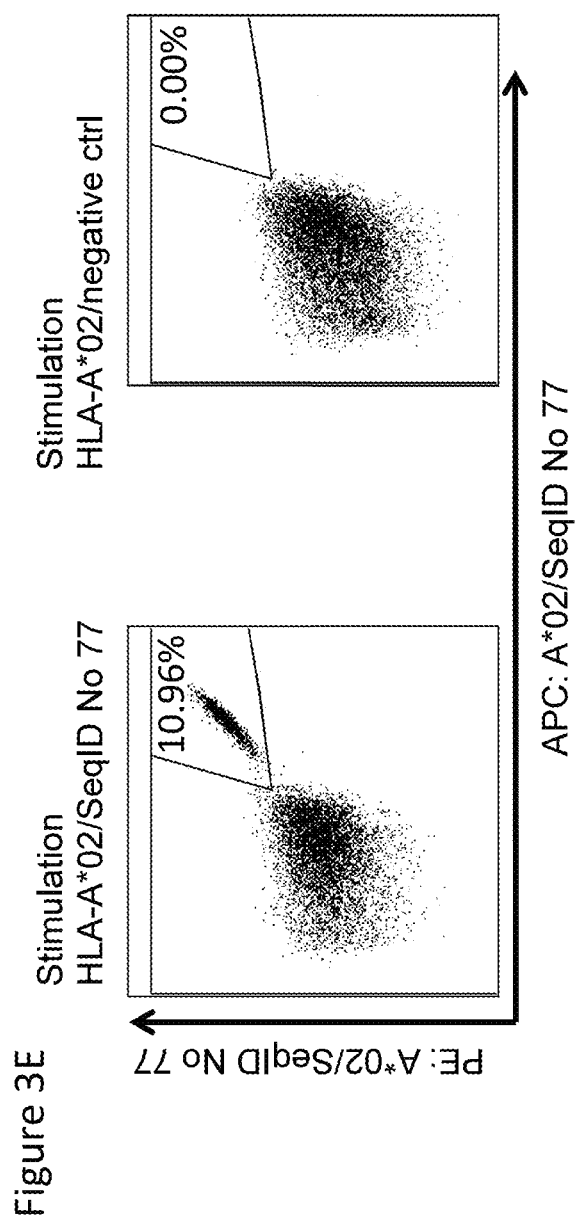

SEQUENCE LISTING

<160> NUMBER OF SEQ ID NOS: 103

<210> SEQ ID NO 1
<211> LENGTH: 9
<212> TYPE: PRT
<213> ORGANISM: Homo sapiens

<400> SEQUENCE: 1

Ser Thr Tyr Gly Gly Gly Leu Ser Val
1               5

<210> SEQ ID NO 2
<211> LENGTH: 13
<212> TYPE: PRT
<213> ORGANISM: Homo sapiens

<400> SEQUENCE: 2

Ser Leu Tyr Asn Leu Gly Gly Ser Lys Arg Ile Ser Ile
1               5                   10

<210> SEQ ID NO 3
<211> LENGTH: 9
<212> TYPE: PRT
<213> ORGANISM: Homo sapiens

<400> SEQUENCE: 3

Thr Ala Ser Ala Ile Thr Pro Ser Val
1               5

<210> SEQ ID NO 4
<211> LENGTH: 9
<212> TYPE: PRT
<213> ORGANISM: Homo sapiens

<400> SEQUENCE: 4

Ala Leu Phe Gly Thr Ile Leu Glu Leu
1               5

<210> SEQ ID NO 5
<211> LENGTH: 9
<212> TYPE: PRT
<213> ORGANISM: Homo sapiens

<400> SEQUENCE: 5

Asn Leu Met Ala Ser Gln Pro Gln Leu
1               5

<210> SEQ ID NO 6
<211> LENGTH: 9
<212> TYPE: PRT
<213> ORGANISM: Homo sapiens

<400> SEQUENCE: 6

Leu Leu Ser Gly Asp Leu Ile Phe Leu
1               5

<210> SEQ ID NO 7
<211> LENGTH: 10
<212> TYPE: PRT
<213> ORGANISM: Homo sapiens

<400> SEQUENCE: 7

Ser Ile Phe Glu Gly Leu Leu Ser Gly Val
1               5                   10

<210> SEQ ID NO 8
<211> LENGTH: 13
<212> TYPE: PRT
<213> ORGANISM: Homo sapiens

<400> SEQUENCE: 8

Ala Leu Leu Asp Gly Gly Ser Glu Ala Tyr Trp Arg Val
1               5                   10

<210> SEQ ID NO 9
<211> LENGTH: 9
<212> TYPE: PRT
<213> ORGANISM: Homo sapiens

<400> SEQUENCE: 9

His Leu Ile Ala Glu Ile His Thr Ala
1               5

<210> SEQ ID NO 10
<211> LENGTH: 10
<212> TYPE: PRT
<213> ORGANISM: Homo sapiens

<400> SEQUENCE: 10

Ser Leu Asp Glu Asn Ser Asp Gln Gln Val
1               5                   10

<210> SEQ ID NO 11
<211> LENGTH: 11
<212> TYPE: PRT
<213> ORGANISM: Homo sapiens

<400> SEQUENCE: 11

Ala Leu Trp Leu Pro Thr Asp Ser Ala Thr Val
1               5                   10

<210> SEQ ID NO 12
<211> LENGTH: 9
<212> TYPE: PRT
<213> ORGANISM: Homo sapiens

<400> SEQUENCE: 12

Gly Leu Ala Ser Arg Ile Leu Asp Ala
1               5

<210> SEQ ID NO 13
<211> LENGTH: 9
<212> TYPE: PRT
<213> ORGANISM: Homo sapiens

<400> SEQUENCE: 13

Ser Leu Ser Pro Val Ile Leu Gly Val
1               5

<210> SEQ ID NO 14
<211> LENGTH: 9
<212> TYPE: PRT
<213> ORGANISM: Homo sapiens

<400> SEQUENCE: 14

Arg Leu Pro Asn Ala Gly Thr Gln Val
1               5

<210> SEQ ID NO 15
<211> LENGTH: 9
<212> TYPE: PRT
<213> ORGANISM: Homo sapiens

<400> SEQUENCE: 15

Leu Leu Ala Asn Gly Val Tyr Ala Ala
1               5

-continued

```
<210> SEQ ID NO 16
<211> LENGTH: 9
<212> TYPE: PRT
<213> ORGANISM: Homo sapiens

<400> SEQUENCE: 16

Val Leu Ala Glu Gly Gly Glu Gly Val
1               5

<210> SEQ ID NO 17
<211> LENGTH: 8
<212> TYPE: PRT
<213> ORGANISM: Homo sapiens

<400> SEQUENCE: 17

Met Ile Ser Arg Thr Pro Glu Val
1               5

<210> SEQ ID NO 18
<211> LENGTH: 10
<212> TYPE: PRT
<213> ORGANISM: Homo sapiens

<400> SEQUENCE: 18

Phe Leu Leu Asp Gln Val Gln Leu Gly Leu
1               5                   10

<210> SEQ ID NO 19
<211> LENGTH: 10
<212> TYPE: PRT
<213> ORGANISM: Homo sapiens

<400> SEQUENCE: 19

Gly Leu Ala Pro Phe Leu Leu Asn Ala Val
1               5                   10

<210> SEQ ID NO 20
<211> LENGTH: 12
<212> TYPE: PRT
<213> ORGANISM: Homo sapiens

<400> SEQUENCE: 20

Ile Ile Glu Val Asp Pro Asp Thr Lys Glu Met Leu
1               5                   10

<210> SEQ ID NO 21
<211> LENGTH: 9
<212> TYPE: PRT
<213> ORGANISM: Homo sapiens

<400> SEQUENCE: 21

Ile Val Arg Glu Phe Leu Thr Ala Leu
1               5

<210> SEQ ID NO 22
<211> LENGTH: 9
<212> TYPE: PRT
<213> ORGANISM: Homo sapiens

<400> SEQUENCE: 22

Lys Leu Asn Asp Thr Tyr Val Asn Val
1               5

<210> SEQ ID NO 23
<211> LENGTH: 9
```

<212> TYPE: PRT
<213> ORGANISM: Homo sapiens

<400> SEQUENCE: 23

Lys Leu Ser Asp Ser Ala Thr Tyr Leu
1               5

<210> SEQ ID NO 24
<211> LENGTH: 9
<212> TYPE: PRT
<213> ORGANISM: Homo sapiens

<400> SEQUENCE: 24

Leu Leu Phe Ala Gly Thr Met Thr Val
1               5

<210> SEQ ID NO 25
<211> LENGTH: 9
<212> TYPE: PRT
<213> ORGANISM: Homo sapiens

<400> SEQUENCE: 25

Leu Leu Pro Pro Pro Pro Pro Pro Ala
1               5

<210> SEQ ID NO 26
<211> LENGTH: 9
<212> TYPE: PRT
<213> ORGANISM: Homo sapiens

<400> SEQUENCE: 26

Met Leu Ala Glu Lys Leu Leu Gln Ala
1               5

<210> SEQ ID NO 27
<211> LENGTH: 9
<212> TYPE: PRT
<213> ORGANISM: Homo sapiens

<400> SEQUENCE: 27

Asn Leu Arg Glu Gly Asp Gln Leu Leu
1               5

<210> SEQ ID NO 28
<211> LENGTH: 9
<212> TYPE: PRT
<213> ORGANISM: Homo sapiens

<400> SEQUENCE: 28

Ser Leu Asp Gly Phe Thr Ile Gln Val
1               5

<210> SEQ ID NO 29
<211> LENGTH: 9
<212> TYPE: PRT
<213> ORGANISM: Homo sapiens

<400> SEQUENCE: 29

Ser Leu Asp Gly Thr Glu Leu Gln Leu
1               5

<210> SEQ ID NO 30
<211> LENGTH: 9
<212> TYPE: PRT
<213> ORGANISM: Homo sapiens

<400> SEQUENCE: 30

Ser Leu Asn Gly Asn Gln Val Thr Val
1               5

<210> SEQ ID NO 31
<211> LENGTH: 9
<212> TYPE: PRT
<213> ORGANISM: Homo sapiens

<400> SEQUENCE: 31

Val Leu Pro Lys Leu Tyr Val Lys Leu
1               5

<210> SEQ ID NO 32
<211> LENGTH: 9
<212> TYPE: PRT
<213> ORGANISM: Homo sapiens

<400> SEQUENCE: 32

Tyr Met Leu Asp Ile Phe His Glu Val
1               5

<210> SEQ ID NO 33
<211> LENGTH: 12
<212> TYPE: PRT
<213> ORGANISM: Homo sapiens

<400> SEQUENCE: 33

Gly Leu Asp Val Thr Ser Leu Arg Pro Phe Asp Leu
1               5                   10

<210> SEQ ID NO 34
<211> LENGTH: 10
<212> TYPE: PRT
<213> ORGANISM: Homo sapiens

<400> SEQUENCE: 34

Ser Leu Val Ser Glu Gln Leu Glu Pro Ala
1               5                   10

<210> SEQ ID NO 35
<211> LENGTH: 9
<212> TYPE: PRT
<213> ORGANISM: Homo sapiens

<400> SEQUENCE: 35

Leu Leu Arg Phe Ser Gln Asp Asn Ala
1               5

<210> SEQ ID NO 36
<211> LENGTH: 10
<212> TYPE: PRT
<213> ORGANISM: Homo sapiens

<400> SEQUENCE: 36

Phe Leu Leu Arg Phe Ser Gln Asp Asn Ala
1               5                   10

<210> SEQ ID NO 37
<211> LENGTH: 12
<212> TYPE: PRT
<213> ORGANISM: Homo sapiens

<400> SEQUENCE: 37

Tyr Thr Gln Pro Phe Ser His Tyr Gly Gln Ala Leu
1               5                   10

<210> SEQ ID NO 38
<211> LENGTH: 9
<212> TYPE: PRT
<213> ORGANISM: Homo sapiens

<400> SEQUENCE: 38

Ile Ala Ala Ile Arg Gly Phe Leu Val
1               5

<210> SEQ ID NO 39
<211> LENGTH: 10
<212> TYPE: PRT
<213> ORGANISM: Homo sapiens

<400> SEQUENCE: 39

Leu Val Arg Asp Thr Gln Ser Gly Ser Leu
1               5                   10

<210> SEQ ID NO 40
<211> LENGTH: 9
<212> TYPE: PRT
<213> ORGANISM: Homo sapiens

<400> SEQUENCE: 40

Gly Leu Ala Phe Ser Leu Tyr Gln Ala
1               5

<210> SEQ ID NO 41
<211> LENGTH: 12
<212> TYPE: PRT
<213> ORGANISM: Homo sapiens

<400> SEQUENCE: 41

Gly Leu Glu Ser Glu Glu Leu Glu Pro Glu Glu Leu
1               5                   10

<210> SEQ ID NO 42
<211> LENGTH: 9
<212> TYPE: PRT
<213> ORGANISM: Homo sapiens

<400> SEQUENCE: 42

Thr Gln Thr Ala Val Ile Thr Arg Ile
1               5

<210> SEQ ID NO 43
<211> LENGTH: 9
<212> TYPE: PRT
<213> ORGANISM: Homo sapiens

<400> SEQUENCE: 43

Lys Val Val Gly Lys Asp Tyr Leu Leu
1               5

<210> SEQ ID NO 44
<211> LENGTH: 14
<212> TYPE: PRT
<213> ORGANISM: Homo sapiens

<400> SEQUENCE: 44

Ala Thr Gly Asn Asp Arg Lys Glu Ala Ala Glu Asn Ser Leu

```
1               5                  10
```

<210> SEQ ID NO 45
<211> LENGTH: 9
<212> TYPE: PRT
<213> ORGANISM: Homo sapiens

<400> SEQUENCE: 45

```
Met Leu Thr Glu Leu Glu Lys Ala Leu
1               5
```

<210> SEQ ID NO 46
<211> LENGTH: 11
<212> TYPE: PRT
<213> ORGANISM: Homo sapiens

<400> SEQUENCE: 46

```
Tyr Thr Ala Gln Ile Gly Ala Asp Ile Ala Leu
1               5                  10
```

<210> SEQ ID NO 47
<211> LENGTH: 9
<212> TYPE: PRT
<213> ORGANISM: Homo sapiens

<400> SEQUENCE: 47

```
Val Leu Ala Ser Gly Phe Leu Thr Val
1               5
```

<210> SEQ ID NO 48
<211> LENGTH: 10
<212> TYPE: PRT
<213> ORGANISM: Homo sapiens

<400> SEQUENCE: 48

```
Ser Met His Gln Met Leu Asp Gln Thr Leu
1               5                  10
```

<210> SEQ ID NO 49
<211> LENGTH: 9
<212> TYPE: PRT
<213> ORGANISM: Homo sapiens

<400> SEQUENCE: 49

```
Gly Leu Met Lys Asp Ile Val Gly Ala
1               5
```

<210> SEQ ID NO 50
<211> LENGTH: 11
<212> TYPE: PRT
<213> ORGANISM: Homo sapiens

<400> SEQUENCE: 50

```
Gly Met Asn Pro His Gln Thr Pro Ala Gln Leu
1               5                  10
```

<210> SEQ ID NO 51
<211> LENGTH: 9
<212> TYPE: PRT
<213> ORGANISM: Homo sapiens

<400> SEQUENCE: 51

```
Lys Leu Phe Gly His Leu Thr Ser Ala
1               5
```

```
<210> SEQ ID NO 52
<211> LENGTH: 12
<212> TYPE: PRT
<213> ORGANISM: Homo sapiens

<400> SEQUENCE: 52

Val Ala Ile Gly Gly Val Asp Gly Asn Val Arg Leu
1               5                   10

<210> SEQ ID NO 53
<211> LENGTH: 9
<212> TYPE: PRT
<213> ORGANISM: Homo sapiens

<400> SEQUENCE: 53

Val Val Val Thr Gly Leu Thr Leu Val
1               5

<210> SEQ ID NO 54
<211> LENGTH: 9
<212> TYPE: PRT
<213> ORGANISM: Homo sapiens

<400> SEQUENCE: 54

Tyr Gln Asp Leu Leu Asn Val Lys Met
1               5

<210> SEQ ID NO 55
<211> LENGTH: 9
<212> TYPE: PRT
<213> ORGANISM: Homo sapiens

<400> SEQUENCE: 55

Gly Ala Ile Asp Leu Leu His Asn Val
1               5

<210> SEQ ID NO 56
<211> LENGTH: 9
<212> TYPE: PRT
<213> ORGANISM: Homo sapiens

<400> SEQUENCE: 56

Ala Leu Val Glu Val Thr Glu His Val
1               5

<210> SEQ ID NO 57
<211> LENGTH: 10
<212> TYPE: PRT
<213> ORGANISM: Homo sapiens

<400> SEQUENCE: 57

Gly Leu Ala Pro Asn Thr Pro Gly Lys Ala
1               5                   10

<210> SEQ ID NO 58
<211> LENGTH: 9
<212> TYPE: PRT
<213> ORGANISM: Homo sapiens

<400> SEQUENCE: 58

Leu Ile Leu Glu Ser Ile Pro Val Val
1               5

<210> SEQ ID NO 59
```

<210> SEQ ID NO 59
<211> LENGTH: 9
<212> TYPE: PRT
<213> ORGANISM: Homo sapiens

<400> SEQUENCE: 59

Ser Leu Leu Asp Thr Leu Arg Glu Val
1               5

<210> SEQ ID NO 60
<211> LENGTH: 9
<212> TYPE: PRT
<213> ORGANISM: Homo sapiens

<400> SEQUENCE: 60

Val Val Met Glu Glu Leu Leu Lys Val
1               5

<210> SEQ ID NO 61
<211> LENGTH: 9
<212> TYPE: PRT
<213> ORGANISM: Homo sapiens

<400> SEQUENCE: 61

Thr Gln Thr Thr His Glu Leu Thr Ile
1               5

<210> SEQ ID NO 62
<211> LENGTH: 10
<212> TYPE: PRT
<213> ORGANISM: Homo sapiens

<400> SEQUENCE: 62

Ala Leu Tyr Glu Tyr Gln Pro Leu Gln Ile
1               5                   10

<210> SEQ ID NO 63
<211> LENGTH: 10
<212> TYPE: PRT
<213> ORGANISM: Homo sapiens

<400> SEQUENCE: 63

Leu Ala Tyr Thr Leu Gly Val Lys Gln Leu
1               5                   10

<210> SEQ ID NO 64
<211> LENGTH: 9
<212> TYPE: PRT
<213> ORGANISM: Homo sapiens

<400> SEQUENCE: 64

Gly Leu Thr Asp Val Ile Arg Asp Val
1               5

<210> SEQ ID NO 65
<211> LENGTH: 11
<212> TYPE: PRT
<213> ORGANISM: Homo sapiens

<400> SEQUENCE: 65

Tyr Val Val Gly Gly Phe Leu Tyr Gln Arg Leu
1               5                   10

<210> SEQ ID NO 66
<211> LENGTH: 9
<212> TYPE: PRT

```
<213> ORGANISM: Homo sapiens

<400> SEQUENCE: 66

Leu Leu Asp Glu Lys Val Gln Ser Val
1               5

<210> SEQ ID NO 67
<211> LENGTH: 9
<212> TYPE: PRT
<213> ORGANISM: Homo sapiens

<400> SEQUENCE: 67

Ser Met Asn Gly Gly Val Phe Ala Val
1               5

<210> SEQ ID NO 68
<211> LENGTH: 12
<212> TYPE: PRT
<213> ORGANISM: Homo sapiens

<400> SEQUENCE: 68

Pro Ala Val Leu Gln Ser Ser Gly Leu Tyr Ser Leu
1               5                   10

<210> SEQ ID NO 69
<211> LENGTH: 11
<212> TYPE: PRT
<213> ORGANISM: Homo sapiens

<400> SEQUENCE: 69

Gly Leu Leu Val Gly Ser Glu Lys Val Thr Met
1               5                   10

<210> SEQ ID NO 70
<211> LENGTH: 9
<212> TYPE: PRT
<213> ORGANISM: Homo sapiens

<400> SEQUENCE: 70

Phe Val Leu Asp Thr Ser Glu Ser Val
1               5

<210> SEQ ID NO 71
<211> LENGTH: 12
<212> TYPE: PRT
<213> ORGANISM: Homo sapiens

<400> SEQUENCE: 71

Ala Ser Asp Pro Ile Leu Tyr Arg Pro Val Ala Val
1               5                   10

<210> SEQ ID NO 72
<211> LENGTH: 9
<212> TYPE: PRT
<213> ORGANISM: Homo sapiens

<400> SEQUENCE: 72

Phe Leu Pro Pro Ala Gln Val Thr Val
1               5

<210> SEQ ID NO 73
<211> LENGTH: 9
<212> TYPE: PRT
<213> ORGANISM: Homo sapiens
```

```
<400> SEQUENCE: 73

Lys Ile Thr Glu Ala Ile Gln Tyr Val
1               5

<210> SEQ ID NO 74
<211> LENGTH: 9
<212> TYPE: PRT
<213> ORGANISM: Homo sapiens

<400> SEQUENCE: 74

Ile Leu Ala Ser Leu Ala Thr Ser Val
1               5

<210> SEQ ID NO 75
<211> LENGTH: 10
<212> TYPE: PRT
<213> ORGANISM: Homo sapiens

<400> SEQUENCE: 75

Gly Leu Met Asp Asp Val Asp Phe Lys Ala
1               5                   10

<210> SEQ ID NO 76
<211> LENGTH: 9
<212> TYPE: PRT
<213> ORGANISM: Homo sapiens

<400> SEQUENCE: 76

Lys Val Ala Asp Tyr Ile Pro Gln Leu
1               5

<210> SEQ ID NO 77
<211> LENGTH: 10
<212> TYPE: PRT
<213> ORGANISM: Homo sapiens

<400> SEQUENCE: 77

Val Leu Val Pro Tyr Glu Pro Pro Gln Val
1               5                   10

<210> SEQ ID NO 78
<211> LENGTH: 9
<212> TYPE: PRT
<213> ORGANISM: Homo sapiens

<400> SEQUENCE: 78

Lys Val Ala Asn Ile Ile Ala Glu Val
1               5

<210> SEQ ID NO 79
<211> LENGTH: 9
<212> TYPE: PRT
<213> ORGANISM: Homo sapiens

<400> SEQUENCE: 79

Gly Gln Asp Val Gly Arg Tyr Gln Val
1               5

<210> SEQ ID NO 80
<211> LENGTH: 9
<212> TYPE: PRT
<213> ORGANISM: Homo sapiens

<400> SEQUENCE: 80
```

```
Ala Leu Gln Glu Ala Leu Glu Asn Ala
1               5

<210> SEQ ID NO 81
<211> LENGTH: 9
<212> TYPE: PRT
<213> ORGANISM: Homo sapiens

<400> SEQUENCE: 81

Ala Val Leu Pro His Val Asp Gln Val
1               5

<210> SEQ ID NO 82
<211> LENGTH: 9
<212> TYPE: PRT
<213> ORGANISM: Homo sapiens

<400> SEQUENCE: 82

His Leu Leu Gly His Leu Glu Gln Ala
1               5

<210> SEQ ID NO 83
<211> LENGTH: 10
<212> TYPE: PRT
<213> ORGANISM: Homo sapiens

<400> SEQUENCE: 83

Ala Leu Ala Asp Gly Val Val Ser Gln Ala
1               5                   10

<210> SEQ ID NO 84
<211> LENGTH: 9
<212> TYPE: PRT
<213> ORGANISM: Homo sapiens

<400> SEQUENCE: 84

Ser Leu Ala Glu Ser Leu Asp Gln Ala
1               5

<210> SEQ ID NO 85
<211> LENGTH: 9
<212> TYPE: PRT
<213> ORGANISM: Homo sapiens

<400> SEQUENCE: 85

Asn Ile Ile Glu Leu Val His Gln Val
1               5

<210> SEQ ID NO 86
<211> LENGTH: 9
<212> TYPE: PRT
<213> ORGANISM: Homo sapiens

<400> SEQUENCE: 86

Gly Leu Leu Thr Glu Ile Arg Ala Val
1               5

<210> SEQ ID NO 87
<211> LENGTH: 9
<212> TYPE: PRT
<213> ORGANISM: Homo sapiens

<400> SEQUENCE: 87

Phe Leu Asp Asn Gly Pro Lys Thr Ile
1               5
```

<210> SEQ ID NO 88
<211> LENGTH: 9
<212> TYPE: PRT
<213> ORGANISM: Homo sapiens

<400> SEQUENCE: 88

Gly Leu Trp Glu Gln Glu Asn His Leu
1               5

<210> SEQ ID NO 89
<211> LENGTH: 9
<212> TYPE: PRT
<213> ORGANISM: Homo sapiens

<400> SEQUENCE: 89

Ser Leu Ala Asp Ser Leu Tyr Asn Leu
1               5

<210> SEQ ID NO 90
<211> LENGTH: 9
<212> TYPE: PRT
<213> ORGANISM: Homo sapiens

<400> SEQUENCE: 90

Ser Ile Tyr Glu Tyr Tyr His Ala Leu
1               5

<210> SEQ ID NO 91
<211> LENGTH: 9
<212> TYPE: PRT
<213> ORGANISM: Homo sapiens

<400> SEQUENCE: 91

Lys Leu Ile Asp Asp Val His Arg Leu
1               5

<210> SEQ ID NO 92
<211> LENGTH: 9
<212> TYPE: PRT
<213> ORGANISM: Homo sapiens

<400> SEQUENCE: 92

Ser Ile Leu Arg His Val Ala Glu Val
1               5

<210> SEQ ID NO 93
<211> LENGTH: 9
<212> TYPE: PRT
<213> ORGANISM: Homo sapiens

<400> SEQUENCE: 93

Val Leu Ile Asn Thr Ser Val Thr Leu
1               5

<210> SEQ ID NO 94
<211> LENGTH: 11
<212> TYPE: PRT
<213> ORGANISM: Homo sapiens

<400> SEQUENCE: 94

Thr Leu Leu Gln Glu Gln Gly Thr Lys Thr Val
1               5                   10

<210> SEQ ID NO 95
<211> LENGTH: 9
<212> TYPE: PRT
<213> ORGANISM: Homo sapiens

<400> SEQUENCE: 95

Leu Ile Gln Asp Arg Val Ala Glu Val
1               5

<210> SEQ ID NO 96
<211> LENGTH: 10
<212> TYPE: PRT
<213> ORGANISM: Homo sapiens

<400> SEQUENCE: 96

Gly Ala Ala Val Arg Ile Gly Ser Val Leu
1               5                   10

<210> SEQ ID NO 97
<211> LENGTH: 9
<212> TYPE: PRT
<213> ORGANISM: Homo sapiens

<400> SEQUENCE: 97

Glu Leu Asp Arg Thr Pro Pro Glu Val
1               5

<210> SEQ ID NO 98
<211> LENGTH: 9
<212> TYPE: PRT
<213> ORGANISM: Homo sapiens

<400> SEQUENCE: 98

Val Leu Phe Pro Asn Leu Lys Thr Val
1               5

<210> SEQ ID NO 99
<211> LENGTH: 10
<212> TYPE: PRT
<213> ORGANISM: Homo sapiens

<400> SEQUENCE: 99

Arg Val Ala Pro Glu Glu His Pro Val Leu
1               5                   10

<210> SEQ ID NO 100
<211> LENGTH: 10
<212> TYPE: PRT
<213> ORGANISM: Homo sapiens

<400> SEQUENCE: 100

Gly Leu Tyr Pro Asp Ala Phe Ala Pro Val
1               5                   10

<210> SEQ ID NO 101
<211> LENGTH: 9
<212> TYPE: PRT
<213> ORGANISM: Homo sapiens

<400> SEQUENCE: 101

Ala Met Thr Gln Leu Leu Ala Gly Val
1               5

<210> SEQ ID NO 102
<211> LENGTH: 10

```
<212> TYPE: PRT
<213> ORGANISM: Homo sapiens

<400> SEQUENCE: 102

Glu Leu Ala Gly Ile Gly Ile Leu Thr Val
1               5                   10

<210> SEQ ID NO 103
<211> LENGTH: 9
<212> TYPE: PRT
<213> ORGANISM: Homo sapiens

<400> SEQUENCE: 103

Tyr Leu Leu Pro Ala Ile Val His Ile
1               5
```

PEPTIDES AND COMBINATION OF PEPTIDES FOR USE IN IMMUNOTHERAPY AGAINST ESOPHAGEAL CANCER AND OTHER CANCERS

CROSS REFERENCE TO RELATED APPLICATIONS

This application is a Continuation of U.S. application Ser. No. 16/137,489, filed Sep. 20, 2018, which is a Continuation of U.S. application Ser. No. 15/965,305, filed Apr. 27, 2018, which is a Continuation of U.S. application Ser. No. 15/202,388, filed Jul. 5, 2016 (now U.S. Pat. No. 10,011,645, issued Jul. 3, 2018), which claims the benefit of U.S. Provisional Application Ser. No. 62/188,870, filed Jul. 6, 2015, and Great Britain Application No. 1511792.2, filed Jul. 6, 2015, the content of each of these applications is herein incorporated by reference in their entirety.

This application also is related to PCT/EP2016/065812 filed Jul. 5, 2016, the content of which is incorporated herein by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "2912919-051010_Sequence_Listing_ST25" created on Feb. 19, 2019, and 16,384 bytes in size) is submitted concurrently with the instant application, and the entire contents of the Sequence Listing are incorporated herein by reference.

FIELD

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I molecules of human tumor cells that can be used in vaccine compositions for eliciting anti-tumor immune responses, or as targets for the development of pharmaceutically/immunologically active compounds and cells.

BACKGROUND OF THE INVENTION

Esophageal cancer is the eighth most common cancer worldwide, with a five-year prevalence of 464,063 patients in 2012. Mortality rates are very similar to incidence rates (400,169 versus 455,784 in 2012), pointing out the high fatality of esophageal cancer (World Cancer Report, 2014; Ferlay et al., 2013; Bray et al., 2013).

Squamous cell carcinoma and adenocarcinoma represent the two most common subtypes of esophageal cancer. Both subtypes are more common in men than in women, but they display distinct geographical distributions. Squamous cell carcinoma is more prevalent in low-resource regions with particularly high incidence rates in the Islamic Republic of Iran, parts of China and Zimbabwe. Adenocarcinoma is the most common type of esophageal cancer among Caucasians and populations with a high socioeconomic status, with the United Kingdom, Australia, the Netherlands and the USA leading the way. The strongest risk factors for the development of esophageal squamous cell carcinoma include alcohol and tobacco consumption, whereas esophageal adenocarcinoma is mainly associated with obesity and gastro-esophageal reflux disease. Incidence rates of esophageal adenocarcinoma are steadily rising in high-income countries, which might be attributed to increasing rates of obesity and gastro-esophageal reflux disease as well as to changes in the classification of tumors at the gastro-esophageal junction. Neuroendocrine carcinoma, adenoid cystic carcinoma, adenosquamous carcinoma, muco-epidermoid carcinoma, mixed adenoneuroendocrine carcinoma, different sarcomas and melanoma represent rarer subtypes of esophageal cancer (World Cancer Report, 2014).

The primary treatment strategy for esophageal cancer depends on tumor stage and location, histological type and the medical condition of the patient. Surgery alone is not sufficient, except in a small subgroup of patients with squamous cell carcinoma. In general, surgery should be combined with pre- and eventually post-operative chemotherapy or pre-operative chemoradiation, while pre- or post-operative radiation alone was shown to confer no survival benefit. Chemotherapeutic regimens include oxaliplatin plus fluorouracil, carboplatin plus paclitaxel, cisplatin plus fluorouracil, FOLFOX and cisplatin plus irinotecan. Patients with HER2-positive tumors should be treated according to the guidelines for gastric cancer using a combination of cisplatin, fluorouracil and trastuzumab, as randomized data for targeted therapies in esophageal cancer are very limited (Stahl et al., 2013; Leitlinie Magenkarzinom, 2012).

In general, most types of esophageal cancer are well manageable, if patients present with early-stage tumors, whereas therapeutic success is very limited in later stages. Thus, development of new screening protocols could be very effective in reducing esophageal cancer-related mortality rates (World Cancer Report, 2014).

Immunotherapy might be a promising novel approach to treat advanced esophageal cancer. Several cancer-associated genes and cancer-testis antigens were shown to be over-expressed in esophageal cancer, including different MAGE genes, NY-ESO-1 and EpCAM (Kimura et al., 2007; Liang et al., 2005b; Inoue et al., 1995; Bujas et al., 2011; Tanaka et al., 1997; Quillien et al., 1997). Those genes represent very interesting targets for immunotherapy and most of them are under investigation for the treatment of other malignancies (ClinicalTrials.gov, 2015). Furthermore, up-regulation of PD-L1 and PD-L2 was described in esophageal cancer, which correlated with poorer prognosis. Thus, esophageal cancer patients with PD-L1-positive tumors might benefit from anti-PD-L1 immunotherapy (Ohigashi et al., 2005).

Clinical data on immunotherapeutic approaches in esophageal cancer are still relatively scarce at present, as only a very limited number of early phase clinical trials have been completed (Toomey et al., 2013). A vaccine consisting of three peptides derived from three different cancer-testis antigens (TTK protein kinase, lymphocyte antigen 6 complex locus K and insulin-like growth factor (IGF)-II mRNA binding protein 3) was administered to patients with advanced esophageal cancer in a phase I trial with moderate results (Kono et al., 2009). Intra-tumoral injection of activated T cells after in vitro challenge with autologous malignant cells and interleukin 2 elicited complete or partial tumor responses in four of eleven patients in a phase I/II study (Toh et al., 2000; Toh et al., 2002). Further clinical trials are currently performed to evaluate the impact of different immunotherapies on esophageal cancer, including adoptive cellular therapy (NCT01691625, NCT01691664, NCT01795976, NCT02096614, NCT02457650) vaccination strategies (NCT01143545, NCT01522820) and anti-PD-L1 therapy (NCT02340975) (ClinicalTrials.gov, 2015).

Considering the severe side-effects and expense associated with treating cancer, there is a need to identify factors that can be used in the treatment of cancer in general and esophageal cancer in particular. There is also a need to identify factors representing biomarkers for cancer in general and esophageal cancer in particular, leading to better diagnosis of cancer, assessment of prognosis, and prediction of treatment success.

Immunotherapy of cancer represents an option of specific targeting of cancer cells while minimizing side effects. Cancer immunotherapy makes use of the existence of tumor associated antigens.

The current classification of tumor associated antigens (TAAs) comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.

d) Tumor-specific antigens: These unique TAAs arise from mutations of normal genes (such as β-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor- (-associated) exon in case of proteins with tumor-specific (-associated) isoforms.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides. MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in the literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis, and are subsequently processed.

Complexes of peptide and MHC class I are recognized by CD8-positive T cells bearing the appropriate T-cell receptor (TCR), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses (Gnjatic et al., 2003). At the tumor site, T helper cells, support a cytotoxic T cell- (CTL-) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006).

Elongated (longer) peptides of the invention can act as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T cells as direct anti-tumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-I-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Basically, any peptide able to bind an MHC molecule may function as a T-cell epitope. A prerequisite for the induction of an in vitro or in vivo T-cell-response is the presence of a T cell having a corresponding TCR and the absence of immunological tolerance for this particular epitope.

Therefore, TAAs are a starting point for the development of a T cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

SUMMARY OF THE INVENTION

In a first aspect of the present invention, the present invention relates to a peptide comprising an amino acid sequence selected from the group consisting of SEQ ID NO: 1 to SEQ ID NO: 93 or a variant sequence thereof which is at least 77%, preferably at least 88%, homologous (preferably at least 77% or at least 88% identical) to SEQ ID NO: 1 to SEQ ID NO: 93, wherein said variant binds to MHC and/or induces T cells cross-reacting with said peptide, or a pharmaceutical acceptable salt thereof, wherein said peptide is not the underlying full-length polypeptide.

The present invention further relates to a peptide of the present invention comprising a sequence that is selected from the group consisting of SEQ ID NO: 1 to SEQ ID NO: 93 or a variant thereof, which is at least 77%, preferably at least 88%, homologous (preferably at least 77% or at least 88% identical) to SEQ ID NO: 1 to SEQ ID NO: 93, wherein said peptide or variant thereof has an overall length of between 8 and 100, preferably between 8 and 30, and most preferred of between 8 and 14 amino acids.

The following tables show the peptides according to the present invention, their respective SEQ ID NOs, and the prospective source (underlying) genes for these peptides. All peptides in Table 1 and Table 2 bind to HLA-A*02. The peptides in Table 2 have been disclosed before in large listings as results of high-throughput screenings with high error rates or calculated using algorithms, but have not been associated with cancer at all before. The peptides in Table 3 are additional peptides that may be useful in combination with the other peptides of the invention. The peptides in Table 4 are furthermore useful in the diagnosis and/or treatment of various other malignancies that involve an over-expression or over-presentation of the respective underlying polypeptide.

TABLE 1

Peptides according to the present invention

| SEQ ID No | Sequence | Gene ID(s) | Official Gene Symbol(s) |
|---|---|---|---|
| 1 | STYGGGLSV | 3861, 3868 | KRT14, KRT16 |
| 2 | SLYNLGGSKRISI | 3852 | KRT5 |
| 3 | TASAITPSV | 3852 | KRT5 |
| 4 | ALFGTILEL | 2769 | GNA15 |
| 5 | NLMASQPQL | 5317 | PKP1 |
| 6 | LLSGDLIFL | 2709 | GJB5 |
| 7 | SIFEGLLSGV | 2709 | GJB5 |
| 8 | ALLDGGSEAYWRV | 84985 | FAM83A |
| 9 | HLIAEIHTA | 5744 | PTHLH |
| 10 | SLDENSDQQV | 6273 | S100A2 |
| 11 | ALWLPTDSATV | 3914 | LAMB3 |
| 12 | GLASRILDA | 3914 | LAMB3 |
| 13 | SLSPVILGV | 26525 | IL36RN |
| 14 | RLPNAGTQV | 3655 | ITGA6 |
| 15 | LLANGVYAA | 55107 | ANO1 |
| 16 | VLAEGGEGV | 10630 | PDPN |
| 17 | MISRTPEV | 2155, 28396, 3500, 3501, 3502, 3503, 3507 | F7, IGHV4-31, IGHG1, IGHG2, IGHG3, IGHG4, IGHM |
| 18 | FLLDQVQLGL | 83882 | TSPAN10 |
| 19 | GLAPFLLNAV | 101060689, 154761, 285966 | FAM115C |
| 20 | IIEVDPDTKEML | 100505503, 402057, 442216, 6218 | RPS17L, RPS17P16, RPS17P5, RPS17 |
| 21 | IVREFLTAL | 27297 | CRCP |
| 22 | KLNDTYVNV | 23306 | TMEM194A |
| 23 | KLSDSATYL |  | No associated gene |
| 24 | LLFAGTMTV | 29785 | CYP2S1 |
| 25 | LLPPPPPPA | 9509 | ADAMTS2 |
| 26 | MLAEKLLQA | 2195 | FAT1 |
| 27 | NLREGDQLL | 113146 | AHNAK2 |
| 28 | SLDGFTIQV | 4939 | OAS2 |
| 29 | SLDGTELQL | 284114 | TMEM102 |
| 30 | SLNGNQVTV | 79832 | QSER1 |
| 31 | VLPKLYVKL | 100996747, 441502, 6231, 643003, 644928, 728937, 729188 | RPS26P11, RPS26, RPS26P28, RPS26P15, RPS26P25, RPS26P58 |
| 32 | YMLDIFHEV | 3038 | HAS3 |
| 33 | GLDVTSLRPFDL | 2316 | FLNA |
| 34 | SLVSEQLEPA | 11187 | PKP3 |
| 35 | LLRFSQDNA | 51056 | LAP3 |
| 36 | FLLRFSQDNA | 51056 | LAP3 |
| 37 | YTQPFSHYGQAL | 6051 | RNPEP |
| 38 | IAAIRGFLV | 83451 | ABHD11 |
| 39 | LVRDTQSGSL | 871 | SERPINH1 |
| 40 | GLAFSLYQA | 871 | SERPINH1 |
| 41 | GLESEELEPEEL | 8106 | PABPN1 |
| 42 | TQTAVITRI | 81610 | FAM83D |
| 43 | KVVGKDYLL | 832 | CAPZB |
| 44 | ATGNDRKEAAENSL | 7531 | YWHAE |
| 45 | MLTELEKAL | 6279 | S100A8 |
| 46 | YTAQIGADIAL | 64499, 7177 | TPSB2, TPSAB1 |
| 47 | VLASGFLTV | 79183 | TTPAL |
| 48 | SMHQMLDQTL | 7168 | TPM1 |
| 49 | GLMKDIVGA | 8942 | KYNU |
| 50 | GMNPHQTPAQL | 471 | ATIC |
| 51 | KLFGHLTSA | 57157 | PHTF2 |
| 52 | VAIGGVDGNVRL | 9948 | WDR1 |
| 53 | VVVTGLTLV | 396 | ARHGDIA |
| 54 | YQDLLNVKM | 1674, 4741, 4744, 4747, 7431, 9118 | DES, NEFM, NEFH, NEFL, VIM, INA |
| 55 | GAIDLLHNV | 115362 | GBPS |
| 56 | ALVEVTEHV | 54972 | TMEM132A |
| 57 | GLAPNTPGKA | 9055 | PRC1 |
| 58 | LILESIPVV | 5597 | MAPK6 |

TABLE 1-continued

Peptides according to the present invention

| SEQ ID No | Sequence | Gene ID(s) | Official Gene Symbol(s) |
|---|---|---|---|
| 59 | SLLDTLREV | 9989 | PPP4R1 |
| 60 | VVMEELLKV | 23191 | CYFIP1 |
| 61 | TQTTHELTI | 5093 | PCBP1 |
| 62 | ALYEYQPLQI | 4331 | MNAT1 |
| 63 | LAYTLGVKQL | 158078, 1915, 1917 | EEF1A1P5, EEF1A1, EEF1A2 |
| 64 | GLTDVIRDV | 80028 | FBXL18 |
| 65 | YVVGGFLYQRL | 4074 | M6PR |
| 66 | LLDEKVQSV | 57616 | TSHZ3 |
| 67 | SMNGGVFAV | 23657 | SLC7A11 |
| 68 | PAVLQSSGLYSL | 28396, 3500, 3501, 3502, 3503, 3507 | IGHV4-31, IGHG1, IGHG2, IGHG3, IGHG4, IGHM |
| 69 | GLLVGSEKVTM | 3861, 3868, 644945 | KRT14, KRT16, KRT16P3 |
| 70 | FVLDTSESV | 1291, 1292 | COL6A1, COL6A2 |
| 71 | ASDPILYRPVAV | 5315 | PKM |
| 72 | FLPPAQVTV | 65083 | NOL6 |
| 73 | KITEAIQYV | 6095 | RORA |
| 74 | ILASLATSV | 10844 | TUBGCP2 |
| 75 | GLMDDVDFKA | 10525 | HYOU1 |
| 76 | KVADYIPQL | 2744 | GLS |

TABLE 2

Additional peptides according to the present invention with no prior known cancer association

| SEQ ID No | Sequence | Gene ID(s) | Official Gene Symbol(s) |
|---|---|---|---|
| 77 | VLVPYEPPQV | 8626 | TP63 |
| 78 | KVANIIAEV | 5910 | RAP1GDS1 |
| 79 | GQDVGRYQV | 6748 | SSR4 |
| 80 | ALQEALENA | 9631 | NUP155 |
| 81 | AVLPHVDQV | 23379 | KIAA0947 |
| 82 | HLLGHLEQA | 63977 | PRDM15 |
| 83 | ALADGVVSQA | 27238 | GPKOW |
| 84 | SLAESLDQA | 22894 | DIS3 |
| 85 | NIIELVHQV | 6850 | SYK |
| 86 | GLLTEIRAV | 9263 | STK17A |
| 87 | FLDNGPKTI | 1982 | EIF4G2 |
| 88 | GLWEQENHL | 79768 | KATNBL1 |
| 89 | SLADSLYNL | 23271 | CAMSAP2 |
| 90 | SIYEYYHAL | 3091 | HIF1A |
| 91 | KLIDDVHRL | 6734 | SRPR |
| 92 | SILRHVAEV | 1965 | EIF2S1 |
| 93 | VLINTSVTL | 23036 | ZNF292 |

TABLE 3

Peptides useful for e.g. personalized cancer therapies

| SEQ ID No | Sequence | Gene ID(s) | Official Gene Symbol(s) |
|---|---|---|---|
| 94 | TLLQEQGTKTV | 286887, 3852, 3853, 3854 | KRT6C, KRT5, KRT6A, KRT6B |
| 95 | LIQDRVAEV | 3914 | LAMB3 |
| 96 | GAAVRIGSVL | 9150 | CTDP1 |
| 97 | ELDRTPPEV | 23450 | 5F3B3 |
| 98 | VLFPNLKTV | 646 | BNC1 |
| 99 | RVAPEEHPVL | 440915, 60, 641455, 71, 728378 | POTEKP, ACTB, POTEM, ACTG1, POTEF |
| 100 | GLYPDAFAPV | 1991 | ELANE |
| 101 | AMTQLLAGV | 3371 | TNC |

The present invention furthermore generally relates to the peptides according to the present invention for use in the treatment of proliferative diseases, such as, for example, lung cancer, urinary bladder cancer, ovarian cancer, melanoma, uterine cancer, hepatocellular cancer, renal cell cancer, brain cancer, colorectal cancer, breast cancer, gastric cancer, pancreatic cancer, gallbladder cancer, bile duct cancer, prostate cancer and leukemia.

Particularly preferred are the peptides—alone or in combination—according to the present invention selected from the group consisting of SEQ ID NO: 1 to SEQ ID NO: 93. More preferred are the peptides—alone or in combination—selected from the group consisting of SEQ ID NO: 1 to SEQ ID NO: 76 (see Table 1), and their uses in the immunotherapy of esophageal cancer, lung cancer, urinary bladder cancer, ovarian cancer, melanoma, uterine cancer, hepatocellular cancer, renal cell cancer, brain cancer, colorectal cancer, breast cancer, gastric cancer, pancreatic cancer, gallbladder cancer, bile duct cancer, prostate cancer and leukemia, and preferably esophageal cancer.

Particularly preferred are the peptides—alone or in combination—according to the present invention selected from the group consisting of SEQ ID No. 1, 2, 3, 5, 6, 7, 8, 9, 10, 11, 12, 13, 15, 16, 17, 18, 19, 25, 26, 30, 32, 34, 37, 40, 51, 55, 57, 58, 59, 62, 81, and 82, and their uses in the immunotherapy of esophageal cancer, lung cancer, urinary bladder cancer, ovarian cancer, melanoma, uterine cancer, hepatocellular cancer, renal cell cancer, brain cancer, colorectal cancer, breast cancer, gastric cancer, pancreatic cancer, gallbladder cancer, bile duct cancer, prostate cancer and leukemia, and preferably esophageal cancer. Further particularly preferred is the peptide according to SEQ ID NO:9.

As shown in the following Table 4A, many of the peptides according to the present invention are also found on other tumor types and can, thus, also be used in the immunotherapy of other indications. Also refer to FIGS. 1A-1V and Example 1.

TABLE 4A

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, gallbladder, heart, kidney, liver, lung, lymph node, mononuclear white blood cells, pancreas, peripheral nerve, peritoneum, pituitary, pleura, rectum, salivary gland, skeletal muscle, skin, small intestine, spleen, stomach, thymus, thyroid gland, trachea, ureter, urinary bladder, vein.

| SEQ ID No. | Sequence | Other relevant organs/diseases |
| --- | --- | --- |
| 2 | SLYNLGGSKRISI | NSCLC |
| 3 | TASAITPSV | NSCLC, Urinary bladder cancer |
| 4 | ALFGTILEL | NSCLC |
| 7 | SIFEGLLSGV | Urinary bladder cancer |
| 8 | ALLDGGSEAYWRV | NSCLC, OC |
| 9 | HLIAEIHTA | NSCLC |
| 11 | ALWLPTDSATV | NSCLC, Melanoma |
| 12 | GLASRILDA | Urinary bladder cancer |
| 13 | SLSPVILGV | Uterine Cancer |
| 15 | LLANGVYAA | HCC |
| 17 | MISRTPEV | NSCLC, RCC, HCC |
| 22 | KLNDTYVNV | SCLC, Brain Cancer, HCC |
| 26 | MLAEKLLQA | CRC |
| 29 | SLDGTELQL | BRCA |
| 31 | VLPKLYVKL | GC |
| 32 | YMLDIFHEV | Urinary bladder cancer |
| 33 | GLDVTSLRPFDL | GC |
| 34 | SLVSEQLEPA | CRC, Urinary bladder cancer |
| 35 | LLRFSQDNA | GC, HCC |
| 36 | FLLRFSQDNA | GC |
| 37 | YTQPFSHYGQAL | GC, PC |
| 38 | IAAIRGFLV | GC |
| 39 | LVRDTQSGSL | GC |
| 40 | GLAFSLYQA | NSCLC, PC, BRCA, Urinary bladder cancer |
| 41 | GLESEELEPEEL | GC |
| 42 | TQTAVITRI | GC |
| 45 | MLTELEKAL | GC |
| 46 | YTAQIGADIAL | GC |
| 47 | VLASGF | LTV Urinary bladder cancer |
| 49 | GLMKDIVGA | HCC |
| 50 | GMNPHQTPAQL | GC |
| 51 | KLFGHLTSA | Gallbladder Cancer, Bile Duct Cancer |
| 52 | VAIGGVDGNVRL | GC |
| 54 | YQDLLNVKM | RCC, GC |
| 55 | GAIDLLHNV | GC |
| 56 | ALVEVTEHV | BRCA |
| 57 | GLAPNTPGKA | NSCLC, SCLC, BRCA, Melanoma |
| 58 | LILESIPVV | NSCLC, Melanoma |
| 61 | TQTTHELTI | SCLC, Leukemia |
| 62 | ALYEYQPLQI | NSCLC, HCC, Urinary bladder cancer |
| 63 | LAYTLGVKQL | GC |
| 66 | LLDEKVQSV | Brain Cancer, Melanoma |
| 67 | SMNGGVFAV | Brain Cancer, HCC |
| 68 | PAVLQSSGLYSL | GC, PC |
| 69 | GLLVGSEKVTM | PC |
| 70 | FVLDTSESV | GC, HCC, Melanoma, OC |
| 71 | ASDPILYRPVAV | GC, PC |
| 72 | FLPPAQVTV | NSCLC, GC, HCC, Leukemia, Melanoma |
| 73 | KITEAIQYV | BRCA |
| 74 | ILASLATSV | CRC, HCC, Urinary bladder cancer |
| 75 | GLMDDVDFKA | BRCA, Melanoma, Urinary bladder cancer |
| 76 | KVADYIPQL | NSCLC, SCLC |
| 77 | VLVPYEPPQV | NSCLC, Urinary bladder cancer |
| 78 | KVANIIAEV | PC, Leukemia, OC |
| 80 | ALQEALENA | NSCLC, SCLC, Brain Cancer, CRC, HCC, Leukemia, BRCA, OC |
| 81 | AVLPHVDQV | Brain Cancer |
| 82 | HLLGHLEQA | NSCLC, HCC, Leukemia, BRCA |
| 83 | ALADGVVSQA | Brain Cancer, GC, Melanoma, Urinary bladder cancer |
| 85 | NIIELVHQV | Leukemia |
| 86 | GLLTEIRAV | Brain Cancer, Urinary bladder cancer |
| 87 | FLDNGPKTI | Brain Cancer, PC, OC |
| 88 | GLWEQENHL | NSCLC, BRCA |
| 89 | SLADSLYNL | Brain Cancer, BRCA, Urinary bladder cancer, |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, gallbladder, heart, kidney, liver, lung, lymph node, mononuclear white blood cells, pancreas, peripheral nerve, peritoneum, pituitary, pleura, rectum, salivary gland, skeletal muscle, skin, small intestine, spleen, stomach, thymus, thyroid gland, trachea, ureter, urinary bladder, vein.

| SEQ ID No. | Sequence | Other relevant organs/diseases |
| --- | --- | --- |
| | | Gallbladder Cancer, Bile Duct Cancer |
| 91 | KLIDDVHRL | PC, PrC |
| 92 | SILRHVAEV | NSCLC, CRC, HCC, Gallbladder Cancer, Bile Duct Cancer |
| 94 | TLLQEQGTKTV | NSCLC |

NSCLC = non-small cell lung cancer,
SCLC = small cell lung cancer,
RCC = kidney cancer,
CRC = colon or rectum cancer,
GC = stomach cancer,
HCC = liver cancer,
PC = pancreatic cancer,
PrC = prostate cancer, leukemia,
BrCa = breast cancer

TABLE 4B

Peptides according to the present invention and their specific uses in other proliferative diseases, especially in other cancerous diseases (amendment of Table 4). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, eye, gallbladder, heart, kidney, liver, lung, lymph node, mononuclear white blood cells, pancreas, parathyroid gland, peripheral nerve, peritoneum, pituitary, pleura, rectum, salivary gland, skeletal muscle, skin, small intestine, spleen, stomach, thyroid gland, trachea, ureter, urinary bladder, vein.

| SEQ ID No | Sequence | Additional Entities |
| --- | --- | --- |
| 1 | STYGGGLSV | NSCLC, Melanoma, HNSCC |
| 2 | SLYNLGGSKRISI | Urinary bladder cancer, HNSCC |
| 3 | TASAITPSV | HNSCC |
| 4 | ALFGTILEL | Urinary bladder cancer, Gallbladder Cancer, Bile Duct Cancer, AML, HNSCC |
| 5 | NLMASQPQL | HNSCC |
| 6 | LLSGDLIFL | HNSCC |
| 7 | SIFEGLLSGV | NSCLC, Gallbladder Cancer, Bile Duct Cancer, HNSCC |
| 8 | ALLDGGSEAYWRV | Urinary bladder cancer, HNSCC |
| 10 | SLDENSDQQV | Urinary bladder cancer, HNSCC |
| 11 | ALWLPTDSATV | Gallbladder Cancer, Bile Duct Cancer |
| 13 | SLSPVILGV | NSCLC, Melanoma, Urinary bladder cancer, HNSCC |
| 14 | RLPNAGTQV | Melanoma |
| 15 | LLANGVYAA | Urinary bladder cancer, Uterine Cancer, Gallbladder Cancer, Bile Duct Cancer |
| 16 | VLAEGGEGV | Brain Cancer, Melanoma, Gallbladder Cancer, Bile Duct Cancer, HNSCC |
| 17 | MISRTPEV | Urinary bladder cancer |
| 18 | FLLDQVQLGL | Melanoma, NHL, HNSCC |
| 19 | GLAPFLLNAV | Melanoma, NHL, HNSCC |
| 20 | IIEVDPDTKEML | HNSCC |
| 22 | KLNDTYVNV | BRCA |
| 23 | KLSDSATYL | Melanoma |
| 25 | LLPPPPPA | Gallbladder Cancer, Bile Duct Cancer, NHL, HNSCC |
| 28 | SLDGFTIQV | BRCA, Melanoma, AML |
| 29 | SLDGTELQL | Uterine Cancer, NHL |
| 30 | SLNGNQVTV | BRCA, Melanoma, Urinary bladder cancer, Uterine Cancer, Gallbladder Cancer, Bile Duct Cancer, HNSCC |

TABLE 4B-continued

Peptides according to the present invention and their specific uses in other proliferative diseases, especially in other cancerous diseases (amendment of Table 4). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, eye, gallbladder, heart, kidney, liver, lung, lymph node, mononuclear white blood cells, pancreas, parathyroid gland, peripheral nerve, peritoneum, pituitary, pleura, rectum, salivary gland, skeletal muscle, skin, small intestine, spleen, stomach, thyroid gland, trachea, ureter, urinary bladder, vein.

| SEQ ID No | Sequence | Additional Entities |
|---|---|---|
| 32 | YMLDIFHEV | Gallbladder Cancer, Bile Duct Cancer, HNSCC |
| 34 | SLVSEQLEPA | HNSCC |
| 40 | GLAFSLYQA | CRC, Melanoma, Uterine Cancer, Gallbladder Cancer, Bile Duct Cancer, HNSCC |
| 42 | TQTAVITRI | HNSCC |
| 48 | SMHQMLDQTL | GC |
| 51 | KLFGHLTSA | Gallbladder Cancer, Bile Duct Cancer |
| 53 | VVVTGLTLV | GC, Urinary bladder cancer |
| 55 | GAIDLLHNV | SCLC, Melanoma, NHL |
| 56 | ALVEVTEHV | RCC, Uterine Cancer, Gallbladder Cancer, Bile Duct Cancer |
| 57 | GLAPNTPGKA | Urinary bladder cancer, Uterine Cancer, HNSCC |
| 58 | LILESIPVV | SCLC, CLL, Urinary bladder cancer, Uterine Cancer, NHL, HNSCC |
| 59 | SLLDTLREV | HNSCC |
| 62 | ALYEYQPLQI | SCLC, BRCA, Melanoma, OC, Gallbladder Cancer, Bile Duct Cancer, NHL |
| 66 | LLDEKVQSV | Urinary bladder cancer, HNSCC |
| 67 | SMNGGVFAV | NSCLC, Gallbladder Cancer, Bile Duct Cancer, HNSCC |
| 68 | PAVLQSSGLYSL | NHL |
| 69 | GLLVGSEKVTM | HNSCC |
| 72 | FLPPAQVTV | CLL, Urinary bladder cancer, Gallbladder Cancer, Bile Duct Cancer, HNSCC |
| 74 | ILASLATSV | BRCA, HNSCC |
| 75 | GLMDDVDFKA | GC, HCC, Gallbladder Cancer, Bile Duct Cancer, NHL, HNSCC |
| 76 | KVADYIPQL | RCC, BRCA, Melanoma, Gallbladder Cancer, Bile Duct Cancer, NHL |
| 77 | VLVPYEPPQV | NHL, HNSCC |
| 78 | KVAN I IAEV | Urinary bladder cancer, HNSCC |
| 79 | GQDVGRYQV | SCLC, PC, PrC, CLL, BRCA, OC, Urinary bladder cancer, AML, NHL |
| 80 | ALQEALENA | Melanoma, Uterine Cancer, Gallbladder Cancer, Bile Duct Cancer, HNSCC |
| 81 | AVLPHVDQV | Uterine Cancer, NHL |
| 82 | HLLGHLEQA | RCC |
| 83 | ALADGVVSQA | Uterine Cancer |
| 84 | SLAESLDQA | Melanoma, Uterine Cancer, AML, NHL, HNSCC |
| 85 | NIIELVHQV | CLL |
| 86 | GLLTEIRAV | Melanoma, Gallbladder Cancer, Bile Duct Cancer, AML, NHL, HNSCC |
| 87 | FLDNGPKTI | Urinary bladder cancer, HNSCC |
| 88 | GLWEQENHL | CRC, Uterine Cancer, AML, HNSCC |
| 89 | SLADSLYNL | Melanoma |
| 90 | SIYEYYHAL | NHL, HNSCC |
| 92 | SILRHVAEV | BRCA, Melanoma, AML, NHL |

NSCLC = non-small cell lung cancer,
SCLC = small cell lung cancer,
RCC = kidney cancer,
CRC = colon or rectum cancer,
GC = stomach cancer,
HCC = liver cancer,
PC = pancreatic cancer,
PrC = prostate cancer,
BRCA = breast cancer,
OC = ovarian cancer,
NHL = non-Hodgkin lymphoma,
AML = acute myeloid leukemia,
CLL = chronic lymphocytic leukemia,
HNSCC = head and neck squamous cell carcinoma.

Thus, another aspect of the present invention relates to the use of at least one peptide according to the present invention according to any one of SEQ ID No. 1, 2, 3, 4, 7, 8, 9, 11, 13, 17, 40, 57, 58, 62, 67, 72, 76, 77, 80, 82, 88, 92 and 94 for the—in one preferred embodiment combined—treatment of non-small cell lung cancer.

Thus, another aspect of the present invention relates to the use of at least one peptide according to the present invention according to any one of SEQ ID No. 18, 19, 25, 29, 55, 58, 62, 68, 75, 76, 77, 79, 81, 84, 86, 90, and 92 for the—in one preferred embodiment combined—treatment of lymphoma.

Thus, another aspect of the present invention relates to the use of at least one peptide according to the present invention according to any one of SEQ ID No. 22, 55, 58, 62, 57, 61, 76, 79 and 80 for the—in one preferred embodiment combined—treatment of small-cell lung cancer.

Thus, another aspect of the present invention relates to the use of at least one peptide according to the present invention according to any one of SEQ ID No. 17, 56, 76, 82, and 54 for the—in one preferred embodiment combined—treatment of renal cell cancer.

Thus, another aspect of the present invention relates to the use of at least one peptide according to the present invention according to any one of SEQ ID No. 16, 22, 66, 67, 80, 81, 83, 86, 87 and 89 for the—in one preferred embodiment combined—treatment of brain cancer.

Thus, another aspect of the present invention relates to the use of at least one peptide according to the present invention according to any one of SEQ ID No. 31, 33, 35, 36, 37, 38, 39, 41, 42, 45, 46, 48, 50, 52, 53, 54, 55, 63, 68, 70, 75 and 71 for the—in one preferred embodiment combined—treatment of gastric cancer.

Thus, another aspect of the present invention relates to the use of at least one peptide according to the present invention according to any one of SEQ ID No. 26, 34, 40, 74, 80, 88, and 92 for the—in one preferred embodiment combined—treatment of colorectal cancer.

Thus, another aspect of the present invention relates to the use of at least one peptide according to the present invention according to any one of SEQ ID No. 15, 17, 22, 35, 49, 62, 67, 70, 72, 74, 75, 80, 82 and 92 for the—in one preferred embodiment combined—treatment of hepatocellular cancer.

Thus, another aspect of the present invention relates to the use of at least one peptide according to the present invention according to any one of SEQ ID No. 37, 40, 68, 69, 71, 78, 79, 87 and 91 for the—in one preferred embodiment combined—treatment of pancreatic cancer.

Thus, another aspect of the present invention relates to the use of at least one peptide according to the present invention according to any one of SEQ ID No. 79, and 91 for the—in one preferred embodiment combined—treatment of prostate cancer.

Thus, another aspect of the present invention relates to the use of at least one peptide according to the present invention according to any one of SEQ ID No. 4, 28, 58, 61, 72, 78, 79, 80, 82, 84, 86, 88, 92, and 85 for the—in one preferred embodiment combined—treatment of leukemia.

Thus, another aspect of the present invention relates to the use of at least one peptide according to the present invention according to any one of SEQ ID No. 22, 28, 29, 30, 40, 56, 57, 62, 73, 74, 75, 76, 79, 80, 82, 88, 92 and 89 for the—in one preferred embodiment combined—treatment of breast cancer.

Thus, another aspect of the present invention relates to the use of at least one peptide according to the present invention according to any one of SEQ ID No. 1, 13, 14, 11, 16, 18, 19, 23, 28, 30, 40, 55, 57, 58, 62, 66, 70, 72, 75, 76, 80, 84, 86, 89, 92, and 83 for the—in one preferred embodiment combined—treatment of melanoma.

Thus, another aspect of the present invention relates to the use of at least one peptide according to the present invention according to any one of SEQ ID No. 8, 62, 70, 78, 79, 80 and 87 for the—in one preferred embodiment combined—treatment of ovarian cancer.

Thus, another aspect of the present invention relates to the use of at least one peptide according to the present invention according to any one of SEQ ID No. 2, 3, 4, 7, 8, 10, 12, 13, 15, 17, 30, 32, 34, 40, 47, 53, 57, 58, 62, 66, 72, 74, 75, 77, 78, 79, 83, 86, 87, and 89 for the—in one preferred embodiment combined—treatment of urinary bladder cancer.

Thus, another aspect of the present invention relates to the use of at least one peptide according to the present invention according to any one of SEQ ID No. 13, 15, 29, 30, 40, 56, 57, 58, 80, 81, 83, 84, and 88 for the—in one preferred embodiment combined—treatment of uterine cancer.

Thus, another aspect of the present invention relates to the use of at least one peptide according to the present invention according to any one of SEQ ID No. 4, 7, 11, 15, 16, 25, 30, 32, 40, 51, 56, 62, 67, 72, 75, 76, 80, 86, 89 and 92 for the—in one preferred embodiment combined—treatment of gallbladder and bile duct cancer.

Thus, another aspect of the present invention relates to the use of at least one peptide according to the present invention according to any one of SEQ ID No. SEQ ID No 1, 2, 3, 4, 5, 6, 7, 8, 10, 13, 16, 18, 19, 20, 25, 30, 32, 34, 40, 42, 57, 58, 59, 66, 67, 69, 72, 74, 75, 77, 78, 80, 84, 86, 87, 88, and 90 for the—in one preferred embodiment combined—treatment of HNSCC.

Thus, another aspect of the present invention relates to the use of the peptides according to the present invention for the—preferably combined—treatment of a proliferative disease selected from the group of esophageal cancer, lung cancer, urinary bladder cancer, ovarian cancer, melanoma, uterine cancer, hepatocellular cancer, renal cell cancer, brain cancer, colorectal cancer, breast cancer, gastric cancer, pancreatic cancer, gallbladder cancer, bile duct cancer, prostate cancer and leukemia.

The present invention furthermore relates to peptides according to the present invention that have the ability to bind to a molecule of the human major histocompatibility complex (MHC) class-I or—in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 93.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and methods of making these, as well as NK cells or other cells bearing said TCR or cross-reacting with said TCRs.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID No. 1 to SEQ ID No.: 93, preferably containing SEQ ID No. 1 to SEQ ID No. 76, or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, said medicament is active against cancer.

Preferably, said medicament is a cellular therapy, a vaccine or a protein based on a soluble TCR or antibody.

The present invention further relates to a use according to the present invention, wherein said cancer cells are esophageal cancer, lung cancer, urinary bladder cancer, ovarian cancer, melanoma, uterine cancer, hepatocellular cancer, renal cell cancer, brain cancer, colorectal cancer, breast cancer, gastric cancer, pancreatic cancer, gallbladder cancer, bile duct cancer, prostate cancer and leukemia, and preferably esophageal cancer cells.

The present invention further relates to biomarkers based on the peptides according to the present invention, herein called "targets", that can be used in the diagnosis of cancer, preferably esophageal cancer. The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally, the antibody carries a further effector function such as an immune stimulating domain or toxin.

The present invention also relates to the use of these novel targets in the context of cancer treatment.

ABHD11 antisense RNA 1 (ABHD11-AS1) was described as a long noncoding RNA which was shown to be up-regulated in gastric cancer and associated with differentiation and Lauren histological classification. Thus, ABHD11-AS1 might be a potential biomarker for diagnosis of gastric cancer (Lin et al., 2014). ABHD11 activity was shown to be associated with the development of distant metastases in lung adenocarcinoma and thus might be a potential novel biomarker (Wiedl et al., 2011).

ADAMTS2 was shown to be dys-regulated in a patient with T/myeloid mixed phenotype acute leukemia (Tota et al., 2014). ADAMTS2 was described as being associated with the JNK pathway upon up-regulation through IL-6 in osteosarcoma cells (Alper and Kockar, 2014). ADAMTS2 may be a potential diagnostic marker for follicular thyroid cancer (Fontaine et al., 2009). ADAMTS2 was described as a potential marker of metastases in tongue squamous cell carcinoma (Carinci et al., 2005). ADAMTS2 was shown to be up-regulated in renal cell carcinoma and to be associated with shorter patient survival (Roemer et al., 2004). ADAMTS2 was shown to be regulated by the cell proliferation associated transforming growth factor-beta 1 (Wang et al., 2003).

AHNAK2 encodes the scaffold protein AHNAK nucleoprotein 2 (Marg et al., 2010). AHNAK2 is an important element of the non-classical secretion pathway of fibroblast growth factor 1 (FGF1), a factor involved in tumor growth and invasion (Kirov et al., 2015). ANO1 encodes anoctamin 1, a calcium-activated chloride channel associated with small intestinal sarcoma and oral cancer (RefSeq, 2002). ANO1 is amplified in esophageal squamous cell cancer (ESCC), gastrointestinal stromal tumor (GIST), head and neck squamous cell carcinoma (HNSCC), pancreatic and breast cancers (Qu et al., 2014).

ARHGDIA was shown to be down-regulated in hepatocellular carcinoma and upon breast cancer development (Liang et al., 2014; Bozza et al., 2015). ARHGDIA was shown to be associated with tumor invasion, metastasis, overall survival and time to recurrence in hepatocellular carcinoma. Thus, ARHGDIA may provide a potential therapeutic target for hepatocellular carcinoma (Liang et al., 2014). ARHGDIA was shown to be down-regulated in the lung cancer cell line A549 upon periplocin treatment. Periplocin-inhibited growth of the lung cancer cells thus may be associated with ARHGDIA (Lu et al., 2014). ARHGDIA knock-down was shown to be associated with increased apoptosis in lung-derived normal and cultured tumor cells. Thus, ARHGDIA was described as a negative regulator of apoptosis which may represent a potential therapeutic target (Gordon et al., 2011). ARHGDIA was described to be associated with ovarian clear cell and high-grade serous carcinoma staging (Canet et al., 2011). ARHGDIA was described as an apoptotic pathway related gene which was shown to be de-regulated in fibrosarcoma HT1080 cells upon TRAIL-mediated apoptosis (Daigeler et al., 2008). ARHGDIA was shown to be up-regulated in the oxaliplatin-resistant colonic cancer cell line THC8307/L-OHP and was described as a gene involved in anti-apoptosis. Thus, ARHGDIA may be a potential marker associated with oxaliplatin sensitivity (Tang et al., 2007). ARHGDIA over-expression was shown to be regulated by the putative tumor suppressor ACVR2, a member of the cancer-related TGFBR2 family, in a wild-type ACVR2 transfected MS I-H colon cancer cell line carrying an ACVR2 frameshift mutation (Deacu et al., 2004). ARHGDIA was described as a key regulator of the Rho GTPases. ARHGDIA depletion was shown to induce constitutive activation of Rho GTPases and COX-2 pathways in association with breast cancer progression in a breast cancer xenograft animal model (Bozza et al., 2015). ARHGDIA signaling was shown to be de-regulated in colorectal cancer (Sethi et al., 2015). ARHGDIA was shown to target MEK1/2-Erk upon SUMOylation, which is associated with inhibition of C-Jun/AP-1, cyclin dl transcription, and cell cycle progression. Thus, ARHGDIA is associated with suppression of cancer cell growth (Cao et al., 2014). ARHGDIA was described as a novel suppressor in prostate cancer which may play a critical role in regulating androgen receptor signaling and prostate cancer growth and progression (Zhu et al., 2013b).

ATIC was described as potential gene fusion partner of the cancer-associated anaplastic lymphoma kinase in anaplastic larger cell lymphoma (Cheuk and Chan, 2001). ATIC was shown to be presented as a chimeric fusion with ALK in an inflammatory myofibroblastic tumor of the urinary bladder (Debiec-Rychter et al., 2003). Inhibition of the aminoimidazole carboxyamide ribonucleotide transformylase (AICAR) activity of ATIC in a model breast cancer cell line was shown to result in dose-dependent reduction of cell numbers and cell division rates. Thus, ATIC may be a potential target in cancer therapy (Spurr et al., 2012).

CAPZB was reported to be over-expressed in human papillomaviruses 18-positive oral squamous cell carcinomas and was identified as prostate cancer susceptibility locus (Lo et al., 2007; Nwosu et al., 2001).

COL6A1 is up-regulated in the reactive stroma of castration-resistant prostate cancer and promotes tumor growth (Zhu et al., 2015). Col6A1 is over-expressed in CD166- pancreatic cancer cells that show stronger invasive and migratory activities than those of CD166+ cancer cells (Fujiwara et al., 2014). COL6A1 is highly expressed in bone metastasis (Blanco et al., 2012). COL6A1 was found to be up-regulated in cervical and ovarian cancer (Zhao et al., 2011; Parker et al., 2009). COL6A1 is differentially expressed in astrocytomas and glioblastomas (Fujita et al., 2008).

COL6A2 is associated with cervical cancer, poor overall survival in high-grade serous ovarian cancer, B-precursor acute lymphoblastic leukemia, hepatocellular carcinoma, primary and metastatic brain tumors, squamous cell carcinoma of the lung, head and neck squamous cell carcinoma and was described as a potential DNA methylation for cervical cancer (Cheon et al., 2014; Chen et al., 2014d; Vachani et al., 2007; Liu et al., 2010; Seong et al., 2012; Hogan et al., 2011).

CYFIP1 was shown to be down-regulated during invasion of epithelial tumors (Silva et al., 2009). CYFIP1 down-regulation is associated with poor prognosis in epithelial tumors (Silva et al., 2009).

CYP2S1 was shown to regulate colorectal cancer growth in the cell line HCT116 through association with PGE2-mediated activation of ß-catenin signaling (Yang et al., 2015b). CYP2S1 was described as being up-regulated in multiple epithelial-derived cancers and in hypoxic tumor cells (Nishida et al., 2010; Madanayake et al., 2013). CYP2S1 depletion in bronchial epithelial cell lines was shown to result in altered regulation in key pathways implicated in cell proliferation and migration such as the mTOR signal pathway (Madanayake et al., 2013). CYP2S1 depletion was shown to be associated with drug sensitivity in colorectal and breast cancer (Tan et al., 2011). CYP2S1 was shown to be correlated with survival in breast cancer and is associated with poor prognosis in colorectal cancer (Murray et al., 2010; Kumarakulasingham et al., 2005). CYP2S1 was shown to metabolize BaP-7,8-diol into the highly mutagenic and carcinogenic benzo[a]pyrene-r-7,t-8-dihydrodiol-t-9, 10-epoxide and thus may play an important role in benzo[a]pyrene-induced carcinogenesis (Bui et al., 2009). CYP2S1 was shown to be significantly up-regulated in ovarian cancer metastasis compared with primary ovarian cancer (Downie et al., 2005).

DES expression in colorectal cancer stroma was shown to be correlated with advanced stage disease (Arentz et al., 2011). DES was shown to be up-regulated in colorectal cancer (Ma et al., 2009). DES was shown to be associated with severity and differentiation of colorectal cancer and a decreased survival rate (Ma et al., 2009). DES was described as a potential oncofetal serum tumor marker for colorectal cancer (Ma et al., 2009). DES was shown to be a specific marker for rhabdomyosarcoma (Altmannsberger et al., 1985). DES was described as one of three members of a protein panel that may be potentially useful for staging of bladder carcinoma by using immunohistochemistry (Council and Hameed, 2009).

DIS3 was shown to be frequently mutated in multiple myeloma and recurrently mutated in acute myeloid leukemia (Ding et al., 2012; Lohr et al., 2014). DIS3 mutations in multiple myeloma were shown to be associated with shorter median overall survival. Mutations in minor subclones were shown to be associated with worse response to therapy compared to patients with DIS3 mutations in the major subclone (Weissbach et al., 2015). DIS3 was shown to be up-regulated in colorectal carcinomas through a 13q gain. Silencing of DIS3 was shown to affect important tumorigenic characteristics such as viability, migration and invasion. Thus, DIS3 may be a novel candidate oncogene contributing to colorectal cancer progression (de Groen et al., 2014). DIS3 was described as part of a gene panel which may be used in combination with plasma protein based biomarkers to allow earlier diagnosis of epithelial ovarian cancer (Pits et al., 2013). DIS3 may be a potential candidate gene for breast cancer susceptibility since numerous polymorphisms were detected upon mutation screening in breast cancer families (Rozenblum et al., 2002).

EEF1A1 was shown to be up-regulated in a variety of cancer entities, including colorectal cancer, ovarian cancer, gastric cancer, prostate cancer, glioblastoma and squamous cell carcinoma and was described as potential serum biomarker for prostate cancer (Lim et al., 2011; Qi et al., 2005; Matassa et al., 2013; Vui-Kee et al., 2012; Kuramitsu et al., 2010; Kido et al., 2010; Scrideli et al., 2008; Rehman et al., 2012). Mechanistically, EEF1A1 inhibits apoptosis through an interaction with p53 and p73, promotes proliferation by transcriptional repression of the cell cycle inhibitor p21 and participates in the regulation of epithelial-mesenchymal transition (Blanch et al., 2013; Choi et al., 2009; Hussey et al., 2011).

EEF1A2 was described as being up-regulated in breast cancer, ovarian cancer, lung cancer, pancreatic cancer, gastric cancer, prostate cancer and TFE3 translocation renal cell carcinoma (Pflueger et al., 2013; Sun et al., 2014; Yang et al., 2015c; Zang et al., 2015; Abbas et al., 2015). EEF1A2 was shown to be associated with poor prognosis in ovarian cancer, gastric cancer, pancreatic ductal adenocarcinoma and lung adenocarcinoma (Duanmin et al., 2013; Yang et al., 2015c; Li et al., 2006; Lee and Surh, 2009). EEF1A2 was described as being associated with oncogenesis since it stimulates the phospholipid signaling and activates the Akt-dependent cell migration and actin remodeling, which ultimately favors tumorigenesis (Abbas et al., 2015). EEF1A2 was described to inhibit p53 function in hepatocellular carcinoma via PI3K/AKT/mTOR-dependent stabilization of MDM4. Strong activation of the EEF1A2/PI3K/AKT/mTOR/MDM4 signaling pathway was shown to be associated with short survival in hepatocellular carcinoma and thus may be a target for therapy in a subset of patients (Longerich, 2014). EEF1A2 was shown to be associated with TNM stage, invasiveness and survival in pancreatic cancer patients. Thus, EEF1A2 might be a potential target for treatment of pancreatic cancer (Zang et al., 2015). EEF1A2 was shown to be associated with prostate cancer development through promotion of proliferation and inhibition of apoptosis and thus might serve as a potential therapeutic target in prostate cancer (Sun et al., 2014). EEF1A2 was shown to interact with the tumor suppressor protein p16, which leads to down-regulation of EEF1A2 and is associated with inhibition of cancer cell growth (Lee et al., 2013). EEF1A2 was show to be associated with nodal metastasis and perineural invasion in pancreatic ductal adenocarcinoma (Duanmin et al., 2013). EEF1A2 was shown to be associated with survival in breast cancer (Kulkarni et al., 2007). EEF1A2 was described as a putative oncogene and tumor suppressor gene in lung adenocarcinoma cell lines and in ovarian cancer (Lee, 2003; Zhu et al., 2007a).

EIF2S1 was described as a promoter of tumor progression and resistance to therapy upon phosphorylation. However, EIF2S1 was also described to be implicated in suppressive effects on tumorigenesis (Zheng et al., 2014). EIF2S1 was described as a downstream effector of mTOR which decreases survival of cancer cells upon excessive phosphorylation and thus may serve as a target for drug development (Tuval-Kochen et al., 2013).

EIF4G2 was described as one gene of a set of core genes that were shown to be associated with the elimination of tumor formation of pediatric glioma CD133+ cells (Baxter et al., 2014). EIF4G2 was shown to be associated with repression of diffuse large B cell lymphoma development upon down-regulation through miR-520c-3p (Mazan-Mamczarz et al., 2014). EIF4G2 was shown to facilitate protein synthesis and cell proliferation by modulating the synthesis of cell cycle proteins (Lee and McCormick, 2006). EIF4G2 was shown to be down-regulated in bladder tumors and down-regulation was associated with invasive tumors (Buim et al., 2005). EIF4G2 was described as being involved in MycN/IFNgamma-induced apoptosis and both viability and death of neuroblastoma cells (Wittke et al., 2001).

F7 in complex with tissue factor was described as being aberrantly expressed on the surface of cancer cells, including ovarian cancer. The complex was further described as being associated with the induction of malignant phenotypes in ovarian cancer (Koizume and Miyagi, 2015). The F7-tissue factor complex pathway was described as a mediator of breast cancer progression which may stimulate the expression of numerous malignant phenotypes in breast cancer cells. Thus, the F7-tissue factor pathway is a potentially attractive target for breast cancer treatment (Koizume and Miyagi, 2014). F7 was shown to be regulated by the androgen receptor in breast cancer (Naderi, 2015). F7 was shown to be associated with the regulation of autophagy via mTOR signaling in hepatocellular carcinoma cell lines (Chen et al., 2014a). F7 was shown to be associated with tumor invasion and metastasis in colorectal cancer and ovarian cancer (Tang et al., 2010; Koizume et al., 2006). F7 was shown to be ectopically up-regulated in colorectal cancer (Tang et al., 2009). F7 in complex with the tissue factor was shown to be associated with chemotherapy resistance in neuoblastoma (Fang et al., 2008a).

FAM115C is up-regulated upon hypoxia in non-small cell lung cancer (Leithner et al., 2014).

FAM83A was described as a potential biomarker for lung cancer (Li et al., 2005). FAM83A was described as a marker gene which can be used in a panel with NPY1R and KRT19 to detect circulating cancer cells in breast cancer patients (Liu et al., 2014d). FAM83A ablation from breast cancer cells was shown to result in diminished MAPK signaling with marked suppression of growth in vitro and tumorigenicity in vivo (Cipriano et al., 2014). Furthermore, the FAM83 protein family was described as a novel family of oncogenes which regulates MAPK signaling in cancer and thus is suitable for the development of cancer therapies that aim at suppressing MAPK signaling (Cipriano et al., 2014). FAM83A was shown to be associated with trastuzumab resistance in HER2-positive breast cancer cell lines (Boyer et al., 2013). In general, FAM83A was shown to be a candidate gene associated with EGFR-tyrosine kinase inhibitor resistance in breast cancer (Lee et al., 2012). FAM83A was described as being associated with poor prognosis in breast cancer (Lee et al., 2012). FAM83A was shown to be up-regulated in non-small cell lung cancer (Qu et al., 2010). FAM83A was shown to be a potential specific and sensitive marker to detect circulating tumor cell in the peripheral blood of non-small cell lung cancer patients (Qu et al., 2010).

Up-regulation of FAM83D affects the proliferation and invasion of hepatocellular carcinoma cells (Wang et al., 2015a; Liao et al., 2015b). FAM83D is significantly elevated in breast cancer cell lines and in primary human breast cancers (Wang et al., 2013b).

FAT1 was described as being significantly mutated in squamous-cell cancer of the head and neck, frequently mutated in cervical adenocarcinoma, bladder cancer, early T-cell precursor acute lymphoblastic leukemia, fludarabine refractoriness chronic lymphocytic leukemia, glioblastoma and colorectal cancer and mutated in esophageal squamous cell carcinoma (Gao et al., 2014; Neumann et al., 2013; Morris et al., 2013; Messina et al., 2014; Mountzios et al., 2014; Cazier et al., 2014; Chung et al., 2015). FAT1 was described as being repressed in oral cancer and preferentially down-regulated in invasive breast cancer (Katoh, 2012). FAT1 was described as being up-regulated in leukemia which is associated with a poor prognosis in preB-acute lymphoblastic leukemia (Katoh, 2012). FAT1 was shown to be up-regulated in pancreatic adenocarcinoma and hepatocellular carcinoma (Valletta et al., 2014; Wojtalewicz et al., 2014). FAT1 was described to suppress tumor growth via activation of Hippo signaling and to promote tumor migration via induction of actin polymerization (Katoh, 2012). FAT1 was shown to be a candidate cancer driver gene in cutaneous squamous cell carcinoma (Pickering et al., 2014). FAT1 was described as a tumor suppressor which is associated with Wnt signaling and tumorigenesis (Morris et al., 2013).

Depending on its subcellular localization, filamin A plays a dual role in cancer: In the cytoplasm, filamin A functions in various growth signaling pathways, in addition to being involved in cell migration and adhesion pathways. Thus, its over-expression has a tumor-promoting effect. In contrast to full-length filamin A, the C-terminal fragment, which is released upon proteolysis of the protein, localizes to the nucleus, where it interacts with transcription factors and thereby suppresses tumor growth and metastasis (Savoy and Ghosh, 2013).

A tumor-specific C-terminal truncation of GBP5 was described as being potentially responsible for the dysregulation of GBP5 in lymphoma cells (Wehner and Herrmann, 2010). GBP5 was described to possess possible cancer-related functions because of the restricted expression pattern of the three GBP5 splice variants in cutaneous T-cell lymphoma tumor tissues and cell lines as well as in melanoma cell lines (Fellenberg et al., 2004).

GJB5 was shown to be down-regulated in non-small cell lung cancer cell lines, larynx cancer and head and neck squamous cell carcinomas (Zhang et al., 2012; Broghammer et al., 2004; Al Moustafa et al., 2002). GJB5 was described to act as a tumor suppressor in non-small cell lung cancer cell lines through inhibition of cell proliferation and metastasis (Zhang et al., 2012). GJB5 was shown to be up-regulated in sessile serrated adenomas/polyps, premalignant lesions that may account for 20-30% of colon cancers (Delker et al., 2014). GJB5 expression was described as significantly altered during skin tumor promotion and progression in a mouse model (Slaga et al., 1996).

GLS was described as being indirectly regulated by the MYC oncogene in order to increase glutamine metabolism in cancer cells (Dang et al., 2009). GLS was shown to be suppressed by the tumor suppressor NDRG2 in colorectal cancer (Xu et al., 2015). GLS was described as being up-regulated in pancreatic ductal adenocarcinomas, triple-negative breast cancer, hepatocellular carcinoma, oral squamous cell carcinoma, colorectal cancer and malignant glia-derived tumors (van Geldermalsen et al., 2015; Szeliga et al., 2014; Huang et al., 2014a; Cetindis et al., 2015; Yu et al., 2015a; Chakrabarti et al., 2015). GLS was shown to be associated with survival in hepatocellular carcinoma and was also described as a sensitive and specific biomarker for pathological diagnosis and prognosis of hepatocellular carcinoma (Yu et al., 2015a). Loss of one copy of GLS was shown to blunt tumor progression in an immune-competent MYC-mediated mouse model of hepatocellular carcinoma (Xiang et al., 2015). GLS was shown to be required for tumorigenesis and inhibition of tumor-specific GLS was described as a potential approach for cancer therapy (Xiang et al., 2015). GLS was shown to be associated with Taxol-resistance in breast cancer (Fu et al., 2015a). GLS over-expression was shown to be highly correlated with tumor stage and progression in prostate cancer patients (Pan et al., 2015). GLS expression was shown to be associated with deeper tumor infiltration and pathological patterns of tubular adenocarcinoma in colon cancer tumorigenesis. GLS may serve as a target for colorectal cancer therapy (Huang et al., 2014a). Silencing of the GLS isoenzyme KGA was shown to result in lower survival ratios in the glioma cell lines SFxL and LN229 (Martin-Rufian et al., 2014). Silencing of GLS in the glioma cell lines SFxL and LN229 was also shown to result in induction of apoptosis by evoking lower c-myc and bcl-2 expression, as well as higher pro-apoptotic bid expression (Martin-Rufian et al., 2014). ErbB2 activation was shown to up-regulate GLS expression via the NF-kB pathway, which promoted breast cancer cell proliferation (Qie et al., 2014). Knock-down or inhibition of GLS in breast cancer cells with high GLS levels was shown to result in significantly decreased proliferation (Qie et al., 2014).

GNA15 was shown to be up-regulated in primary and metastatic small intestinal neuroendocrine neoplasias (Zanini et al., 2015). Increased expression of GNA15 was shown to be associated with a poorer survival, suggesting that GNA15 may have a pathobiological role in small intestinal neuroendocrine neoplasias and thus could be a potential therapeutic target (Zanini et al., 2015). GNA15 was described as being down-regulated in many non-small cell lung cancer cell lines (Avasarala et al., 2013). High expression of GNA15 in normal karyotype acute myeloid leukemia was shown to be associated with a significant poorer overall survival (de Jonge et al., 2011). GNA15 was shown to be a critical downstream effector of non-canonical Wnt signaling and a regulator of non-small cell lung cancer cell proliferation and anchorage-independent cell growth. Thus, GNA15 is a potential therapeutic target for the treatment of non-small cell lung cancer (Avasarala et al., 2013). GNA15 was shown to be associated with tumorigenic signaling in pancreatic carcinoma (Giovinazzo et al., 2013). GNA15 was shown to stimulate STAT3 via a c-Src/JAK- and ERK-dependent mechanism upon constitutive activation in human embryonic kidney 293 cells (Lo et al., 2003).

HAS3 under-expression was shown to be associated with advanced tumor stage, nodal metastasis, vascular invasion and poorer disease-specific survival and metastasis-free survival in urothelial carcinoma of the upper urinary tract and the urinary bladder (Chang et al., 2015). Thus, HAS3 may serve as a prospective prognostic biomarker and a novel therapeutic target in urothelial carcinomas (Chang et al., 2015). HAS3 was shown to favor pancreatic cancer growth by hyaluronan accumulation (Kultti et al., 2014). HAS3 inhibition was shown to decrease viability in the colorectal adenocarcinoma cell line SW620 (Heffler et al., 2013). HAS3 inhibition was shown to be associated with differential expression of several genes involved in the regulation of SW620 colorectal tumor cell survival (Heffler et al., 2013). HAS3 was shown to be associated with the mediation of colon cancer growth by inhibiting apoptosis (Teng et al., 2011). HAS3 was shown to be up-regulated in esophageal squamous cell carcinoma, adenocarcinomas and squamous cell carcinomas of the lung and nodular basal cell carcinoma (Tzellos et al., 2011; Twarock et al., 2011; de Sa et al., 2013). HAS3 was described as an independent prognostic factor in breast cancer since HAS3 expression in stromal cells of breast cancer patients was shown to be correlated with a high relapse rate and short overall survival (Auvinen et al., 2014). HAS3 was shown to be associated with serous ovarian carcinoma, renal clear cell carcinoma, endometrioid endometrial carcinoma and osteosarcoma (Nykopp et al., 2010; Weiss et al., 2012; Cai et al., 2011; Tofuku et al., 2006).

HIF1A was shown to be associated with tumor necrosis in aggressive endometrial cancer. HIF1A was further described to be a potential target for the treatment of this disease (Bredholt et al., 2015). HIF1A was shown to be associated with hepatocarcinogenesis, sarcoma metastasis and nasopharyngeal carcinoma (Chen et al., 2014c; El-Naggar et al., 2015; Li et al., 2015b). A single nucleotide polymorphism in HIF1A was shown to be significantly associated with clinical outcomes of aggressive hepatocellular carcinoma patients after surgery (Guo et al., 2015). Aberrant HIF1A activity together with aberrant STAT3 activity was shown to drive tumor progression in malignant peripheral nerve sheath tumor cell lines. Thus, inhibition of the STAT3/HIF1A/VEGF-A signaling axis was described as a viable treatment strategy (Rad et al., 2015). HIF1A was described as an important target for hypoxia-driven drug resistance in multiple myeloma (Maiso et al., 2015). HIF1A was shown to be asymmetrical expressed in three different cell lines that correspond with the stages of multiple myeloma pathogenesis, suggesting that HIF1A is involved in the tumorigenesis and metastasis of multiple myeloma (Zhao et al., 2014b). The long noncoding HIF1A antisense RNA-2 was described as being up-regulated in non-papillary clear-cell renal carcinomas and gastric cancer and is associated with tumor cell proliferation and poor prognosis in gastric cancer (Chen et al., 2015b). De-regulation of the PI3K/AKT/mTOR pathway through HIF1A was described to be critical for quiescence, maintenance and survival of prostate cancer stem cells (Marhold et al., 2015). HIF1A was described as one gene of a 4-gene classifier which is prognostic for stage I lung adenocarcinoma (Okayama et al., 2014). A polymorphism of HIF1A was shown to be associated with increased susceptibility to digestive tract cancer in Asian populations (Xu et al., 2014). HIF1A was described as a prognostic marker in sporadic male breast cancer (Deb et al., 2014).

The activity of intracellular HYOU1 protein has been shown to provide a survival benefit in cancer cells during tumor progression or metastasis. The extracellular HYOU1 protein plays an essential role in the generation of an anti-tumor immune response by facilitating the delivery of tumor antigens for their cross-presentation (Fu and Lee, 2006; Wang et al., 2014). HYOU1 protein has been introduced in cancer immunotherapy and showed a positive immunomodulating effect (Yu et al., 2013; Chen et al., 2013; Yuan et al., 2012; Wang and Subjeck, 2013).

A study has shown that IGHG1 was over-expressed in human pancreatic cancer tissues compared to adjacent non-cancerous tissues. On the contrary, the IGHG1 protein was down-regulated in infiltrating ductal carcinomas tissues (Kabbage et al., 2008; Li et al., 2011). siRNA targeted silencing of IGHG1 was able to inhibit cell viability and promote apoptosis (Pan et al., 2013).

Researchers have observed expression of IGHG3 in Saudi females affected by breast cancer. Similarly, gains in copy number as well as elevated levels of IGHG3 were detected in African American men suffering from prostate cancer. Another report showed that IGHG3 expression is found in squamous non-small cell lung cancers, malignant mesothelioma as well as on tumor cells that are sporadically seen in MALT lymphomas and that show a propensity for differentiation into plasma cells (Remmelink et al., 2005; Bin Amer et al., 2008; Ledet et al., 2013; Zhang et al., 2013; Sugimoto et al., 2014).

IGHG4 encodes immunoglobulin heavy constant gamma 4 (G4m marker) and is located on chromosome 14q32.33 (RefSeq, 2002). Recent work has detected rearrangements involving IGHG4 in primary testicular diffuse large B cell lymphoma (Twa et al., 2015). IGHM encodes immunoglobulin heavy constant mu (RefSeq, 2002). Studies have observed down-regulation of IGHM in Chinese patients affected by rhabdomyosarcoma. Others have detected expression of IGHM in diffuse large B-cell lymphoma. Another group has found that in diffuse large B-cell lymphoma the IGHM gene is conserved only on the productive IGH allele in most IgM+ tumors. In addition, epithelioid angiomyolipoma samples did not show any reactivity for transcription factor binding to IGHM enhancer 3 or transcription factor EB (Kato et al., 2009; Blenk et al., 2007; Ruminy et al., 2011; Liu et al., 2014b).

IL36RN was described as a marker which can significantly distinguish stage III from stages I and II in lung adenocarcinoma (Liang et al., 2015).

Reduced expression of INA was shown to be associated with metastases, recurrence and shorter overall survival in pancreatic neuroendocrine tumors. Thus, INA may be a useful prognostic biomarker for pancreatic neuroendocrine tumor aggressiveness (Liu et al., 2014a). INA was described as being up-regulated in oligodendroglia phenotype gliomas and INA expression was shown to be correlated with progression-free survival of oligodendrogliomas and glioblastomas (Suh et al., 2013). INA was described as a marker for neuroblastoma which is useful for the differential diagnostic work-up of small round cell tumors of childhood (Willoughby et al., 2008).

ITGA6 expression is up-regulated in different cancer entities including breast, prostate, colon and gastric cancer and is associated with tumor progression and cell invasion (Mimori et al., 1997; Lo et al., 2012; Haraguchi et al., 2013; Rabinovitz et al., 1995; Rabinovitz and Mercurio, 1996). The proliferative effects of the Abeta4 variant of ITGA6 appear to be mediated through the Wnt/beta-catenin pathway (Groulx et al., 2014). The Abeta4 variant of ITGA6 leads to the VEGF-dependent activation of the PI3K/Akt/mTOR pathway. This pathway plays an important role in the survival of metastatic carcinoma cells (Chung et al., 2002).

KRT14 was highly expressed in various squamous cell carcinomas such as esophageal, lung, larynx, uterine cervical as well as in adenomatoid odontogenic tumor. However, it was absent in small cell carcinoma of the urinary bladder and weak in lung adenocarcinoma, gastric adenocarcinoma, colorectal adenocarcinoma, hepatocellular carcinoma, pancreatic ductal adenocarcinoma, breast infiltrating dutal adenocarcinoma, thyroid papillary carcinoma and uterine endometrioid adenocarcinoma (Xue et al., 2010; Terada, 2012; Vasca et al., 2014; Hammam et al., 2014; Shruthi et al., 2014). In bladder cancer, KRT14 expression was strongly associated with poor survival (Volkmer et al., 2012).

Over-expression of KRT16 was found in basal-like breast cancer cell lines as well as in carcinoma in situ. Others did not find significant difference in immunohistochemical expression of KRT16 between non-recurrent ameloblastomas and recurrent ameloblastomas (Joosse et al., 2012; Ida-Yonemochi et al., 2012; Safadi et al., 2016). In addition, in silico analyses showed correlation between KRT16 expression and shorter relapse-free survival in metastatic breast cancer (Joosse et al., 2012).

KRT5 was shown to be up-regulated in breast cancers of young women (Johnson et al., 2015). KRT5 was shown to be associated with inferior disease-free survival in breast cancer in young women and with unfavorable clinical outcome in premenopausal patients with hormone receptor-positive breast cancer (Johnson et al., 2015; Sato et al., 2014). KRT5 was shown to be regulated by the tumor suppressor BRCA1 in the breast cancer cell lines HCC1937 and T47D (Gorski et al., 2010). KRT5 was shown to be de-regulated in malignant pleural mesothelioma (Melaiu et al., 2015). KRT5 was described as a diagnostic mesothelial marker for malignant mesothelioma (Arif and Husain, 2015). KRT5 was shown to be correlated with the progression of endometrial cancer (Zhao et al., 2013). KRT5 was shown to be mutated and down-regulated in invasive tumor areas in a patient with verrucous carcinoma (Schumann et al., 2012). KRT5 was shown to be part of a four-protein panel which was differentially expressed in colorectal cancer biopsies compared to normal tissue samples (Yang et al., 2012). KRT5 and three other proteins of the four-protein panel were described as novel markers and potential targets for treatment for colorectal cancer (Yang et al., 2012). KRT5 was described as being associated with basal cell carcinoma (Depianto et al., 2010). KRT5 was described as a candidate to identify urothelial carcinoma stem cells (Hatina and Schulz, 2012).

Activation of the kynurenine pathway, in which KYNU is involved, was shown to be significantly higher in glioblastoma and suggests the involvement of the kynurenine pathway in glioma pathophysiology (Adams et al., 2014). KYNU was described as cancer-linked gene whose expression was altered upon aryl hydrocarbon receptor knockdown in the MDA-MB-231 breast cancer cell line (Goode et al., 2014). KNYU was shown to be differentially expressed in high and non-aggressive osteosarcoma cell lines, suggesting that it might have an important role in the process of osteosarcoma tumorigenesis. Thus, KYNU might also represent a candidate for a future therapeutic targets (Lauvrak et al., 2013). KYNU was shown to be associated with the re-expression of tumorigenicity in non-tumorigenic HeLa and human skin fibroblast hybrid cells. Thus, KYNU may provide an interesting candidate for the regulation of tumorigenic expression (Tsujimoto et al., 1999).

Transcription analysis of LAMB3 in combination with two other genes was shown to be useful in the diagnosis of papillary thyroid carcinoma and prediction of lymph node metastasis risk (Barros-Filho et al., 2015). LAMB3 was shown to be associated with the cancer entities of oral squamous cell carcinoma, prostate cancer, gastric cancer, colorectal cancer, ewing family tumors, lung carcinoma, breast carcinoma and ovarian carcinoma (Volpi et al., 2011; Ii et al., 2011; Reis et al., 2013; Stull et al., 2005; Irifune et al., 2005; Tanis et al., 2014). LAMB3 was shown to be up-regulated in cervical squamous cell carcinoma, lung cancer, gastric cancer, nasopharyngeal carcinoma and esophageal squamous cell carcinoma (Kwon et al., 2011; Wang et al., 2013a; Yamamoto et al., 2013; Kita et al., 2009; Fang et al., 2008b). LAMB3 was described as a protein known to influence cell differentiation, migration, adhesion, proliferation and survival and which functions as an oncogene in cervical squamous cell carcinoma (Yamamoto et al., 2013). Knock-down of LAMB3 was shown to suppress lung cancer cell invasion and metastasis in vitro and in vivo. Thus, LAMB3 is a key gene which plays an important role in the occurrence and metastasis of lung cancer (Wang et al., 2013a). LAMB3 was shown to be regulated by the tumor suppressor miR-218 in head and neck squamous cell carcinoma (Kinoshita et al., 2012). Silencing of LAMB3 in head and neck squamous cell carcinoma was shown to result in inhibition of cell migration and invasion (Kinoshita et al., 2012). LAMB3 expression was shown to be correlated with the depth of invasion and venous invasion in esophageal squamous cell carcinoma (Kita et al., 2009). Methylation of LAMB3 was shown to be correlated with several parameters of poor prognosis in bladder cancer (Sathyanarayana et al., 2004).

Inhibition of LAP3 was shown to result in suppressed invasion in the ovarian cancer cell line ES-2 through down-regulation of fascin and MMP-2/9. Thus, LAP3 may act as a potential anti-metastasis therapeutic target (Wang et al., 2015d). High expression of LAP3 was shown to be correlated with grade of malignancy and poor prognosis of glioma patients (He et al., 2015). LAP3 was shown to promote glioma progression by regulating cell growth, migration and invasion and thus might be a new prognostic factor (He et al., 2015). Frameshift mutations in genes involved in amino acid metabolism including LAP3 were detected in microsatellite instability-high gastric and colorectal cancer (Oh et al., 2014). LAP3 was shown to be up-regulated in hepatocellular carcinoma, esophageal squamous cell carcinoma and prostate cancer (Zhang et al., 2014; Tian et al., 2014; Lexander et al., 2005). LAP3 was shown to promote hepatocellular carcinoma cells proliferation by regulating G1/S checkpoint in cell cycle and advanced cells migration (Tian et al., 2014). Expression of LAP3 was further shown to be correlated with prognosis and malignant development of hepatocellular carcinoma (Tian et al., 2014). Silencing of LAP3 in the esophageal squamous cell carcinoma cell line ECA109 was shown to reduce cell proliferation and colony formation while LAP3 knock-down resulted in cell cycle arrest (Zhang et al., 2014). Over-expression of LAP3 in the esophageal squamous cell carcinoma cell line TE1 was shown to favor cell proliferation and invasiveness (Zhang et al., 2014). Thus, LAP3 was shown to play a role in the malignant development of esophageal squamous cell carcinoma (Zhang et al., 2014).

Researchers have reported expression of M6PR in colon carcinoma cell lines as well as in choriocarcinoma cells (Braulke et al., 1992; O'Gorman et al., 2002). In breast cancer, low-level expression of M6PR was associated with poor patient prognosis (Esseghir et al., 2006). Furthermore, over-expression of M6PR resulted in a decreased cellular growth rate in vitro and decreased tumor growth in nude mice (O'Gorman et al., 2002).

MAPK6 was shown to play a role in regulating cell morphology and migration in the breast cancer cell line MDA-MB-231 (Al-Mandi et al., 2015). MAPK6 was described as a part of the cancer-associated MAPK signaling pathway, being associated with BRAF and MEK1/2 signaling in melanoma (Lei et al., 2014; Hoeflich et al., 2006). MAPK6 was shown to be up-regulated in lung carcinoma, gastric cancer and oral cancer (Long et al., 2012; Rai et al., 2004; Liang et al., 2005a). MAPK6 was shown to promote lung cancer cell invasiveness by phosphorylating the oncogene SRC-3. Thus, MAPK6 may be an attractive target for therapeutic treatment of invasive lung cancer (Long et al., 2012). MAPK6 was described as a potential target for the anti-cancer drug development against drug resistant breast cancer cells (Yang et al., 2010). Over-expression of MAPK6 in gastric carcinomas was shown to be correlated with TNM staging, serosa invasion and lymph node involvement (Liang et al., 2005a). MAPK6 was shown to be a binding partner of the core cell cycle machinery component cyclin D3, suggesting that MAPK6 has a potential activity in cell proliferation (Sun et al., 2006).

MNAT1 was shown to be associated with poor prognosis in estrogen receptor-positive/HER2-negative breast cancer (Santarpia et al., 2013). Loss of intrinsic fragmentation of MNAT1 during granulopoiesis was shown to promote the growth and metastasis of leukemic myeloblasts (Lou et al., 2013). MNAT1 was shown to be dys-regulated in the ovarian cancer cell line OAW42 upon knock-down of the putative oncogene ADRM1 (Fejzo et al., 2013). MNAT1 gene silencing mediated by siRNA was shown to suppress cell growth of the pancreatic cancer cell line BxPC3 in vitro, and significantly achieved an anti-tumor effect on a subcutaneously transplanted pancreatic tumor in vivo (Liu et al., 2007a). Genetic variants in MNAT1 were described to be associated with the susceptibility of lung cancer (Li et al., 2007). Infection of the pancreatic cancer cell line BxPC3 with a recombinant adenovirus encoding antisense MNAT1 was shown to result in decreased expression of MNAT1 and an increased proportion of G0/G1 phase cells. Thus, MNAT1 is suggested to play an important role in the regulation of cell cycle G1 to S transition in the pancreatic cancer cell line BxPC3 (Zhang et al., 2005). MNAT1-modulated cyclin-dependent kinase-activating kinase activity was shown to cross-regulate neuroblastoma cell G1 arrest and is crucial in the switch from proliferation to differentiation in neuroblastoma cells (Zhang et al., 2004).

DNA methylation-associated silencing of NEFH in breast cancer was shown to be frequent, cancer-specific, and correlated with clinical features of disease progression (Calmon et al., 2015). NEFH was further described to be inactivated through DNA methylation in pancreatic, gastric and colon cancer and thus might contribute to the progression of these malignancies as well (Calmon et al., 2015). NEFH CpG island methylation was shown to be associated with advanced disease, distant metastasis and prognosis in renal cell carcinoma (Dubrowinskaja et al., 2014). Thus, NEFH methylation could be a candidate epigenetic marker for the prognosis of renal cell carcinoma (Dubrowinskaja et al., 2014). NEFH was shown to be up-regulated in extraskeletal myxoid chondrosarcoma of the vulva (Dotlic et al., 2014). Over-expression of NEFH in a hepatocellular carcinoma cell line was shown to reduce cell proliferation while knock-down of NEFH promoted cell invasion and migration in vitro, and increased the ability to form tumors in mice. Thus, NEFH functions as a tumor suppressor in hepatocellular carcinoma (Revill et al., 2013). NEFH was shown to be frequently methylated in Ewing sarcoma and thus might be associated with tumorigenesis (Alholle et al., 2013).

DNA methylation-mediated silencing of NEFL was shown to be a frequent event in breast cancer that may contribute to the progression of breast cancer and possibly other malignancies such as pancreatic, gastric and colon cancer (Calmon et al., 2015). NEFL was described as a potential tumor suppressor gene which is associated with the cancer of several organs (Huang et al., 2014c). NEFL was described to potentially play a role in cancer cell apoptosis and invasion in head and neck squamous cell carcinoma cell lines (Huang et al., 2014c). NEFL methylation was described as a novel mechanism that conferred cisplatin chemoresistance in head and neck cancer cell lines through interaction with the mTOR signaling pathway (Chen et al., 2012). NEFL was described as a candidate biomarker predictive of chemotherapeutic response and survival in patients with head and neck cancer (Chen et al., 2012). High expression of NEFL was described to be correlated with better clinical outcome in supratentorial ependymoma (Nagel et al., 2013). NEFL was shown to be ectopically expressed in breast cancer and decreased in primary breast cancers with lymph node metastases compared to cancers with negative lymph nodes (Li et al., 2012). Low expression of NEFL was shown to indicate poor five-year disease-free survival for early-stage breast cancer patients and thus could be a potential prognostic factor for early-stage breast cancer patients (Li et al., 2012). NEFL was shown to be down-regulated in glioblastoma multiforme (Khalil, 2007). Allelic deletion at chromosome 8p21-23, where NEFL is located, was described as an early and frequent event in the carcinogenesis and development of lung cancer and was also described to be associated with breast cancer, prostate cancer and hepatitis B virus-positive hepatocellular carcinoma (Seitz et al., 2000; Becker et al., 1996; Haggman et al., 1997; Kurimoto et al., 2001).

NEFM was described as a gene with relevance to tumor progression and association with the processes involved in metastasis (Singh et al., 2015). NEFM was shown to be hypo-methylated and up-regulated in esophageal cancer (Singh et al., 2015). NEFM was described as a candidate tumor suppressor gene that is frequently down-regulated in glioblastoma (Lee et al., 2015a). DNA methylation-associated silencing of NEFM in breast cancer was shown to be frequent, cancer-specific, and correlated with clinical features of disease progression (Calmon et al., 2015). NEFM was further described to be inactivated through DNA methylation in pancreatic, gastric and colon cancer and thus might contribute to the progression of these malignancies as well (Calmon et al., 2015). NEFM was shown to be associated with prostate cancer and astrocytomas (Wu et al., 2010; Penney et al., 2015). NEFM was described as a novel candidate tumor suppressor gene which was shown to be methylated in renal cell carcinoma (Ricketts et al., 2013). Methylation of NEFM was shown to be associated with prognosis in renal cell carcinoma (Ricketts et al., 2013). NEFM was described as a potential diagnostic marker which was shown to be differentially expressed in neuroendocrine tumor cell lines compared to non-neuroendocrine tumor cell lines (Hofsli et al., 2008).

NUP155 was described as a potential epigenetic biomarker of white blood cell's DNA which is associated with breast cancer predisposition (Khakpour et al., 2015). NUP155 was described as strictly required for the proliferation and survival of NUP214-ABL1-positive T-cell acute lymphoblastic leukemia cells and thus constitutes a potential drug target in this disease (De et al., 2014).

OAS2 was shown to be associated with impairment of the CD3-zeta chain expression through caspase-3 activation. Deficiency of the CD3-zeta chain was described to be often observed in oral cancer (Dar et al., 2015). OAS2 was described to be involved in a sub-pathway of the advanced prostate cancer risk-associated innate immunity and inflammation pathway (Kazma et al., 2012). Sub-pathway analysis revealed that OAS2 is nominally associated with advanced prostate cancer risk (Kazma et al., 2012).

Lower expression of PABPN1 in non-small cell lung cancer was shown to be correlated with a poor prognosis (Ichinose et al., 2014). Loss of PABPN1 was described to potentially promote tumor aggressiveness by releasing cancer cells from microRNA-mediated gene regulation in non-small cell lung cancer (Ichinose et al., 2014). A N-terminal polyalanine expansion mutant of PABPN1 was shown to be associated with induction of apoptosis via the p53 pathway in the HeLa and HEK-293 cell lines (Bhattacharjee et al., 2012).

PCBP1 was described to be central to cancer stem cells enrichment and functionality in prostate cancer cells (Chen et al., 2015a). PCBP1 was described as an inhibitor of gastric cancer pathogenesis whose down-regulation is associated with the malignant phenotype in both cultured and xenograft gastric cancer cells (Zhang et al., 2015e). Based on the differential expression between benign and malignant serum and tissue samples, respectively, in patients with serous adenocarcinoma of the ovary, PCBP1 was suggested to play a role in ovarian cancer pathophysiology (Wegdam et al., 2014). PCBP1 was shown to be an important mediator of TGF-ß-induced epithelial-mesenchymal transition, a prerequisite for tumor metastasis, in the gall bladder carcinoma cell line GBC-SD (Zhang and Dou, 2014). PCBP1 expression levels were shown to regulate the capacity of the gall bladder carcinoma cell line GBC-SD to migrate and invade in vitro (Zhang and Dou, 2014). Thus, PCBP1 might be a potential prognostic marker for gall bladder carcinoma metastasis (Zhang and Dou, 2014). PCBP1 down-regulation was described as being potentially involved with cervical cancer pathogenesis (Pathak et al., 2014). PCBP1 was described as a regulator of the tumor suppression-associated transcription factor p63 (Cho et al., 2013). High expression of PCBP1 in complete hydatidiform moles was shown to be associated with lower risk of progression to gestational trophoblastic tumors, while PCBP1 expression was significantly lower in malignant transformed moles (Shi et al., 2012). Thus, PCBP1 was suggested to play an important role in the pathogenesis of gestational trophoblastic tumors (Shi et al., 2012). Over-expression of PCBP1 was shown to result in suppression of the translation of the metastasis associated PRL-3 protein and inactivation of AKT whereas knock-down of PCBP1 was shown to cause activation of AKT and promotion of tumorigenesis (Wang et al., 2010). PCBP1 was described to play a negative role in tumor invasion in the hepatoma cell line HepG2 (Zhang et al., 2010). Loss of PCBP1 in human hepatic tumor was described to contribute to the formation of a metastatic phenotype (Zhang et al., 2010).

PDPN was described to be up-regulated in squamous cell carcinomas, mesotheliomas, glioblastomas and osteosarcomas (Fujita and Takagi, 2012). PDPN was described as a regulator of tumor invasion and metastasis since PDPN is associated with several pathways which participate in epithelial-to-mesenchymal transition, collective-cell migration, platelet activation, aggregation, and lymphangiogenesis (Dang et al., 2014). PDPN was described as a marker in oral carcinogenesis and epithelioid mesotheliomas (Swain et al., 2014; Ordonez, 2005). PDPN up-regulation was described to be associated with lymph node metastasis and poor prognosis in squamous cell carcinoma of the upper aerodigestive tract (Chuang et al., 2013). PDPN was described to be expressed in vascular tumors, malignant mesothelioma, tumors of the central nervous system, germ cell tumors, squamous cell carcinomas and aggressive tumors with higher invasive and metastatic potential (Raica et al., 2008). Thus, PDPN might be considered as an attractive therapeutic target for tumor cells (Raica et al., 2008).

PHTF2 was shown to be down-regulated in lingual squamous cell carcinoma (Huang et al., 2007).

PKM2 was shown to be crucial for cancer cell proliferation and tumor growth (Chen et al., 2014b; Li et al., 2014; DeLaBarre et al., 2014). N-myc acts as a transcriptional regulator for PKM2 in medulloblastoma (Tech et al., 2015). PKM2 seems to play a role in hepatocarcinogenesis, epithelial mesenchymal transition, and angiogenesis (Nakao et al., 2014). PKM2 is one of the two key factors of the Warburg effect in oncology (Tamada et al., 2012; Warner et al., 2014; Ng et al., 2015). Expression of PKM2 is up-regulated in cancer cells (Chaneton and Gottlieb, 2012; Luo and Semenza, 2012; Wu and Le, 2013). In malignant cells PKM2 functions in glycolysis, as a transcriptional coactivator and as a protein kinase. In the latter function it translocates to the nucleus and phosphorylates histone 3 which finally causes the progress of the cell cycle in glioblastomas (Semenza, 2011; Luo and Semenza, 2012; Tamada et al., 2012; Venneti and Thompson, 2013; Yang and Lu, 2013; Gupta et al., 2014; Iqbal et al., 2014; Chen et al., 2014b; Warner et al., 2014). The low-activity-dimeric PKM2 might play a role in cancer instead of the active tetrameric form (Mazurek, 2011; Wong et al., 2015; Iqbal et al., 2014; Mazurek, 2007).

PKP1 was shown to be down-regulated in prostate cancer and esophageal adenocarcinoma (Kaz et al., 2012; Yang et al., 2015a). Knock-down of PKP1 in the non-neoplastic, prostatic BPH-1 cell line led to reduced apoptosis and differential expression of genes such as the prostate cancer-associated SPOCK1 gene (Yang et al., 2015a). Collectively, altered expression of PKP1 and SPOCK1 appears to be frequent and critical event in prostate cancer and PKP1 is suggested to have a tumor-suppressive function (Yang et al., 2015a). Reduced expression of PKP1 was shown to be associated with significantly shorter time to onset of distant metastasis in oral cavity squamous cell carcinoma (Harris et al., 2015). PKP1 loss through promoter methylation was described to be associated with the progression of Barrett's esophagus to esophageal adenocarcinoma (Kaz et al., 2012). PKP1 was shown to be up-regulated in non-small cell lung cancer and may be a good marker to distinguish squamous-cell carcinomas samples (Sanchez-Palencia et al., 2011). PKP1 was shown to be up-regulated in the well-differentiated liposarcoma cell line GOT3 (Persson et al., 2008). Decreased PKP1 expression was described to promote increased motility in head and neck squamous cell carcinoma cells (Sobolik-Delmaire et al., 2007). PKP1 loss was shown to be associated with cervical carcinogenesis (Schmitt-Graeff et al., 2007). PKP1 was shown to be associated with local recurrences or metastases as well as poor survival in patients with squamous cell carcinoma of the oropharynx (Papagerakis et al., 2003).

Increased PKP3 mRNA in the blood of gastrointestinal cancer patients can be used as a biomarker and predictor for disease outcome (Valladares-Ayerbes et al., 2010). Over-expression of PKP3 was correlated with a poor outcome in breast, lung and prostate cancer, whereas down-regulation in bladder cancer is linked to invasive behavior (Furukawa et al., 2005; Breuninger et al., 2010; Demirag et al., 2012; Takahashi et al., 2012). Loss of PKP3 leads to increased protein levels of MMP7 and PRL3, which are required for cell migration and tumor formation (Khapare et al., 2012; Basu et al., 2015).

Knock-down of PPP4R1 was shown to suppress cell proliferation in the breast cancer cell line ZR-75-30 (Qi et al., 2015). Thus, PPP4R1 could promote breast cancer cell proliferation and might play a vital role in breast cancer occurrence (Qi et al., 2015). Knock-down of PPP4R1 in the hepatocellular carcinoma cell line HepG2 was shown to result in decreased cell proliferation, colony formation and cell cycle arrest at G2/M (Wu et al., 2015). Knock-down of PPP4R1 was further shown to lead to the inactivation of the p38 and c-Jun N-terminal kinase signaling cascades in HepG2 cells, which indicates that PPP4R1 could promote cell proliferation (Wu et al., 2015). Thus, PPP4R1 plays a crucial role in promoting hepatocellular carcinoma cell growth (Wu et al., 2015). PPP4R1 was described as a negative regulator of inhibitor of NF-kB kinase activity in lymphocytes whose down-regulation promotes oncogenic NF-kB signaling in a subgroup of T cell lymphomas (Brechmann et al., 2012).

PRC1 was described to be associated with radioresistance in cervical cancer since cervical cancer tissues showed a high differential expression of PRC1 after radiation (Fu et al., 2015b). A genetic loci in intron 14 of PRC1 was described to be associated with breast cancer susceptibility (Cai et al., 2014). PRC1 was described as one gene of a five-gene signature which could be proposed as a prognostic signature for disease free survival of breast cancer patients (Mustacchi et al., 2013). PRC1 was shown to be up-regulated in ovarian carcinoma, cervical cancer and bladder cancer (Espinosa et al., 2013; Ehrlichova et al., 2013; Kanehira et al., 2007). PRC1 was shown to be up-regulated during the 4-hydroxy-estradiol-mediated malignant transformation of the mammary epithelial cell line MCF-10A (Okoh et al., 2013). PRC1 was described as a gene with significant biological implications in tumor pathogenesis which can be used in a gene-set to predict the prognosis of resectable patients with non-small cell lung cancer upon adjuvant chemotherapy (Tang et al., 2013). PRC1 was suggested to be negatively regulated by the cell cycle associated kinase Plk1 (Hu et al., 2012). Knock-down of PRC1 in the bladder cancer cell line NIH3T3 was shown to result in a significant increase of multinuclear cells and subsequent cell death (Kanehira et al., 2007). Furthermore, PRC1 was shown to interact with the novel cancer-testis antigen MPHOSPH1 in bladder cancer cells and the MPHOSPH1/PRC1 complex was suggested to play a crucial role in bladder carcinogenesis and could be a novel therapeutic target (Kanehira et al., 2007). PRC1 was shown to be regulated by p53 (Li et al., 2004).

Expressed sequence tag profiling identified PRDM15 as an up-regulated gene in lymphomas (Giallourakis et al., 2013). PRDM15 was described as a candidate tumor suppressor gene which may contribute to the development or progression of pancreatic cancer (Bashyam et al., 2005).

Distinct polymorphisms in PTHLH were shown to be associated with lung cancer risk and prognosis (Manenti et al., 2000). Up-regulation of PTHLH in a C57BL/6-mouse-derived model of spontaneously metastatic mammary cancer was described as potentially being involved in metastatic dissemination of breast cancer (Johnstone et al., 2015). PTHLH was shown to be up-regulated in oral squamous cell carcinoma, chondroid neoplasms, adult T-cell leukemia/lymphoma and clear cell renal cell carcinomas (Bellon et al., 2013; Yang et al., 2013a; Yao et al., 2014; Lv et al., 2014). PTHLH up-regulation was shown to be associated with poor pathologic differentiation and poor prognosis in patients with head and neck squamous cell carcinoma (Lv et al., 2014). PTHLH was shown to be up-regulated through p38 MAPK signaling, which contributes to colon cancer cell extravasation of the lung by caspase-independent death in endothelial cells of the lung microsvasculature (Urosevic et al., 2014). PTHLH was shown to be significantly differentially expressed in squamous cell carcinoma compared with normal skin (Prasad et al., 2014). PTHLH was described as a part of a four-gene signature associated with survival among patients with early-stage non-small cell lung cancer (Chang et al., 2012). Disruption of anti-proliferative function by frameshift mutations of PTHLH was described to contribute to the development of early colorectal cancer in patients with hereditary non-polyposis colorectal cancer (Yamaguchi et al., 2006). PTHLH up-regulation was shown to be associated with poor outcome both in overall survival and disease-free survival for clear cell renal cell carcinoma patients who underwent nephrectomy (Yao et al., 2014). PTHLH was shown to positively modulate cell cycle progression and to change the expression of proteins involved in cell cycle regulation via ERK1/2, p38, MAPK, and PI3K signaling pathways in the colorectal adenocarcinoma cell line Caco-2 (Calvo et al., 2014).

RAP1GDS1 was shown to promote proliferation of pancreatic cancer cells (Schuld et al., 2014). Simultaneous loss of two splice variants of RAP1GDS1 in non-small cell lung carcinoma cell line NCI-H1703 xenografts in mice was shown to result in decreased tumorigenesis (Schuld et al., 2014). RAP1GDS1 was shown to promote cell cycle progression in multiple types of cancer, making it a valuable target for cancer therapeutics (Schuld et al., 2014). RAP1GDS1 was shown to be up-regulated in breast cancer, prostate cancer and non-small cell lung carcinoma (Hauser et al., 2014; Tew et al., 2008; Zhi et al., 2009). The SmgGDS-558 splice variant of RAP1GDS1 was shown to be a unique promoter of RhoA and NF-kB activity which plays a functional role in breast cancer malignancy (Hauser et al., 2014). High RAP1GDS1 expression was shown to be associated with worse clinical outcome in breast cancer (Hauser et al., 2014). RAP1GDS1 was shown to regulate cell proliferation, migration, and NF-kappaB transcriptional activity in non-small cell lung cancer, therefore promoting the malignant phenotype of this disease. Thus, RAP1GDS1 is an intriguing therapeutic target in non-small cell lung cancer (Tew et al., 2008). RAP1GDS1 was shown to be fused to NUP98 in T-cell acute lymphoblastic leukemia (Romana et al., 2006).

RNPEP activity was shown to be up-regulated in colorectal adenomas, papillary thyroid carcinoma, breast cancer and clear cell renal cell carcinoma (Ramirez-Exposito et al., 2012; Larrinaga et al., 2013; Perez et al., 2015; Varona et al., 2007). RNPEP was shown to be associated with the tumor growth of rat C6 gliomas implanted at the subcutaneous region (Mayas et al., 2012).

RORA was described as a potential lung cancer oncogene (Wang et al., 2015e). RORA was shown to be associated with the expression of the potential tumor suppressor gene OPCML in colon cancer (Li et al., 2015a). Two single nucleotide polymorphisms in RORA were shown to be associated with breast cancer (Truong et al., 2014). RORA was described as a potential tumor suppressor and therapeutic target for breast cancer (Du and Xu, 2012). RORA was shown to be down-regulated in colorectal adenocarcinomas and breast cancer (Kottorou et al., 2012; Du and Xu, 2012). Stable over-expression of RORA in the hepatoma cell line HepG2 was shown to influence the expression of genes involved in glucose metabolism and liver carcinogenesis, indicating an association of RORA with the carcinogenesis within cells of hepatic origin (Chauvet et al., 2011). RORA was shown to be differentially methylated in gastric cancer compared to normal gastric mucosa (Watanabe et al., 2009). RORA was described to be associated with the control of cell growth and differentiation, and with the control of metastatic behavior in the androgen-independent prostate cancer cell line DU 145 (Moretti et al., 2002).

RPS17 was shown to be differentially expressed in metastatic uveal melanoma in normal whole blood and tissues prone to metastatic involvement by uveal melanoma, suggesting that RPS17 might play a role in tropism of uveal melanoma metastasis (Demirci et al., 2013). RPS17 was shown to be up-regulated in hepatocellular carcinoma (Liu et al., 2007b).

Knock-down of RPS26 was shown to induce p53 stabilization and activation, resulting in p53-dependent cell growth inhibition (Cui et al., 2014). RPS26 was further shown to play a role in DNA damage response by directly influencing p53 transcriptional activity (Cui et al., 2014).

S100A2 was shown to be associated with non-small cell lung cancer and was described as a predictive marker for poor overall survival in lung squamous carcinoma patients (Hountis et al., 2014; Zhang et al., 2015d). S100A2 was described as a down-stream target of the oncogene KRAS and a promoter of tumor progression in lung cancer (Woo et al., 2015). S100A2 was described as a promising marker for the prediction of overall survival in pancreatic ductal adenocarcinoma (Jamieson et al., 2011). Altered expression of S100A2 through nitrosamine N-nitrosopyrrolidone was described as a potential reason for the tumor progression of squamous cell carcinomas of the esophagus among black South Africans (Pillay et al., 2015). S100A2 was shown to be up-regulated in the early stage of non-small cell lung cancer, in plasma of nasopharyngeal carcinoma patients, laryngeal cancer, gastric cancer and epidermal tumors (Zhu et al., 2013a; Lin et al., 2013; Zhang et al., 2015a; Zha et al., 2015; Wang et al., 2015c). Methylation-associated inactivation of S100A2 was shown to be frequent in head and neck and bladder cancer, and thus may be an important event in the tumorigenesis of these diseases (Lee et al., 2015c). S100A2 cytoplasmic expression was shown to be up-regulated in oral squamous cell carcinoma, while the nuclear expression was down-regulated (Kumar et al., 2015). Cytoplasmic up-regulation of S100A2 was shown to be a potential predictor of recurrence risk in oral squamous cell carcinoma patients (Kumar et al., 2015). S100A2 was described to play a role in the metastasis of mammary carcinomas (Naba et al., 2014). S100A2 was shown to be a BRCA1/p63 co-regulated tumor suppressor gene which plays a role in the regulation of mutant p53 stability by modulating the binding of mutant p53 to HSP90 (Buckley et al., 2014). S100A2 was described as a candidate tumor suppressor gene which is down-regulated in recurrent nasopharyngeal cancer, and thus may play an important role in the occurrence of recurrent nasopharyngeal cancer (Huang et al., 2014b). S100A2 was shown to be down-regulated in gastric cancer and down-regulation was shown to be associated with advanced depth of invasion, lymph node metastasis, decreased relapse-free probability, and decreased overall survival (Liu et al., 2014e). Thus, S100A2 down-regulation may be a negative independent prognostic biomarker for gastric cancer (Liu et al., 2014e). S100A2 was further shown to negatively regulate the MEK/ERK signaling pathway in MGC-803 cancer cells (Liu et al., 2014e). Over-expression of S100A2 was shown to induce epithelial-mesenchymal transition in A549 lung cancer cells followed by increased invasion and enhanced Akt phosphorylation and increased tumor growth in immunocompromised mice (Naz et al., 2014). Protumorigenic actions of S100A2 were further described to involve regulation of PI3/Akt signaling and functional interaction with the TGF beta signaling way protein Smad3 (Naz et al., 2014). Expression of S100A2 was shown to be correlated with histological grade, lymph node metastasis, clinical stage, and a poor survival rate of patients with perihilar and extra-hepatic cholangiocarcinoma (Sato et al., 2013). Thus, S100A2 may function as a prognostic marker in cholangiocarcinoma patients (Sato et al., 2013).

S100A8 was described as an important mediator in acute and chronic inflammation which interacts with myeloid-derived suppressor cells in a positive feedback loop to promote tumor development and metastasis (Zheng et al., 2015). S100A8 was described as a potential diagnostic biomarker, prognostic indicator and therapeutic target in non-small cell lung cancer (Lim and Thomas, 2013). Over-expression of S100A8 was shown to be associated with stage progression, invasion, metastasis and poor survival in bladder cancer (Yao et al., 2007). S100A8 was shown to be a diagnostic marker for invasive bladder carcinoma (Ismail et al., 2015). S100A8 was shown to be up-regulated in anaplastic thyroid carcinoma, giant cell tumor of bone and colorectal cancer (Reeb et al., 2015; Zhang et al., 2015b; Liao et al., 2015a). In vivo analysis in mice using anaplastic thyroid carcinoma cells with S100A8 knock-down revealed reduced tumor growth and lung metastasis, as well as significantly prolonged animal survival (Reeb et al., 2015). S100A8 was shown to promote anaplastic thyroid carcinoma cell proliferation through interaction with RAGE, which activates the p38, ERK1/2 and JNK signaling pathways in tumor cells (Reeb et al., 2015). Thus, S100A8 could represent a relevant therapeutic target in anaplastic thyroid carcinoma (Reeb et al., 2015). S100A8 was shown to be associated with high-risk chronic lymphocytic leukemia (Alsagaby et al., 2014). S100A8 was shown to be associated with kidney cancer progression and was described as a prospective biomarker and therapeutic target for kidney cancer (Mirza et al., 2014). S100A8 was described as a part of calprotectin, which is a heterodimer that is required for the progression of non-inflammation driven liver tumor and might represent a therapeutic target for the treatment of hepatocellular carcinoma (De et al., 2015). S100A8 was shown to regulate colon cancer cell cycle and proliferation by induction of Id3 expression while inhibiting p21 (Zhang et al., 2015b).

SERPINH1 encodes serpin peptidase inhibitor, clade H (heat shock protein 47), member 1, (collagen binding protein 1), a serine proteinase inhibitor. SERPINH1 functions as a collagen-specific molecular chaperone in the endoplasmic reticulum (RefSeq, 2002). SERPINH1 is over-expressed in many human cancers, including stomach cancer, lung cancer, pancreatic ductal adenocarcinoma, glioma, and ulcerative colitis-associated carcinomas (Zhao et al., 2014a). SERPINH1 was shown to be up-regulated in hepatocellular carcinoma, esophageal squamous cell carcinoma, cholangiocellular carcinoma, stomach cancer, lung cancer, pancreatic ductal adenocarcinoma, ulcerative colitis-associated carcinomas and glioma (Zhao et al., 2014a; Padden et al., 2014; Lee et al., 2015b; Naboulsi et al., 2015). Over-expression of SERPINH1 was shown to be associated with poor prognosis in patients with esophageal squamous cell carcinoma and the level of immunostaining of SERPINH1 and pathologic stage were shown to be significantly correlated with overall and recurrence-free survival (Lee et al., 2015b). Thus, SERPINH1 may be a potential prognostic biomarker for esophageal squamous cell carcinoma (Lee et al., 2015b). Knock-down of SERPINH1 in glioma cells was shown to inhibit glioma cell growth, migration and invasion in vitro while SERPINH1 knock-down in vivo was shown to inhibit tumor growth and induced apoptosis (Zhao et al., 2014a). Thus, SERPINH1 could be a therapeutic target for the treatment of glioma (Zhao et al., 2014a). SERPINH1 was shown to be down-regulated in metastases compared to the primary tumor of oral squamous cell carcinomas with multiple lymph node involvement, indicating that SERPINH1 might be associated with the metastatic potential of these tumors (Nikitakis et al., 2003).

SLC7A11 was shown to be down-regulated in drug resistant variants of the W1 ovarian cancer cell line and thus might play a role in cancer cell drug resistance (Januchowski et al., 2013). SLC7A11 was described to modulate tumor microenvironment, leading to a growth advantage for cancer (Savaskan and Eyupoglu, 2010). SLC7A11 was described to be involved in neurodegenerative processes in glioma, setting SLC7A11 a potential prime target for cancer therapy (Savaskan et al., 2015). SLC7A11 was shown to be repressed by p53 in the context of ferroptosis, and the p53-SLC7A11 axis was described as preserved in the p53 (3KR) mutant, and contributes to its ability to suppress tumorigenesis in the absence of the classical tumor suppression mechanisms (Jiang et al., 2015). SLC7A11 was described as the functional subunit of system Xc- whose function is increased in aggressive breast cancer cells (Linher-Melville et al., 2015). High membrane staining for SLC7A11 in cisplatin-resistant bladder cancer was shown to be associated with a poorer clinical outcome and SLC7A11 inhibition was described as a promising therapeutic approach to the treatment of this disease (Drayton et al., 2014). SLC7A11 was shown to be differentially expressed in the human promyelocytic leukemia cell line HL-60 that had been exposed to benzene and its metabolites and thus highlights a potential association of SLC7A11 with leukemogenesis (Sarma et al., 2011). Disruption of SLC7A11 was described to result in growth inhibition of a variety of carcinomas, including lymphoma, glioma, prostate and breast cancer (Chen et al., 2009). Inhibition of SLC7A11 was shown to inhibit cell invasion in the esophageal cancer cell line KYSE150 in vitro and its experimental metastasis in nude mice and thus establishes a role of SLC7A11 in tumor metastasis (Chen et al., 2009).

SRPR was shown to be amplified in a case of acute myeloid leukemia with double minute chromosomes (Crossen et al., 1999).

The human ortholog of SSR4 was shown to be differentially expressed in the opossum melanoma cell lines TD6b and TD15L2 and up-regulated in tumors of advanced stages, implicating SSR4 as a candidate gene with potential functions that might be associated with ultraviolet-induced melanomagenesis and metastasis (Wang and VandeBerg, 2004). The mRNA level of SSR4 was shown to be enriched in the osteosarcoma cell lines OHS, SaOS-2 and KPDXM compared to normal osteoblast cells (Olstad et al., 2003).

De-regulated expression of STK17A is associated with different cancer types. Decreased expression in cervical and colorectal cancer is related to the pro-apoptotic character of STK17A connected with tumor progression. STK17A in glioblastoma and head and neck cancer is over-expressed in a grade-dependent manner, maybe caused through the influence on other tumor relevant pathways like TGF-beta (Mao et al., 2013; Thomas et al., 2013; Park et al., 2015; Bandres et al., 2004). STK17A is a direct target of the tumor suppressor gene p53 and a modulator of reactive oxygen species (ROS) (Kerley-Hamilton et al., 2005; Mao et al., 2011).

SYK was described as a modulator of tumorigenesis which acts as a tumor promoter, by providing a survival function, in some cells and as a tumor suppressor, by restricting epithelial-mesenchymal transition and inhibiting migration, in others (Krisenko and Geahlen, 2015). SYK was described as being associated with B-cell receptor (BCR) activation in B-cell lymphomas (Seda and Mraz, 2015). Inhibition of key kinases of the BCR pathway such as SYK have been found in preclinical models to decrease chronic lymphocytic leukemia cell viability (Davids and Brown, 2012). SYK was shown to be up-regulated in chronic lymphocytic leukemia (Feng and Wang, 2014). SYK was described as being associated with the pathogenesis of chronic lymphocytic leukemia and might have a value in evaluating the effect of therapy and the prognosis of this disease (Feng and Wang, 2014). SYK was described as a potential tumor suppressor in breast cancer whose absence in primary breast tumors is correlated with poor outcomes (Navara, 2004). SYK was shown to play a critical role in paclitaxel resistance in ovarian cancer (Yu et al., 2015b). SYK down-regulation was described as being associated with the development of various cancers, including colorectal cancer (Peng et al., 2015). Distinct polymorphisms in the SYK promoter were shown to be independent risk factor for colorectal cancer development in Han Chinese in Southern China (Peng et al., 2015). SYK was shown to be frequently methylated in hepatocellular carcinoma and SYK methylation has been demonstrated to identify a subset of hepatocellular carcinoma cases with poor prognosis (Shin et al., 2014).

TP63 translocation was described as an event in a subset of anaplastic lymphoma kinase-positive anaplastic large cell lymphomas which is associated with an aggressive course of the disease (Hapgood and Savage, 2015). TP63 was described to play a complex role in cancer due to its involvement in epithelial differentiation, cell cycle arrest and apoptosis (Lin et al., 2015). The TP63 isoform TAp63 was described to be over-expressed in hematological malignancies while TP63 missense mutations have been reported in squamous cancers and TP63 translocations in lymphomas and some lung adenocarcinomas (Orzol et al., 2015). Aberrant splicing resulting in the over-expression of the TP63 isoform DeltaNp63 was described to be frequently found in human cancers such as cutaneous squamous cell carcinoma, where it is likely to favor tumor initiation and progression (Missero and Antonini, 2014; Inoue and Fry, 2014).

TPM1 was shown to be down-regulated in renal cell carcinoma, a squamous cell carcinoma of esophagus cell line, metastatic canine mammary carcinomas and neuroblastoma cell lines (Klopfleisch et al., 2010; Yager et al., 2003; Zare et al., 2012; Wang et al., 2015b). TPM1 expression was shown to be associated with tumor size, Fuhrman grade and the prognosis of renal cell carcinoma patients. TPM1 transfection of renal cell carcinoma cell lines OSRC-2 and 786-0 was shown to reduce migratory and invasive abilities, while enhancing apoptosis (Wang et al., 2015b). Thus, TPM1 was described to exhibit characteristics of a tumor suppressor gene while being over-expressed in renal cell carcinoma cells (Wang et al., 2015b). RAS/PI3K/AKT and RAS/MEK/ERK signaling pathways were described to be involved in TPM1 regulation and suppression in the intrahepatic cholangiocarcinoma cell line HuCCT1, as well as in a cell line of squamous carcinoma of the esophagus (Zare et al., 2012; Yang et al., 2013b). TPM1 was described as a tumor suppressor whose over-expression in the breast cancer cell line MCF-7 suppressed anchorage-independent cell growth (Zhu et al., 2007b). Epigenetic suppression of TPM1 was described to be associated with altered TGF-beta tumor suppressor function and might contribute to metastatic properties of tumor cells (Varga et al., 2005).

Tryptase was shown to be up-regulated in certain patients with acute myeloid leukemia (Jin et al., 2014). Expression of tryptase was described to be regulated by SCF/C-KIT signaling via the ERK1/2 and p38MAPK pathways (Jin et al., 2014). Mast cell tryptase was described to be involved in colorectal cancer angiogenesis and was shown to be higher expressed in the serum of colorectal cancer patients before than after radical surgical resection (Ammendola et al., 2014).

TSHZ3 was shown to be down-regulated in the oral squamous cell carcinoma cell line SCC-9 compared to the non-tumorigenic cell line OKF6-TERT1R (Marcinkiewicz and Gudas, 2014). TSHZ3 was described as a transcriptional regulator gene which was found to be recurrently rearranged in several cases of high-grade serous ovarian cancers (McBride et al., 2012). TSHZ3 was described as a candidate tumor suppressor gene with down-regulated expression in breast and prostate cancers (Yamamoto et al., 2011).

TSPAN10 was shown to be a differentially expressed gene between metastatic melanoma samples and normal skin samples which may be a potential biomarker for metastatic melanoma therapy (Liu et al., 2014c). Among other genes, TSPAN10 was shown to be up-regulated in uterine leiomyosarcoma metastases compared to primary leiomyosarcomas and is therefore contributing to the differentiation of these conditions and may aid in understanding tumor progression in this cancer (Davidson et al., 2014).

TTPAL was described as a candidate oncogene which displayed mutations in micro-satellite-instable colorectal cancers (Tuupanen et al., 2014).

TUBGCP2 was shown to be up-regulated in a taxol-resistant ovarian cancer cell line and was described to be associated with the sensitization of the non-small cell lung carcinoma cell line NCI-H1155 to taxol (Huang and Chao, 2015). TUBGCP2 was shown to be up-regulated in glioblastoma, where its over-expression antagonized the inhibitory effect of the CDK5 regulatory subunit-associated tumor suppressor protein 3 on DNA damage G2/M checkpoint activity (Draberova et al., 2015).

VIM was described as a down-stream target of STAT3 which is associated with breast tumor progression upon de-regulation through STAT3 (Banerjee and Resat, 2015). VIM was described as a potential nasopharyngeal carcinoma-related protein (Chen et al., 2015c). A negative methylation status of vimentin was shown to predict improved prognosis in pancreatic cancer patients (Zhou et al., 2014). VIM was shown to be up-regulated through C6orf106 in non-small cell lung cancer and was described to be subsequently associated with enhanced cancer cell invasion (Zhang et al., 2015c). VIM was described as an independent predictor for overall survival of squamous cell lung carcinoma patients (Che et al., 2015). VIM was described as a biomarker that can potentially distinguish melanoma subtypes and might predict melanoma aggressiveness in different subgroups of melanoma (Qendro et al., 2014). VIM was shown to be up-regulated in clear cell renal cell carcinoma (Shi et al., 2015). High expression of VIM was described as an independent prognostic indicator for clear cell renal cell carcinoma (Shi et al., 2015). VIM was shown to act as a scaffold to recruit Slug to ERK and to promote Slug phosphorylation, which was described as a requirement of the initiation of the epithelial-mesenchymal transition, a developmental process adopted during tumorigenesis that promotes metastatic capacity (Virtakoivu et al., 2015).

WDR1 was shown to be up-regulated in the interstitial fluid from ovarian carcinomas and in high-grade canine cutaneous mast cell tumors with poor prognosis compared to low-grade mast cell tumors with good prognosis (Schlieben et al., 2012; Haslene-Hox et al., 2013). WDR1 was shown to be down-regulated in chemoresistant advanced serous epithelial ovarian carcinoma (Kim et al., 2011). WDR1 down-regulation in chemoresistant advanced serous epithelial ovarian carcinoma was shown to be correlated with poor overall survival (Kim et al., 2011). WDR1 was shown to be up-regulated in the region between the invading tumor front and normal tissues (interface zone) in breast cancer and thus may be related to progression and metastasis of breast carcinomas (Kang et al., 2010).

YWHAE fusion with NUTM2B/NUTM2E was described as an event which was observed in a minority of clear cell sarcomas of the kidney (Karlsson et al., 2015). The YWHAE-NUTM2 fusion was described as a frequent event in high-grade endometrial stromal sarcomas (Ali et al., 2014). High-grade endometrial stromal sarcomas with the YWHAE-NUTM2 fusion were described as a subset of endometrial stromal sarcomas with an aggressive clinical behavior and poor prognosis (Kruse et al., 2014). Breakages at three loci including YWHAE were described as potential contributors to the development of uterine angiosarcoma (Suzuki et al., 2014). YWHAE was shown to be down-regulated in gastric cancer and reduced YWHAE levels were associated with diffuse-type gastric cancer and early-onset of this pathology, indicating that YWHAE may have a role in the gastric carcinogenesis process (Leal et al., 2012). YWHAE was shown to be differentially expressed in tissues of breast cancer patients with and without relapse and was shown to be associated with both disease-free and overall survival (Cimino et al., 2008). Thus, YWHAE might be used as an independent prognostic marker and a potential drug target for breast cancer (Cimino et al., 2008).

Changes in ZNF292 were described as chronic lymphocytic leukemia driver alterations (Puente et al., 2015). ZNF292 was described as a tumor-suppressor gene in colorectal cancer (Takeda et al., 2015). ZNF292 was described as an immunogenic antigen with clinical relevance in head and neck squamous cell carcinoma (Heubeck et al., 2013).

DETAILED DESCRIPTION OF THE INVENTION

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

As used herein and except as noted otherwise all terms are defined as given below.

The term "T-cell response" means the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, 13, or 14 or longer, and in case of MHC class II peptides (elongated variants of the peptides of the invention) they can be as long as 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 5

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1-Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |
| A*24 | South America | 20% |
| A*24 | Europe | 18% |

The peptides of the invention, preferably when included into a vaccine of the invention as described herein bind to A*02. A vaccine may also include pan-binding MHC class II peptides. Therefore, the vaccine of the invention can be used to treat cancer in patients that are A*02 positive, whereas no selection for MHC class II allotypes is necessary due to the pan-binding nature of these peptides.

If A*02 peptides of the invention are combined with peptides binding to another allele, for example A*24, a higher percentage of any patient population can be treated compared with addressing either MHC class I allele alone. While in most populations less than 50% of patients could be addressed by either allele alone, a vaccine comprising HLA-A*24 and HLA-A*02 epitopes can treat at least 60% of patients in any relevant population. Specifically, the following percentages of patients will be positive for at least one of these alleles in various regions: USA 61%, Western Europe 62%, China 75%, South Korea 77%, Japan 86% (calculated from www.allelefrequencies.net).

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

$$\text{percent identity} = 100[1-(C/R)]$$

wherein C is the number of differences between the Reference Sequence and the Compared Sequence over the length of alignment between the Reference Sequence and the Compared Sequence, wherein
(i) each base or amino acid in the Reference Sequence that does not have a corresponding aligned base or amino acid in the Compared Sequence and
(ii) each gap in the Reference Sequence and
(iii) each aligned base or amino acid in the Reference Sequence that is different from an aligned base or amino acid in the Compared Sequence, constitutes a difference and
(iiii) the alignment has to start at position 1 of the aligned sequences;
and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity, then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 93 or a variant thereof which is 88% homologous to SEQ ID NO: 1 to SEQ ID NO: 93, or a variant thereof that will induce T cells cross-reacting with said peptide. The peptides of the invention have the ability to bind to a molecule of the human major histocompatibility complex (MHC) class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 93. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO: 93, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly nonconservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or -II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or —II is substantially changed, or is negatively affected, when compared to the non-modified peptide.

The amino acid residues that do not substantially contribute to interactions with the T-cell receptor can be modified by replacement with other amino acids whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 6

Variants and motif of the peptides according to SEQ ID NO: 4, 9, and 18

| | Position | | | | | | | | | |
|---|---|---|---|---|---|---|---|---|---|---|
| | 1 | 2 | 3 | 4 | 5 | 6 | 7 | 8 | 9 | 10 |
| SEQ ID No.: 4 | A | L | F | G | T | I | L | E | L | |
| Variants | | | | | | | | | V | |
| | | | | | | | | | I | |
| | | | | | | | | | A | |
| | | M | | | | | | | V | |
| | | M | | | | | | | I | |
| | | M | | | | | | | | |
| | | M | | | | | | | A | |
| | | A | | | | | | | V | |
| | | A | | | | | | | I | |
| | | A | | | | | | | | |
| | | A | | | | | | | A | |
| | | V | | | | | | | V | |
| | | V | | | | | | | I | |
| | | V | | | | | | | | |
| | | V | | | | | | | A | |
| | | T | | | | | | | V | |
| | | T | | | | | | | I | |
| | | T | | | | | | | | |
| | | T | | | | | | | A | |
| | | Q | | | | | | | V | |
| | | Q | | | | | | | I | |
| | | Q | | | | | | | | |
| | | Q | | | | | | | A | |
| SEQ ID No.: 9 | H | L | I | A | E | I | H | T | A | |
| Variants | | | | | | | | | V | |
| | | | | | | | | | I | |
| | | | | | | | | | L | |
| | | M | | | | | | | V | |

TABLE 6-continued

Variants and motif of the peptides according to SEQ ID NO: 4, 9, and 18

| | Position | | | | | | | | | |
|---|---|---|---|---|---|---|---|---|---|---|
| | 1 | 2 | 3 | 4 | 5 | 6 | 7 | 8 | 9 | 10 |
| | | M | | | | | | | I | |
| | | M | | | | | | | L | |
| | | M | | | | | | | | |
| | | A | | | | | | | V | |
| | | A | | | | | | | I | |
| | | A | | | | | | | L | |
| | | A | | | | | | | | |
| | | V | | | | | | | V | |
| | | V | | | | | | | I | |
| | | V | | | | | | | L | |
| | | V | | | | | | | | |
| | | T | | | | | | | V | |
| | | T | | | | | | | I | |
| | | T | | | | | | | L | |
| | | T | | | | | | | | |
| | | Q | | | | | | | V | |
| | | Q | | | | | | | I | |
| | | Q | | | | | | | L | |
| | | Q | | | | | | | | |
| SEQ ID No.: 18 | F | L | L | D | Q | V | Q | L | G | L |
| Variants | | | | | | | | | | V |
| | | | | | | | | | | I |
| | | | | | | | | | | A |
| | | M | | | | | | | | V |
| | | M | | | | | | | | I |
| | | M | | | | | | | | |
| | | M | | | | | | | | A |
| | | A | | | | | | | | V |
| | | A | | | | | | | | I |
| | | A | | | | | | | | |
| | | A | | | | | | | | A |
| | | V | | | | | | | | V |
| | | V | | | | | | | | I |
| | | V | | | | | | | | |
| | | V | | | | | | | | A |
| | | T | | | | | | | | V |
| | | T | | | | | | | | I |
| | | T | | | | | | | | |
| | | T | | | | | | | | A |
| | | Q | | | | | | | | V |
| | | Q | | | | | | | | I |
| | | Q | | | | | | | | |
| | | Q | | | | | | | | A |

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 7.

TABLE 7

Combinations of the elongations of peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |

TABLE 7-continued

| Combinations of the elongations of peptides of the invention | |
|---|---|
| 0 | 0 or 1 or 2 or 3 or 4 |
| N-terminus | C-terminus |
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 pM, and most preferably no more than about 10 pM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 93.

"Consisting essentially of" shall mean that a peptide according to the present invention, in addition to the sequence according to any of SEQ ID NO: 1 to SEQ ID NO: 93 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH=CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxycarbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (www.sigma-aldrich.com) provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly (ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995) (cf. Example 1).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural tumor-associated peptides (TUMAPs)

recorded from esophageal cancer samples (N=16 A*02-positive samples) with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from 16 esophageal cancer patients.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from esophageal cancer tissue samples were purified and HLA-associated peptides were isolated and analyzed by LC-MS (see examples). All TUMAPs contained in the present application were identified with this approach on primary esophageal cancer samples confirming their presentation on primary esophageal cancer.

TUMAPs identified on multiple esophageal cancer and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

In addition to over-presentation of the peptide, mRNA expression of the underlying gene was tested. mRNA data were obtained via RNASeq analyses of normal tissues and cancer tissues (see Example 2). An additional source of normal tissue data was a database of publicly available RNA expression data from around 3000 normal tissue samples (Lonsdale, 2013). Peptides which are derived from proteins whose coding mRNA is highly expressed in cancer tissue, but very low or absent in vital normal tissues, were preferably included in the present invention.

Furthermore, the discovery pipeline XPRESIDENT® v2. allows for a direct absolute quantitation of MHC-, preferably HLA-restricted, peptide levels on cancer or other infected tissues. Briefly, the total cell count was calculated from the total DNA content of the analyzed tissue sample. The total peptide amount for a TUMAP in a tissue sample was measured by nanoLC-MS/MS as the ratio of the natural TUMAP and a known amount of an isotope-labelled version of the TUMAP, the so-called internal standard. The efficiency of TUMAP isolation was determined by spiking peptide:MHC complexes of all selected TUMAPs into the tissue lysate at the earliest possible point of the TUMAP isolation procedure and their detection by nanoLC-MS/MS following completion of the peptide isolation procedure. The total cell count and the amount of total peptide were calculated from triplicate measurements per tissue sample. The peptide-specific isolation efficiencies were calculated as an average from 10 spike experiments each measured as a triplicate (see Example 6 and Table 12).

The present invention provides peptides that are useful in treating cancers/tumors, preferably esophageal cancer that over- or exclusively present the peptides of the invention. These peptides were shown by mass spectrometry to be naturally presented by HLA molecules on primary human esophageal cancer samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy esophagus cells or other normal tissue cells, demonstrating a high degree of tumor association of the source genes (see Example 2). Moreover, the peptides themselves are strongly over-presented on tumor tissue—"tumor tissue" in relation to this invention shall mean a sample from a patient suffering from esophageal cancer, but not on normal tissues (see Example 1).

HLA-bound peptides can be recognized by the immune system, specifically T lymphocytes. T cells can destroy the cells presenting the recognized HLA/peptide complex, e.g. esophageal cancer cells presenting the derived peptides.

The peptides of the present invention have been shown to be capable of stimulating T cell responses and/or are over-presented and thus can be used for the production of antibodies and/or TCRs, such as soluble TCRs, according to the present invention (see Example 3, Example 4). Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The present description further relates to T-cell receptors (TCRs) comprising an alpha chain and a beta chain ("alpha/beta TCRs"). Also provided are HAVCR1-001 peptides capable of binding to TCRs and antibodies when presented by an MHC molecule. The present description also relates to nucleic acids, vectors and host cells for expressing TCRs and peptides of the present description; and methods of using the same.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule. The term also includes so-called gamma/delta TCRs.

In one embodiment the description provides a method of producing a TCR as described herein, the method comprising culturing a host cell capable of expressing the TCR under conditions suitable to promote expression of the TCR.

The description in another aspect relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The alpha and beta chains of alpha/beta TCR's, and the gamma and delta chains of gamma/delta TCRs, are generally regarded as each having two "domains", namely variable and constant domains. The variable domain consists of a concatenation of variable region (V), and joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise the term "TCR delta variable domain" refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

TCRs of the present description preferably bind to an HAVCR1-001 peptide-HLA molecule complex with a binding affinity (KD) of about 100 µM or less, about 50 µM or less, about 25 µM or less, or about 10 µM or less. More preferred are high affinity TCRs having binding affinities of about 1 µM or less, about 100 nM or less, about 50 nM or less, about 25 nM or less. Non-limiting examples of preferred binding affinity ranges for TCRs of the present invention include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity (KD) for an HAVCR1-001 peptide-HLA molecule complex of 100 µM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta heterodimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the non-mutated TCR.

In an embodiment, a TCR comprising at least one mutation in the TCR alpha chain and/or TCR beta chain has a binding affinity for, and/or a binding half-life for, a HAVCR1-001 peptide-HLA molecule complex, which is at least double that of a TCR comprising the non-mutated TCR alpha chain and/or non-mutated TCR beta chain. Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens. It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance, meaning that only T-cells with low-affinity TCRs for self-antigens remain. Therefore, affinity of TCRs or variants of the present description to HAVCR1-001 can be enhanced by methods well known in the art.

The present description further relates to a method of identifying and isolating a TCR according to the present description, said method comprising incubating PBMCs from HLA-A*02-negative healthy donors with A2/HAVCR1-001 monomers, incubating the PBMCs with tetramer-phycoerythrin (PE) and isolating the high avidity T-cells by fluorescence activated cell sorting (FACS)—Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with HAVCR1-001, incubating PBMCs obtained from the transgenic mice with tetramer-phycoerythrin (PE), and isolating the high avidity T-cells by fluorescence activated cell sorting (FACS)—Calibur analysis.

In one aspect, to obtain T-cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient.

In another aspect, to obtain T-cells expressing TCRs of the present description, TCR RNAs are synthesized by techniques known in the art, e.g., in vitro transcription systems. The in vitro-synthesized TCR RNAs are then introduced into primary CD8+ T-cells obtained from healthy donors by electroporation to re-express tumor specific TCR-alpha and/or TCR-beta chains.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1a and the spleen focus-forming virus (SFFV) promoter. In a preferred embodiment, the promoter is heterologous to the nucleic acid being expressed.

In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

The alpha and beta chains of a TCR of the present invention may be encoded by nucleic acids located in separate vectors, or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bi-cistronic constructs in a single vector, which has been shown to be capable of over-coming this obstacle. The use of a viral intra-ribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced. (Schmitt et al. 2009).

Nucleic acids encoding TCRs of the present description may be codon optimized to increase expression from a host cell. Redundancy in the genetic code allows some amino acids to be encoded by more than one codon, but certain codons are less "op-timal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3ζ (CD3ζ fusion). (Schmitt et al. 2009).

In an embodiment, a host cell is engineered to express a TCR of the present description. In preferred embodiments, the host cell is a human T-cell or T-cell progenitor. In some embodiments the T-cell or T-cell progenitor is obtained from a cancer patient. In other embodiments the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutics such as a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993)). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 93, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Saiki et al., 1988).This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of E. coli such as, for example, the E. coli strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 μg and 1.5 mg, preferably 125 μg to 500 μg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMA- TRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonol®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

It is important to realize that the immune response triggered by the vaccine according to the invention attacks the cancer in different cell-stages and different stages of development. Furthermore, different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one Ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example, a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, anti-CD28.

For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed, aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as siRNA into tumor cells.

Aptamers can be selected against complex targets such as cells and tissues and complexes of the peptides comprising, preferably consisting of, a sequence according to any of SEQ ID NO 1 to SEQ ID NO: 93, according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is also regarded as "specific" in the context of the present invention.

The present invention relates to a peptide comprising a sequence that is selected from the group consisting of SEQ ID NO: 1 to SEQ ID NO: 93, or a variant thereof which is at least 88% homologous (preferably identical) to SEQ ID NO: 1 to SEQ ID NO: 93 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 93 or a variant thereof which is at least 88% homologous (preferably identical) to SEQ ID NO: 1 to SEQ ID NO: 93, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 93.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

Another embodiment of the present invention relates to a non-naturally occurring peptide wherein said peptide consists or consists essentially of an amino acid sequence according to SEQ ID No: 1 to SEQ ID No: 48 and has been synthetically produced (e.g. synthesized) as a pharmaceutically acceptable salt. Methods to synthetically produce peptides are well known in the art. The salts of the peptides according to the present invention differ substantially from the peptides in their state(s) in vivo, as the peptides as generated in vivo are no salts. The non-natural salt form of the peptide mediates the solubility of the peptide, in particular in the context of pharmaceutical compositions comprising the peptides, e.g. the peptide vaccines as disclosed herein. A sufficient and at least substantial solubility of the peptide(s) is required in order to efficiently provide the peptides to the subject to be treated. Preferably, the salts are pharmaceutically acceptable salts of the peptides. These salts according to the invention include alkaline and earth alkaline salts such as salts of the Hofmeister series comprising as anions $PO_4^{3-}$, $SO_4^{2-}$, $CH_3COO^-$, $Cl^-$, $Br^-$, $NO_3^-$, $ClO_4^-$, $I^-$, $SCN^-$ and as cations $NH_4^+$, $Rb^+$, $K+$, $Na^+$, $Cs^+$, $Li^+$, $Zn^{2+}$, $Mg^{2+}$, $Ca^{2+}$, $Mn^{2+}$, $Cu^{2+}$ and $Ba^{2+}$. Particularly salts are selected from $(NH_4)_3PO_4$, $(NH_4)_2HPO_4$, $(NH_4)H_2PO_4$, $(NH_4)_2SO_4$, $NH_4CH_3COO$, $NH_4Cl$, $NH_4Br$, $NH_4NO_3$, $NH_4ClO_4$, $NH_4I$, $NH_4SCN$, $Rb_3PO_4$, $Rb_2HPO_4$, $RbH_2PO_4$, $Rb_2SO_4$, $Rb_4CH_3COO$, $Rb_4Cl$, $Rb_4Br$, $Rb_4NO_3$, $Rb_4ClO_4$, $Rb_4I$, $Rb_4SCN$, $K_3PO_4$, $K_2HPO_4$, $KH_2PO_4$, $K_2SO_4$, $KCH_3COO$, $KCl$, $KBr$, $KNO_3$, $KClO_4$, $KI$, $KSCN$, $Na_3PO_4$, $Na_2HPO_4$, $NaH_2PO_4$, $Na_2SO_4$, $NaCH_3COO$, $NaCl$, $NaBr$, $NaNO_3$, $NaClO_4$, $NaI$, $NaSCN$, $ZnCl_2$ $Cs_3PO_4$, $Cs_2HPO_4$, $CsH_2PO_4$, $Cs_2SO_4$, $CsCH_3COO$, $CsCl$, $CsBr$, $CsNO_3$, $CsClO_4$, $CsI$, $CsSCN$, $Li_3PO_4$, $Li_2HPO_4$, $LiH_2PO_4$, $Li_2SO_4$, $LiCH_3COO$, $LiCl$, $LiBr$, $LiNO_3$, $LiClO_4$, $LiI$, $LiSCN$, $Cu_2SO_4$, $Mg_3(PO_4)_2$, $Mg_2HPO_4$, $Mg(H2PO_4)_2$, $Mg_2SO_4$, $Mg(CH_3COO)_2$, $MgCl_2$, $MgBr_2$, $Mg(NO_3)_2$, $Mg(ClO_4)_2$, $MgI_2$, $Mg(SCN)_2$, $MnCl_2$, $Ca_3(PO_4)_2$, $Ca_2HPO_4$, $Ca(H_2PO_4)_2$, $CaSO_4$, $Ca(CH_3COO)_2$, $CaCl_2$, $CaBr_2$, $Ca(NO_3)_2$, $Ca(ClO_4)_2$, $CaI_2$, $Ca(SCN)_2$, $Ba_3(PO_4)_2$, $Ba_2HPO_4$, $Ba(H2PO_4)_2$, $BaSO_4$, $Ba(CH_3COO)_2$, $BaCl_2$, $BaBr_2$, $Ba(NO_3)_2$, $Ba(ClO_4)_2$, $BaI_2$, and $Ba(SCN)_2$. Particularly preferred are NH acetate, $MgCl_2$, $KH_2PO_4$, $Na_2SO_4$, $KCl$, $NaCl$, and $CaCl_2$, such as, for example, the chloride or acetate (trifluoroacetate) salts.

Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitril/water gradient separation.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of esophageal cancer.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, where-in the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 93 or said variant amino acid sequence.

The present invention further relates to activated T cells, produced by the method according to the present invention, wherein said T cells selectively recognizes a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are esophageal cancer cells or other solid or hematological tumor cells such as lung cancer, urinary bladder cancer, ovarian cancer, melanoma, uterine cancer, hepatocellular cancer, renal cell cancer, brain cancer, colorectal cancer, breast cancer, gastric cancer, pancreatic cancer, gallbladder cancer, bile duct cancer, prostate cancer and leukemia.

The present invention further relates to particular marker proteins and biomarkers based on the peptides according to the present invention, herein called "targets" that can be used in the diagnosis and/or prognosis of esophageal cancer. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a esophageal cancer marker (poly)peptide, delivery of a toxin to a esophageal cancer cell expressing a cancer marker gene at an increased level, and/or inhibiting the activity of a esophageal cancer marker polypeptide) according to the invention.

Whenever possible, the antibodies of the invention may be purchased from commercial sources. The antibodies of the invention may also be generated using well-known methods. The skilled artisan will understand that either full length esophageal cancer marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 93 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the esophageal cancer marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')$_2$ fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide.

Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (µg/kg to up to 100 mg/kg of body weight or more per day, depending on the factors mentioned above. Following administration of an antibody, preferably for treating esophageal cancer, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occur in the absence of antibody administration, is an efficacious antibody for treatment of cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Further methods for the production are disclosed in WO 2013/057586A1.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S)) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than 1×10 µM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and *Drosophila* cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive T cells.

If an antigen-presenting cell is transfected to express such an epitope, preferably the cell comprises an expression vector capable of expressing a peptide containing SEQ ID NO: 1 to SEQ ID NO: 93, or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin: streptavidin biochemistry. This system permits the exact control of the MHC density on aAPCs, which allows to selectively elicit high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore, such aAPC-based systems often require the addition of appropriate soluble factors, e. g. cytokines, like interleukin-12.

Allogeneic cells may also be used in the preparation of T cells and a method is described in detail in WO 97/26328, incorporated herein by reference. For example, in addition to *Drosophila* cells and T2 cells, other cells may be used to present antigens such as CHO cells, baculovirus-infected insect cells, bacteria, yeast, vaccinia-infected target cells. In addition, plant viruses may be used (see, for example, Porta et al. (Porta et al., 1994) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO: 93.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to levels of expression in normal (healthy) tissues or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T cell. This engineered T cell can then be transferred to a patient for therapy of cancer.

Any molecule of the invention, i.e. the peptide, nucleic acid, antibody, expression vector, cell, activated T cell, T-cell receptor or the nucleic acid encoding it, is useful for the treatment of disorders, characterized by cells escaping an immune response. Therefore, any molecule of the present invention may be used as medicament or in the manufacture of a medicament. The molecule may be used by itself or combined with other molecule(s) of the invention or (a) known molecule(s).

The present invention is further directed at a kit comprising:
(a) a container containing a pharmaceutical composition as described above, in solution or in lyophilized form;
(b) optionally a second container containing a diluent or reconstituting solution for the lyophilized formulation; and
(c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from esophageal cancer, the medicament of the invention is preferably used to treat esophageal cancer.

The present invention further relates to a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides which were highly overexpressed in the tumor tissue of esophageal cancer patients with various HLA-A HLA-B and HLA-C alleles. It may contain MHC class I and MHC class II peptides or elongated MHC class I peptides. In addition to the tumor associated peptides collected from several esophageal cancer tissues, the warehouse may contain HLA-A*02 and HLA-A*24 marker peptides. These peptides allow comparison of the magnitude of T-cell immunity induced by TUMAPS in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient.

TUMAPs for the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, esophageal cancer samples from patients and blood from healthy donors were analyzed in a stepwise approach:

1. HLA ligands from the malignant material were identified by mass spectrometry
2. Genome-wide messenger ribonucleic acid (mRNA) expression analysis was used to identify genes over-expressed in the malignant tissue (esophageal cancer) compared with a range of normal organs and tissues
3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues.
6. In order to assess, whether an induction of in vivo T-cell responses by the selected peptides may be feasible, in vitro immunogenicity assays were performed using human T cells from healthy donors as well as from esophageal cancer patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients' tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 μm sterile filter. The final bulk solution is obtained.

Final bulk solution is filled into vials and stored at −20° C. until use. One vial contains 700 μL solution, containing 0.578 mg of each peptide. Of this, 500 μL (approx. 400 μg per peptide) will be applied for intradermal injection.

In addition to being useful for treating cancer, the peptides of the present invention are also useful as diagnostics. Since the peptides were generated from esophageal cancer cells and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for esophageal cancer. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The present invention will now be described in the following examples which describe preferred embodiments thereof, and with reference to the accompanying figures, nevertheless, without being limited thereto. For the purposes of the present invention, all references as cited herein are incorporated by reference in their entireties.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A to 1V show the over-presentation of various peptides in normal tissues (white bars) and esophageal cancer (black bars). FIG. 1A) Gene symbol: KRT14/KRT16, Peptide: STYGGGLSV (SEQ ID NO: 1) Tissues from left to right: 1 adipose tissues, 3 adrenal glands, 8 arteries, 5 bone marrows, 7 brains, 5 breasts, 2 cartilages, 1 central nerve, 13 colons, 1 duodenum, 2 gallbladders, 5 hearts, 14 kidneys, 21 livers, 44 lungs, 4 lymph nodes, 4 leukocyte samples, 3 ovaries, 8 pancreas, 5 peripheral nerves, 1 peritoneum, 3 pituitary glands, 4 placentas, 3 pleuras, 3 prostates, 6 recti, 7 salivary glands, 4 skeletal muscles, 6 skins, 2 small intestines, 4 spleens, 5 stomachs, 6 testis, 3 thymi, 3 thyroid glands, 7 tracheas, 2 ureters, 6 urinary bladders, 2 uteri, 2 veins, 6 esophagi, 16 esophageal cancer samples. The peptide has additionally been detected on 4/91 lung cancers. FIG. 1B) Gene symbol: GJB5, Peptide: SIFEGLLSGV (SEQ ID NO: 7). Tissues from left to right: 1 adipose tissues, 3 adrenal glands, 8 arteries, 5 bone marrows, 7 brains, 5 breasts, 2 cartilages, 1 central nerve, 13 colons, 1 duodenum, 2 gallbladders, 5 hearts, 14 kidneys, 21 livers, 44 lungs, 4 lymph nodes, 4 leukocyte samples, 3 ovaries, 8 pancreas, 5 peripheral nerves, 1 peritoneum, 3 pituitary glands, 4 placentas, 3 pleuras, 3 prostates, 6 recti, 7 salivary glands, 4 skeletal muscles, 6 skins, 2 small intestines, 4 spleens, 5 stomachs, 6 testis, 3 thymi, 3 thyroid glands, 7 tracheas, 2 ureters, 6 urinary bladders, 2 uteri, 2 veins, 6 esophagi, 16 esophageal cancer samples. The peptide has additionally been detected on 1/43 prostate cancers, 1/3 gallbladder cancers, 1/20 ovarian cancers, 5/91 lung cancers and 1/4 urinary bladder cancers. FIG. 1C) Gene symbol: PKP3, Peptide: SLVSEQLEPA (SEQ ID NO: 34). Tissues from left to right: 1 adipose tissues, 3 adrenal glands, 8 arteries, 5 bone marrows, 7 brains, 5 breasts, 2 cartilages, 1 central nerve, 13 colons, 1 duodenum, 2 gallbladders, 5 hearts, 14 kidneys, 21 livers, 44 lungs, 4 lymph nodes, 4 leukocyte samples, 3 ovaries, 8 pancreas, 5 peripheral nerves, 1 peritoneum, 3 pituitary glands, 4 placentas, 3 pleuras, 3 prostates, 6 recti, 7 salivary glands, 4 skeletal muscles, 6 skins, 2 small intestines, 4 spleens, 5 stomachs, 6 testis, 3 thymi, 3 thyroid glands, 7 tracheas, 2 ureters, 6 urinary bladders, 2 uteri, 2 veins, 6 esophagi, 16 esophageal cancer samples. The peptide has additionally been detected on 8/24 colorectal cancers, 1/20 ovarian cancers, 1/46 gastric cancers, 5/91 lung cancers and 2/4 urinary bladder cancers. FIG. 1D) Gene symbol: RNPEP, Peptide: YTQPFSHYGQAL (SEQ ID NO: 37). Tissues from left to right: 1 adipose tissues, 3 adrenal glands, 8 arteries, 5 bone marrows, 7 brains, 5 breasts, 2 cartilages, 1 central nerve, 13 colons, 1 duodenum, 2 gallbladders, 5 hearts, 14 kidneys, 21 livers, 44 lungs, 4 lymph nodes, 4 leukocyte samples, 3 ovaries, 8 pancreas, 5 peripheral nerves, 1 peritoneum, 3 pituitary glands, 4 placentas, 3 pleuras, 3 prostates, 6 recti, 7 salivary glands, 4 skeletal muscles, 6 skins, 2 small intestines, 4 spleens, 5 stomachs, 6 testis, 3 thymi, 3 thyroid glands, 7 tracheas, 2 ureters, 6 urinary bladders, 2 uteri, 2 veins, 6 esophagi, 16 esophageal cancer samples. The peptide has additionally been detected on 1/19 pancreatic cancers, 7/46 gastric cancers and 1/91 lung cancers. FIG. 1E) Gene symbol: NUP155, Peptide: ALQEALENA (SEQ ID NO: 80). Samples from left to right: 4 cell lines (1 kidney, 1 pancreatic, 1 prostate, 1 myeloid leukemia), 3 normal tissues (1 lung, 1 prostate, 1 small intestine), 47 cancer tissues (5 brain cancers, 2 breast cancers, 1 colon cancers, 2 esophageal cancers, 1 chronic leukocytic leukemia, 2 liver cancers, 22 lung cancers, 7 ovarian cancers, 4 prostate cancers, 1 rectum cancer). FIG. 1F) Gene symbol: KRT5, Peptide: SLYNLGGSKRISI (SEQ ID NO: 2). Tissues from left to right: 20 cancer tissues (9 head-and-neck cancers, 2 esophageal cancers, 1 esophagus and stomach cancer, 7 lung cancers, 1 urinary bladder cancer). FIG. 1G) Gene symbol: KRT5, Peptide: TASAITPSV (SEQ ID NO: 3). Tissues from left to right: 17 cancer tissues (2 esophageal cancers, 6 head-and-neck cancers, 7 lung cancers, 2 urinary bladder cancers). FIG. 1H) Gene symbol: S100A2, Peptide: SLDENSDQQV (SEQ ID NO: 10). Tissues from left to right: 7 cancer tissues (3 head-and-neck cancers, 2 esophageal cancers, 1 lung cancer, 1 urinary bladder cancer). FIG. 1I) Gene symbol: LAMB3, Peptide: ALWLPTDSATV (SEQ ID NO: 11). Tissues from left to right: 12 cancer tissues (2 esophageal cancers, 1 gallbladder cancer, 8 lung cancers, 1 skin cancer). FIG. 1J) Gene symbol: IL36RN, Peptide: SLSPVILGV (SEQ ID NO: 13). Tissues from left to right: 26 cancer tissues (8 head-and-neck cancers, 3 esophageal cancers, 10 lung cancers, 3 skin cancers, 1 urinary bladder cancer, 1 uterus cancer). FIG. 1K) Gene symbol: ANO1, Peptide: LLANGVYAA (SEQ ID NO: 15). Tissues from left to right: 8 cancer tissues (2 esophageal cancers, 1 gallbladder cancer, 1 liver cancer, 1 lung cancer, 1 stomach cancer, 1 urinary bladder cancer, 1 uterus cancer). FIG. 1L) Gene symbol: F7, IGHV4-31, IGHG1, IGHG2, IGHG3, IGHG4, IGHM, Peptide: MISRTPEV (SEQ ID NO: 17). Tissues from left to right: 19 cancer tissues (2 esophageal cancers, 2 kidney cancers, 2 liver cancers, 9 lung cancers, 1 lymph node cancer, 1 testis cancer, 2 urinary bladder cancers. FIG. 1M) Gene symbol: QSER1, Peptide: SLNGNQVTV (SEQ ID NO: 30). Tissues from left to right: 1 cell line (1 pancreatic), 14 cancer tissues (1 head-and-neck cancer, 1 bile duct cancer, 1 brain cancer, 1 breast cancer, 1 esophageal cancer, 1 kidney cancer, 1 lung cancer, 2 skin cancers, 3 urinary bladder cancers, 2 uterus cancers). FIG. 1N) Gene symbol: HAS3, Peptide: YMLDIFHEV (SEQ ID NO: 32). Tissues from left to right: 1 normal tissue (1 uterus), 15 cancer tissues (1 brain cancer, 2 esophageal cancers, 1 gallbladder cancer, 3 head-and-neck cancers, 4 lung cancers, 4 urinary bladder cancers). FIG. 1O) Gene symbol: PKP3, Peptide: SLVSEQLEPA (SEQ ID NO: 34). Tissues from left to right: 1 cell line (1 pancreatic), 1 normal tissue (1 colon), 28 cancer tissues (6 head-and-neck cancers, 1 breast cancer, 1 cecum cancer, 3 colon cancers, 1 colorectal cancer, 3 esophageal cancers, 6 lung cancers, 1 ovarian cancer, 3 rectum cancers, 3 urinary bladder cancers). FIG. 1Q) Gene symbol: TMEM132A, Peptide: ALVEVTEHV (SEQ ID NO: 56). Tissues from left to right: 7 normal tissues (5 lungs, 1 thyroid gland, 1 trachea), 64 cancer tissues (6 head-and-neck cancers, 12 brain cancers, 4 breast cancers, 3 esophageal cancers, 1 gallbladder cancer, 5 kidney cancers, 21 lung cancers, 1 lymph node cancer, 7 ovarian cancers, 1 pancreas cancer, 1 skin cancer, 2 uterus cancers). FIG. 1R) Gene symbol: PRC1, Peptide: GLAPNTPGKA (SEQ ID NO: 57). Tissues from left to right: 14 cancer tissues (1 head-and-neck cancer, 1 breast cancer, 2 esophageal cancers, 6 lung cancers, 1 ovarian cancer, 1 skin cancer, 1 urinary bladder cancer, 1 uterus cancer). FIG. 1S) Gene symbol: MAPK6, Peptide: LILESIPVV (SEQ ID NO: 58). Tissues from left to right: 2 cell lines (1 blood cell, 1 skin), 25 cancer tissues (5 head-and-neck cancers, 1 colon cancer, 2 esophageal cancers, 1 leukocytic leukemia cancer, 8 lung cancers, 2 lymph node cancers, 3 skin cancers, 2 urinary bladder cancers, 1 uterus cancer). FIG. 1T) Gene symbol: PPP4R1, Peptide: SLLDTLREV (SEQ ID NO: 59). Tissues from left to right: 1 normal tissue (1 small intestine), 8 cancer tissues (1 head-and-neck cancer, 2 esophageal cancers, 4 lung cancers, 1 ovarian cancer). FIG. 1U) Gene symbol: TP63, Peptide: VLVPYEPPQV (SEQ ID NO: 77). Tissues from left to right: 2 normal tissues (1 esophagus, 1 trachea), 47 cancer tissues (8 head-and-neck cancers, 4 esophageal cancers, 1 gallbladder cancer, 14 lung cancers, 7 lymph node cancers, 2 prostate cancers, 1 skin cancer, 8 urinary bladder cancers. FIG. 1V) Gene symbol: KIAA0947, Peptide: AVLPHVDQV (SEQ ID NO: 81). Tissues from left to right: 3 cell lines (1 blood cells, 1 pancreatic), 12 cancer tissues (5 brain cancers, 2 esophageal cancers, 1 lung cancer, 3 lymph node cancers, 1 uterus cancer).

FIGS. 2A to 2D show exemplary expression profiles of source genes of the present invention that are highly overexpressed or exclusively expressed in esophageal cancer in a panel of normal tissues (white bars) and 11 esophageal cancer samples (black bars). Tissues from left to right: 7 arteries, 1 brain, 1 heart, 2 livers, 2 lungs, 2 veins, 1 adipose tissue, 1 adrenal gland, 4 bone marrows, 1 colon, 2 esophagi, 2 gallbladders, 1 kidney, 6 lymph nodes, 1 pancreas, 1 pituitary gland, 1 rectum, 1 skeletal muscle, 1 skin, 1 small intestine, 1 spleen, 1 stomach, 1 thymus, 1 thyroid gland, 5 tracheae, 1 urinary bladder, 1 breast, 3 ovaries, 3 placentae, 1 prostate, 1 testis, 1 uterus, 11 esophageal cancer samples. FIG. 2A) Gene symbol: PTHLH; FIG. 2B) Gene symbol: KRT14; FIG. 2C) Gene symbol: FAM83A; FIG. 2D) Gene symbol: PDPN.

FIGS. 3A to 3E show exemplary results of peptide-specific in vitro CD8+ T cell responses of a healthy HLA-A*02+ donor i.e. exemplary immunogenicity data: flow cytometry results after peptide-specific multimer staining. FIG. 3A) Gene symbol: SF3B3, Peptide: ELDRTPPEV (SEQ ID NO: 97); FIG. 3B) Gene symbol: TNC, Peptide: AMTQLLAGV (SEQ ID NO: 101). Also, CD8+ T cells were primed using artificial APCs coated with anti-CD28 mAb and HLA-A*02 in complex with SEQ ID NO: 5 peptide (FIG. 3C, left panel), SEQ ID NO: 2 peptide (FIG. 3D, left panel) and SEQ ID NO: 77 peptide (FIG. 3E, left panel), respectively. After three cycles of stimulation, the detection of peptide-reactive cells was performed by 2D multimer staining with A*02/SeqID No 5 (FIG. 3C), A*02/SeqID No 2 (FIG. 3D) or A*02/SeqID No 77 (FIG. 3E). Right panels (FIGS. 3C, 3D and 3E) show control staining of cells stimulated with irrelevant A*02/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

EXAMPLES

Example 1

Figure 1A:
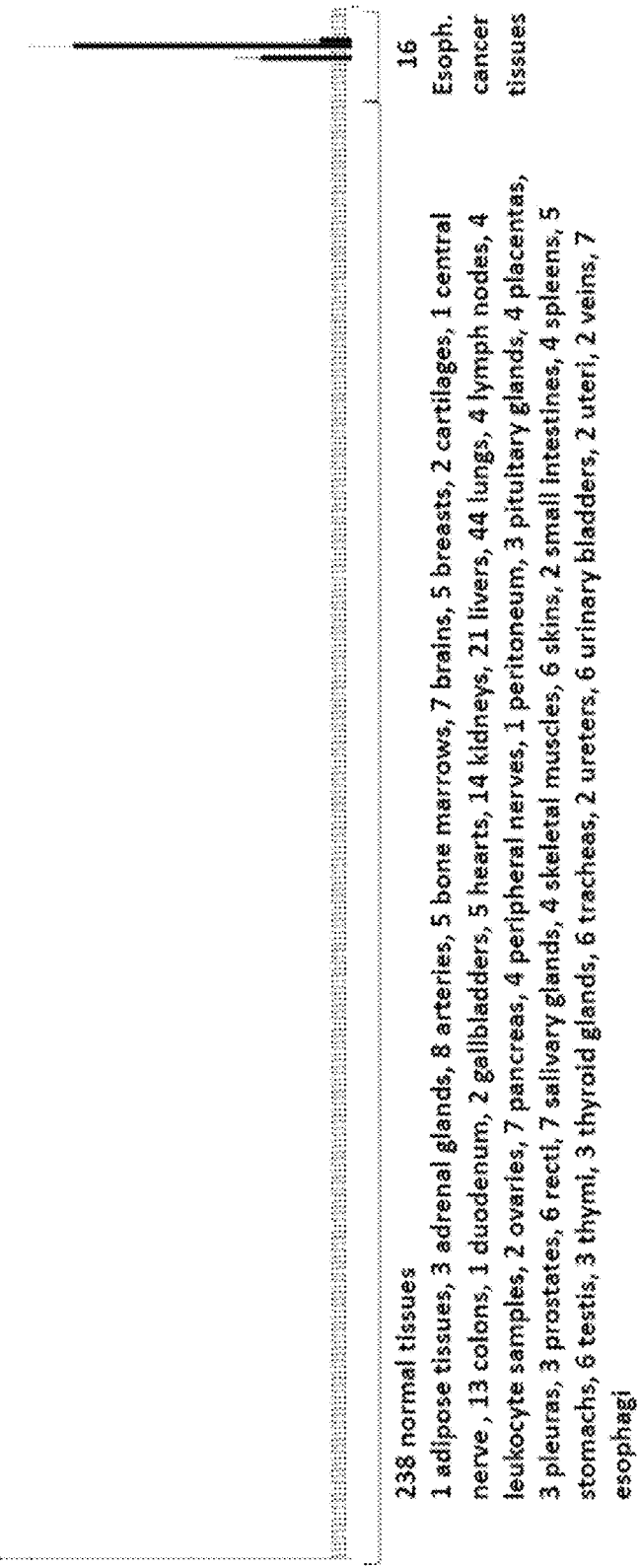
Figure 1P:
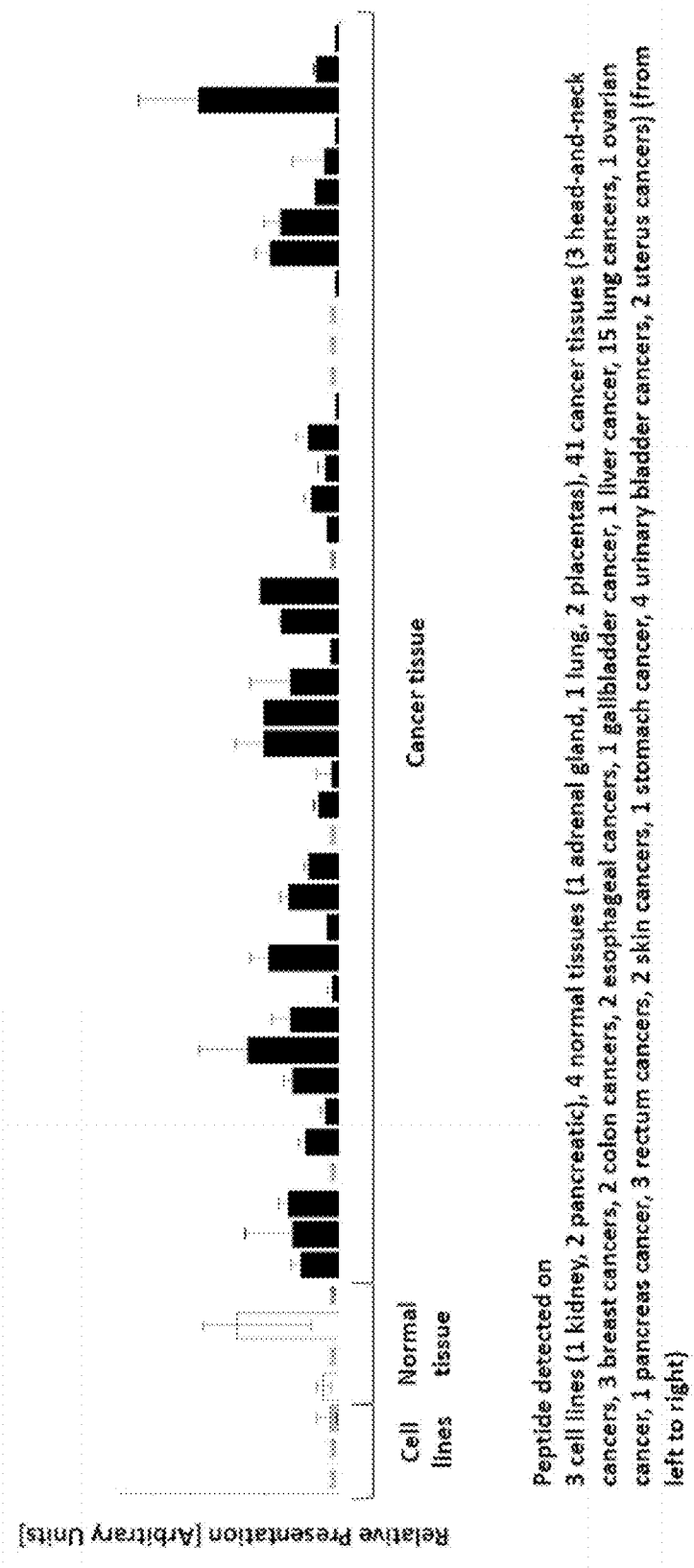
FIG. 1P) Gene symbol: SERPINH1, Peptide: GLAFSLYQA (SEQ ID NO: 40). Tissues from left to right: 3 cell lines (1 kidney, 2 pancreatic), 4 normal tissues (1 adrenal gland, 1 lung, 2 placentas), 41 cancer tissues (3 head-and-neck cancers, 3 breast cancers, 2 colon cancers, 2 esophageal cancers, 1 gallbladder cancer, 1 liver cancer, 15 lung cancers, 1 ovarian cancer, 1 pancreas cancer, 3 rectum cancers, 2 skin cancers, 1 stomach cancer, 4 urinary bladder cancers, 2 uterus cancers).
Figure 2A:
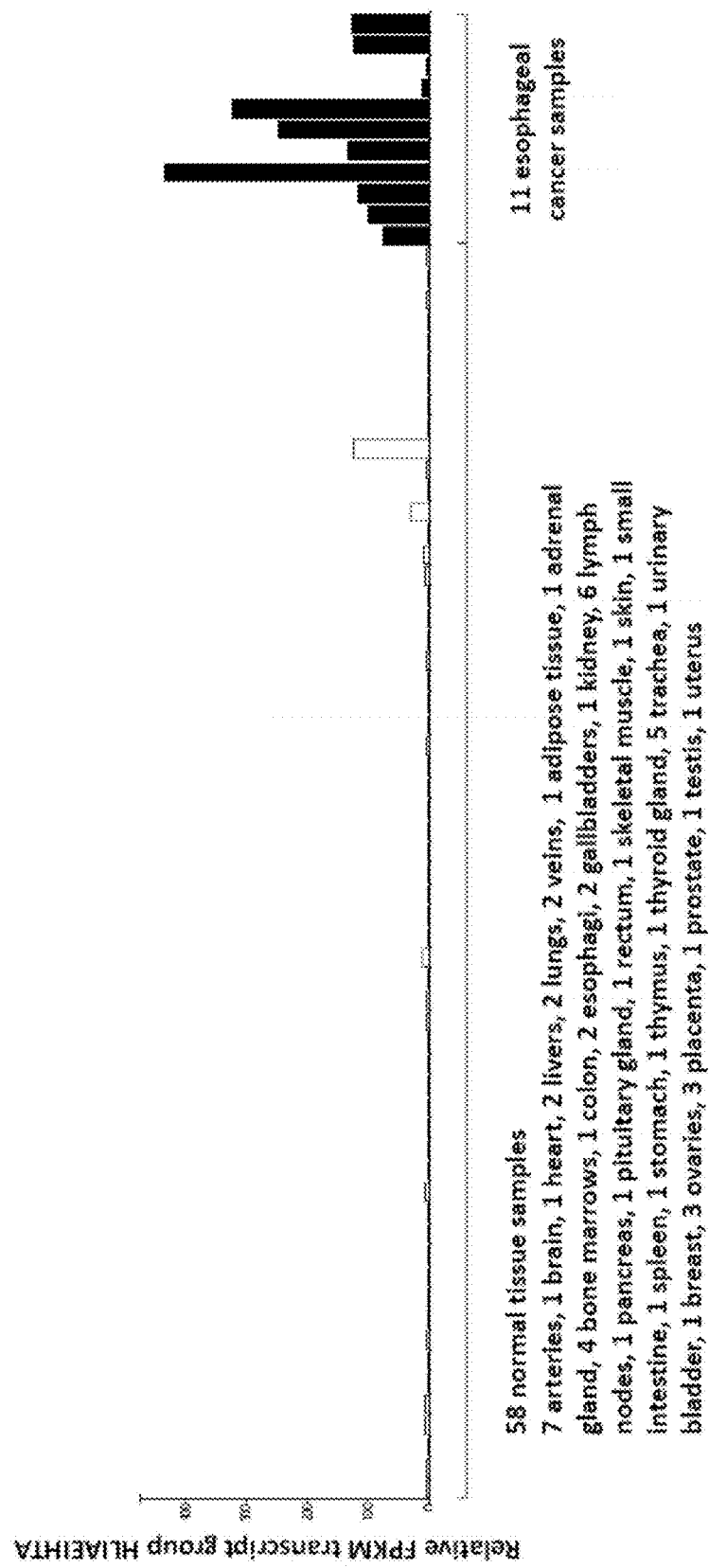
Figure 2C:
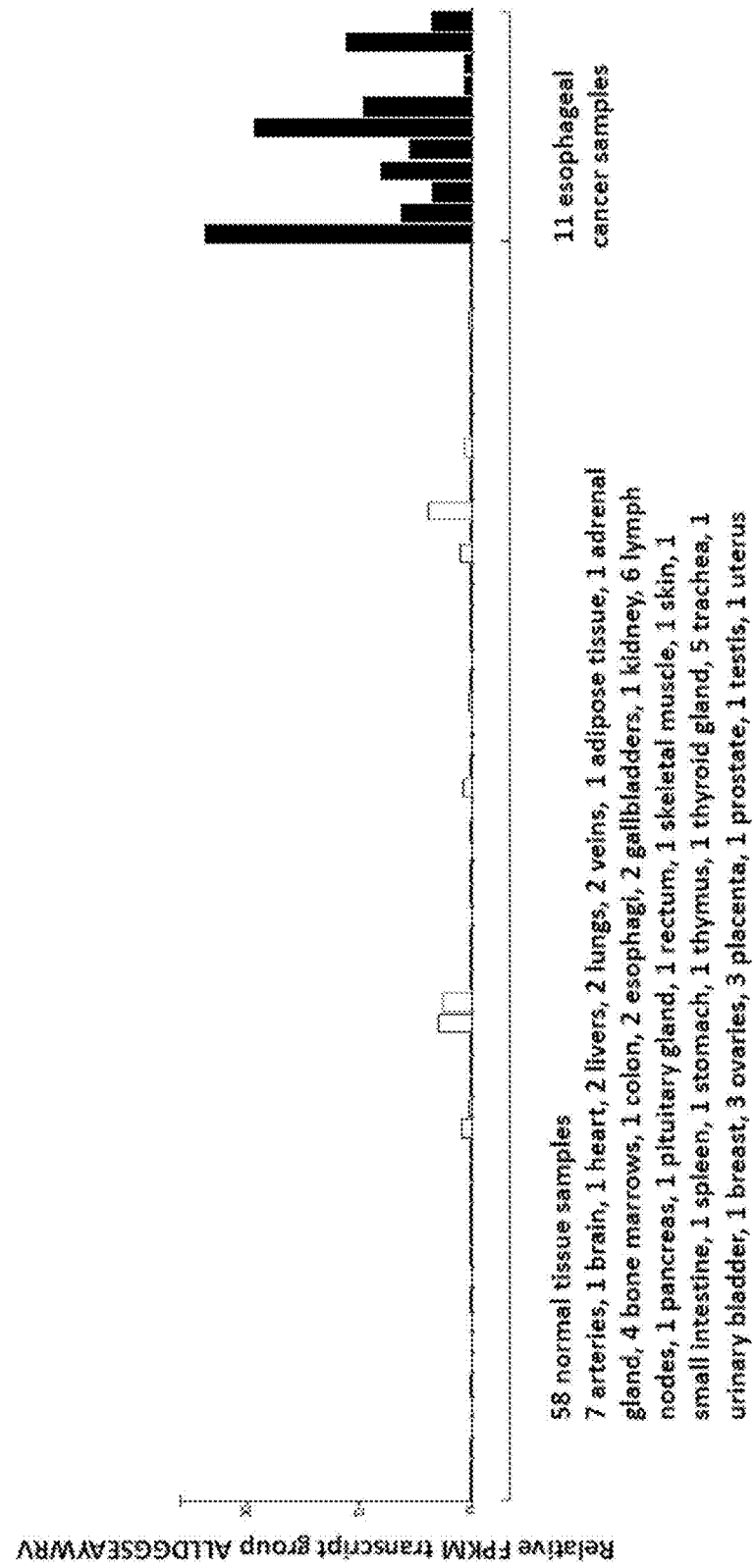
Figure 2D:
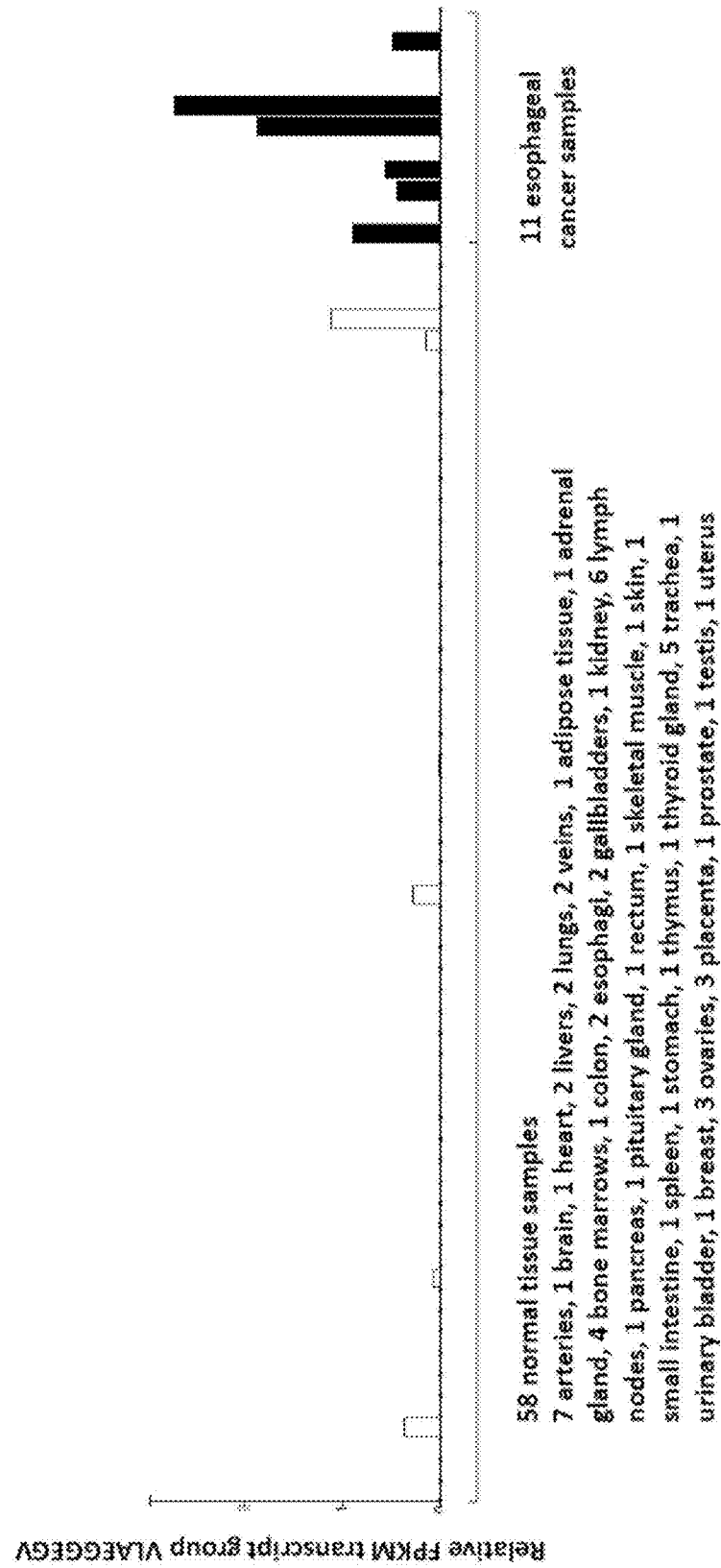
Figure 3A:
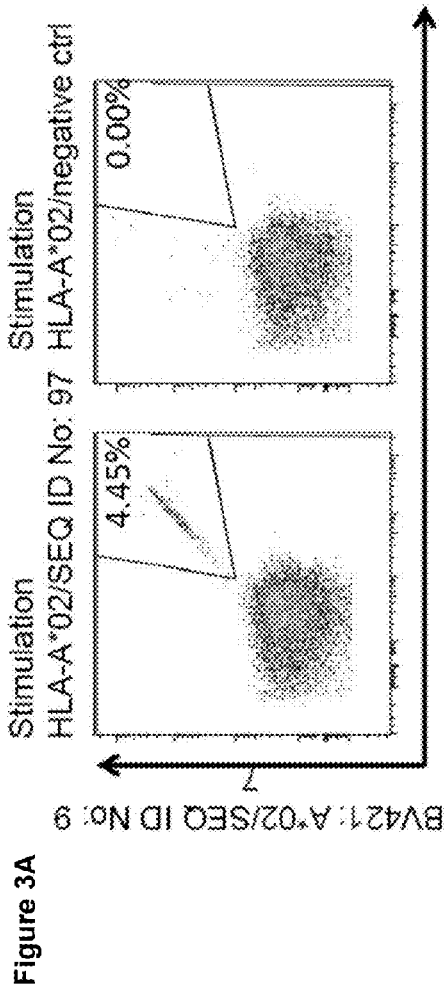
Figure 3B:
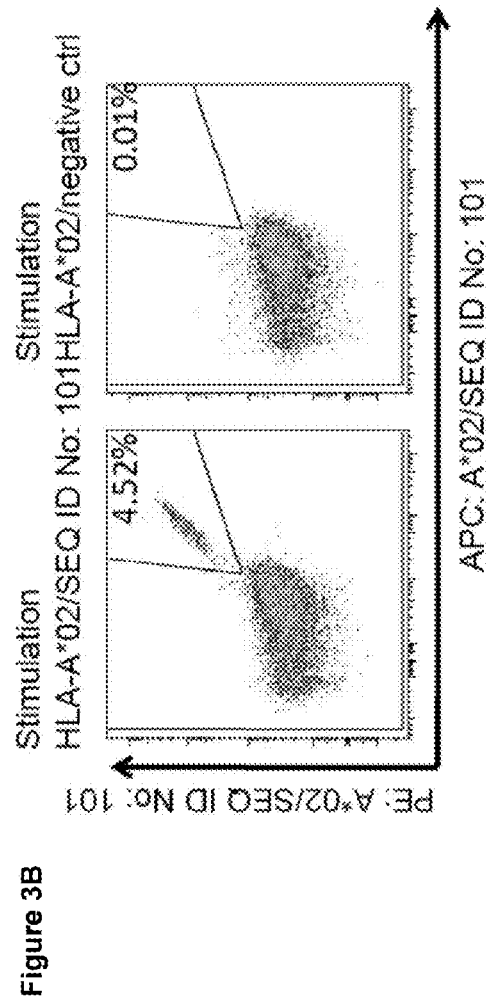
Figure 3C:
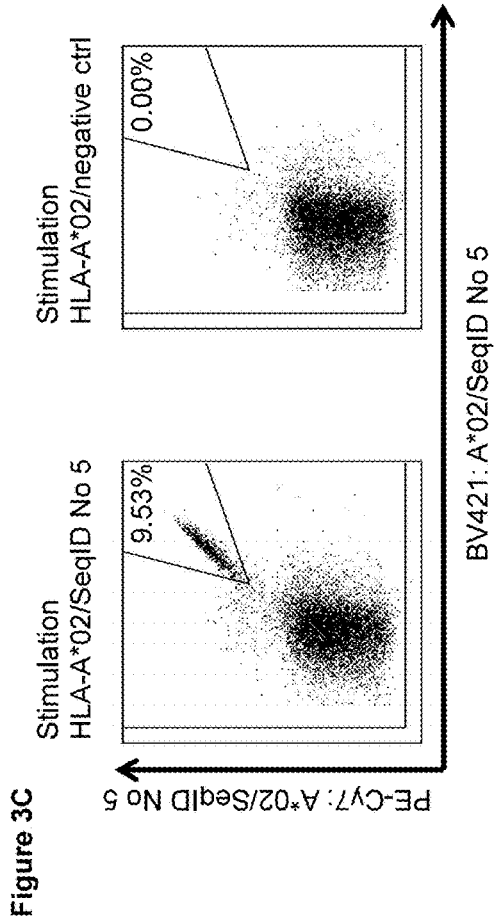
Figure 3D:
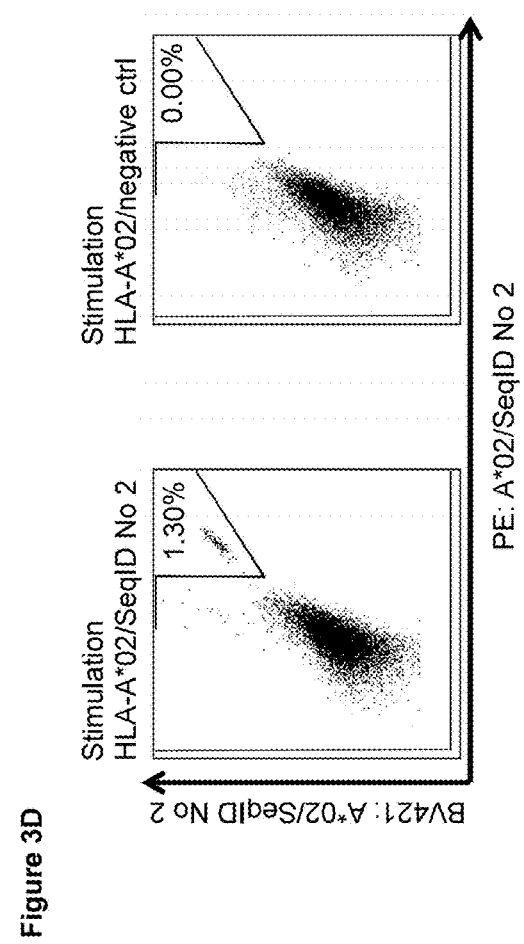

Identification and Quantitation of Tumor Associated Peptides Presented on the Cell Surface Tissue Samples Patients' tumor tissues were obtained from Asterand (Detroit, USA and Royston, Herts, UK); ProteoGenex Inc., (Culver City, Calif., USA); Tissue Solutions Ltd. (Glasgow, UK); University Hospital of Tübingen. Normal tissues were obtained from Asterand (Detroit, USA and Royston, Herts, UK); Bio-Options Inc. (CA, USA); BioServe (Beltsville, Md., USA); Capital BioScience Inc. (Rockville, Md., USA); Geneticist Inc. (Glendale, Calif., USA); University Hospital of Geneva; University Hospital of Heidelberg; Kyoto Prefectural University of Medicine (KPUM); University Hospital Munich; ProteoGenex Inc. (Culver City, Calif., USA); University Hospital of Tübingen; Tissue Solutions Ltd. (Glasgow, UK). Written informed consents of all patients had been given before surgery or autopsy. Tissues were shock-frozen immediately after excision and stored until isolation of TUMAPs at −70° C. or below.

Isolation of HLA Peptides from Tissue Samples HLA peptide pools from shock-frozen tissue samples were obtained by immune precipitation from solid tissues according to a slightly modified protocol (Falk et al., 1991; Seeger et al., 1999) using the HLA-A*02-specific antibody BB7.2, the HLA-A, —B, C-specific antibody W6/32, CNBr-activated sepharose, acid treatment, and ultrafiltration.

Mass Spectrometry Analyses

The HLA peptide pools as obtained were separated according to their hydrophobicity by reversed-phase chromatography (nanoAcquity UPLC system, Waters) and the eluting peptides were analyzed in LTQ- velos and fusion hybrid mass spectrometers (ThermoElectron) equipped with an ESI source. Peptide pools were loaded directly onto the analytical fused-silica micro-capillary column (75 μm i.d.× 250 mm) packed with 1.7 μm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometers were operated in the data-dependent mode using a TOPS strategy. In brief, a scan cycle was initiated with a full scan of high mass accuracy in the Orbitrap (R=30 000), which was followed by MS/MS scans also in the Orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide.

Label-free relative LC-MS quantitation was performed by ion counting i.e. by extraction and analysis of LC-MS features (Mueller et al., 2007). The method assumes that the peptide's LC-MS signal area correlates with its abundance in the sample. Extracted features were further processed by charge state deconvolution and retention time alignment (Mueller et al., 2008; Sturm et al., 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profiles juxtapose esophageal cancer samples to a baseline of normal tissue samples.

Presentation profiles of exemplary over-presented peptides are shown in FIGS. 1A-1V. Presentation scores for exemplary peptides are shown in Table 8.

TABLE 8

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+). The panel of normal tissues consisted of: adipose tissue, adrenal gland, artery, vein, bone marrow, brain, central and peripheral nerve, colon, rectum, small intestine incl. duodenum, esophagus, gallbladder, heart, kidney, liver, lung, lymph node, mononuclear white blood cells, pancreas, peritoneum, pituitary, pleura, salivary gland, skeletal muscle, skin, spleen, stomach, thymus, thyroid gland, trachea, ureter, urinary bladder.

| SEQ ID No. | Sequence | Peptide Presentation |
|---|---|---|
| 1 | STYGGGLSV | +++ |
| 2 | SLYNLGGSKRISI | +++ |
| 3 | TASAITPSV | +++ |
| 4 | ALFGTILEL | ++ |
| 5 | NLMASQPQL | +++ |
| 6 | LLSGDLIFL | +++ |
| 7 | SIFEGLLSGV | +++ |
| 8 | ALLDGGSEAYWRV | +++ |
| 9 | HLIAEIHTA | +++ |
| 10 | SLDENSDQQV | +++ |
| 11 | ALWLPTDSATV | +++ |
| 12 | GLASRILDA | +++ |
| 13 | SLSPVILGV | +++ |
| 14 | RLPNAGTQV | +++ |
| 15 | L LAN GVYAA | +++ |
| 16 | VLAEGGEGV | +++ |
| 17 | MISRTPEV | +++ |
| 18 | FLLDQVQLGL | +++ |
| 19 | GLAPFLLNAV | +++ |
| 20 | IIEVDPDTKEML | +++ |
| 21 | IVREFLTAL | +++ |
| 22 | KLNDTYVNV | +++ |
| 23 | KLSDSATYL | +++ |
| 24 | LLFAGTMTV | +++ |
| 25 | LLPPPPPA | +++ |
| 26 | MLAEKLLQA | +++ |
| 27 | NLREGDQLL | +++ |
| 28 | SLDGFTIQV | +++ |
| 29 | SLDGTELQL | +++ |
| 30 | SLNGNQVTV | +++ |
| 32 | YMLDIFHEV | +++ |
| 33 | GLDVTSLRPFDL | +++ |

TABLE 8-continued

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+). The panel of normal tissues consisted of: adipose tissue, adrenal gland, artery, vein, bone marrow, brain, central and peripheral nerve, colon, rectum, small intestine incl. duodenum, esophagus, gallbladder, heart, kidney, liver, lung, lymph node, mononuclear white blood cells, pancreas, peritoneum, pituitary, pleura, salivary gland, skeletal muscle, skin, spleen, stomach, thymus, thyroid gland, trachea, ureter, urinary bladder.

| SEQ ID No. | Sequence | Peptide Presentation |
|---|---|---|
| 34 | SLVSEQLEPA | + |
| 35 | LLRFSQDNA | +++ |
| 36 | FLLRFSQDNA | +++ |
| 37 | YTQPFSHYGQAL | +++ |
| 38 | IAAIRGFLV | +++ |
| 39 | LVRDTQSGSL | +++ |
| 40 | GLAFSLYQA | +++ |
| 41 | GLESEELEPEEL | + |
| 44 | ATGNDRKEAAENSL | +++ |
| 45 | MLTELEKAL | +++ |
| 47 | VLASGFLTV | +++ |
| 48 | SMHQMLDQTL | +++ |
| 50 | GMNPHQTPAQL | +++ |
| 51 | KLFGHLTSA | +++ |
| 52 | VAIGGVDGNVRL | +++ |
| 55 | GAIDLLHNV | +++ |
| 57 | GLAPNTPGKA | +++ |
| 58 | LILESIPVV | +++ |
| 59 | SLLDTLREV | +++ |
| 61 | TQTTHELTI | +++ |
| 62 | ALYEYQPLQI | +++ |
| 63 | LAYTLGVKQL | +++ |
| 64 | GLTDVIRDV | ++ |
| 65 | YVVGGFLYQRL | +++ |
| 66 | LLDEKVQSV | + |
| 68 | PAVLQSSGLYSL | +++ |
| 70 | FVLDTSESV | + |
| 71 | ASDPILYRPVAV | + |
| 72 | FLPPAQVTV | + |
| 73 | KITEAIQYV | + |
| 75 | GLMDDVDFKA | + |
| 77 | VLVPYEPPQV | ++ |
| 78 | KVANIIAEV | + |
| 80 | ALQEALENA | ++ |
| 81 | AVLPHVDQV | +++ |
| 82 | HLLGHLEQA | +++ |
| 84 | SLAESLDQA | + |
| 86 | GLLTEIRAV | + |
| 87 | FLDNGPKTI | + |
| 88 | GLWEQENHL | + |
| 89 | SLADSLYNL | + |
| 91 | KLIDDVHRL | + |
| 92 | SILRHVAEV | + |
| 94 | TLLQEQGTKTV | + |

Example 2

Expression Profiling of Genes Encoding the Peptides of the Invention

Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immunotherapies. Especially for therapeutic options with high safety risks, such as affinity-matured TCRs, the ideal target peptide will be derived from a protein that is unique to the tumor and not found on normal tissues.

RNA Sources and Preparation

Surgically removed tissue specimens were provided as indicated above (see Example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from tumor tissue for RNASeq experiments was obtained from: ProteoGenex Inc. (Culver City, Calif., USA); Tissue Solutions Ltd. (Glasgow, UK).

Total RNA from healthy human tissues for RNASeq experiments was obtained from: Asterand (Detroit, USA and Royston, Herts, UK); ProteoGenex Inc. (Culver City, Calif., USA); Geneticist Inc. (Glendale, Calif., USA); Istituto Nazionale Tumori "Pascale", Molecular Biology and Viral Oncology Unit (IRCCS) (Naples, Italy); University Hospital of Heidelberg (Germany); BioCat GmbH (Heidelberg, Germany).

Quality and quantity of all RNA samples were assessed on an Agilent 2100 Bioanalyzer (Agilent, Waldbronn, Germany) using the RNA 6000 Pico LabChip Kit (Agilent).

RNAseq Experiments

Gene expression analysis of—tumor and normal tissue RNA samples was performed by next generation sequencing (RNAseq) by CeGaT (Tübingen, Germany). Briefly, sequencing libraries are prepared using the Illumina HiSeq v4 reagent kit according to the provider's protocol (Illumina Inc, San Diego, Calif., USA), which includes RNA fragmentation, cDNA conversion and addition of sequencing adaptors. Libraries derived from multiple samples are mixed equimolarly and sequenced on the Illumina HiSeq 2500 sequencer according to the manufacturer's instructions, generating 50 bp single end reads. Processed reads are mapped to the human genome (GRCh38) using the STAR software. Expression data are provided on transcript level as RPKM (Reads Per Kilobase per Million mapped reads, generated by the software Cufflinks) and on exon level (total reads, generated by the software Bedtools), based on annotations of the ensembl sequence database (Ensembl77). Exon reads are normalized for exon length and alignment size to obtain RPKM values.

Exemplary expression profiles of source genes of the present invention that are highly over-expressed or exclusively expressed in esophageal cancer are shown in FIGS. 2A-2D. Expression scores for further exemplary genes are shown in Table 9.

TABLE 9

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following normal tissues: adipose tissue, adrenal gland, artery, bone marrow, brain, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder, vein.

| SEQ ID No. | Sequence | Gene Expression |
| --- | --- | --- |
| 1 | STYGGGLSV | +++ |
| 2 | SLYNLGGSKRISI | +++ |
| 3 | TASAITPSV | +++ |
| 4 | ALFGTILEL | ++ |
| 5 | NLMASQPQL | +++ |
| 6 | LLSGDLIFL | +++ |
| 7 | SIFEGLLSGV | +++ |
| 8 | ALLDGGSEAYWRV | +++ |
| 9 | HLIAEIHTA | +++ |
| 10 | SLDENSDQQV | +++ |
| 11 | ALWLPTDSATV | +++ |
| 12 | GLASRILDA | +++ |
| 13 | SLSPVILGV | +++ |
| 14 | RLPNAGTQV | +++ |
| 15 | LLANGVYAA | +++ |
| 16 | VLAEGGEGV | +++ |
| 17 | MISRTPEV | +++ |
| 18 | FLLDQVQLGL | +++ |
| 24 | LLFAGTMTV | +++ |
| 25 | LLPPPPPPA | + |
| 26 | MLAEKLLQA | ++ |
| 27 | NLREGDQLL | +++ |
| 32 | YMLDIFHEV | +++ |
| 49 | GLMKDIVGA | + |
| 55 | GAIDLLHNV | ++ |
| 57 | GLAPNTPGKA | + |
| 67 | SMNGGVFAV | ++ |
| 69 | GLLVGSEKVTM | +++ |
| 71 | ASDPILYRPVAV | + |
| 77 | VLVPYEPPQV | +++ |
| 80 | ALQEALENA | + |
| 94 | TLLQEQGTKTV | +++ |

Example 3

In Vitro Immunogenicity for MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for HLA-A*0201 restricted TUMAPs of the invention, demonstrating that these peptides are T-cell epitopes against which CD8+ precursor T cells exist in humans (Table 10).

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02 leukapheresis products via positive selection using CD8 microbeads (Miltenyi Biotec, Bergisch-Gladbach, Germany) of healthy donors obtained from the University clinics Mannheim, Germany, after informed consent.

PBMCs and isolated CD8+ lymphocytes were incubated in T-cell medium (TCM) until use consisting of RPMI- Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nürnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*0201/MLA-001 (peptide ELAGIGILTV (SEQ ID NO. 102) from modified Melan-A/MART-1) and A*0201/DDX5-001 (YLLPAIVHI from DDX5, SEQ ID NO. 103), respectively.

800.000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating 1×10$^6$ CD8+ T cells with 2×10$^5$ washed coated beads in 200 µl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oregon, USA). In vitro priming of specific multimer+CD8+ lymphocytes was detected by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the negative control stimulations).

In Vitro Immunogenicity for Esophageal Cancer Peptides

For tested HLA class I peptides, in vitro immunogenicity could be demonstrated by generation of peptide specific T-cell lines. Exemplary flow cytometry results after TUMAP-specific multimer staining for two peptides (SEQ ID No 97 and SEQ ID No 101) of the invention are shown in FIGS. 3A-3E together with corresponding negative controls. Results for five peptides from the invention are summarized in Table 10A.

TABLE 10A in vitro immunogenicity of HLA class I peptides of the invention
Exemplary results of in vitro immunogenicity experiments conducted by the applicant for the peptides of the invention. <20% = +; 20%-49% = ++; 50%-69% = +++; >=70% = ++++

| SEQ ID No | Sequence | wells | Donors |
|---|---|---|---|
| 94 | TLLQEQGTKTV | + | ++ |
| 95 | LIQDRVAEV | + | ++ |
| 97 | ELDRTPPEV | ++ | ++++ |
| 98 | VLFPNLKTV | + | ++++ |
| 101 | AMTQLLAGV | ++ | +++ |

TABLE 10B

In vitro immunogenicity of HLA class I peptides of the invention
Exemplary results of in vitro immunogenicity experiments conducted by the applicant for peptides of the invention. Results of in vitro immunogenicity experiments are indicated. Percentage of positive wells and donors (among evaluable) are summarized as indicated <20% = +; 20%-49% = ++; 50%-69% = +++; >=70% = ++++

| SEQ ID No | Sequence | Wells positive [%] |
|---|---|---|
| 1 | STYGGGLSV | + |
| 2 | SLYNLGGSKRISI | + |
| 5 | NLMASQPQL | +++ |
| 6 | LLSGDLIFL | ++ |
| 12 | GLASRILDA | + |
| 19 | GLAPFLLNAV | + |
| 29 | SLDGTELQL | + |
| 47 | VLASGFLTV | +++ |
| 69 | GLLVGSEKVTM | + |
| 77 | VLVPYEPPQV | + |

Example 4

Synthesis of Peptides

All peptides were synthesized using standard and well-established solid phase peptide synthesis using the Fmoc-strategy. Identity and purity of each individual peptide have been determined by mass spectrometry and analytical RP-HPLC. The peptides were obtained as white to off-white lyophilizates (trifluoro acetate salt) in purities of >50%. All TUMAPs are preferably administered as trifluoro-acetate salts or acetate salts, other salt-forms are also possible.

Example 5

MHC Binding Assays

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (β2m) of stabilized MHC complexes. The assay was performed as generally described in Rodenko et al. (Rodenko et al., 2006).

96 well MAXISorp plates (NUNC) were coated over night with 2 ug/ml streptavidin in PBS at room temperature, washed 4× and blocked for 1h at 37° C. in 2% BSA containing blocking buffer. Refolded HLA-A*02:01/MLA-001 monomers served as standards, covering the range of 15-500 ng/ml. Peptide-MHC monomers of the UV-exchange reaction were diluted 100 fold in blocking buffer. Samples were incubated for 1 h at 37° C., washed four times, incubated with 2 ug/ml HRP conjugated anti-β2m for 1h at 37° C., washed again and detected with TMB solution that is stopped with $NH_2SO_4$. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

TABLE 11

MHC class I binding scores.
Binding of HLA-class I restricted peptides
to HLA-A*02:01 was ranged by peptide
exchange yield: ≥10% =+; ≥20% = ++;
≥50 = +++; ≥75% = ++++

| SEQ ID | Sequence | Peptide exchange |
|---|---|---|
| 1 | STYGGGLSV | +++ |
| 2 | SLYNLGGSKRISI | ++++ |
| 3 | TASAITPSV | +++ |
| 5 | NLMASQPQL | +++ |
| 6 | LLSGDLIFL | +++ |
| 7 | SIFEGLLSGV | ++ |
| 8 | ALLDGGSEAYWRV | +++ |
| 9 | HLIAEIHTA | +++ |
| 10 | SLDENSDQQV | +++ |
| 11 | ALWLPTDSATV | +++ |
| 12 | GLASRILDA | +++ |
| 13 | SLSPVILGV | ++++ |
| 14 | RLPNAGTQV | ++++ |
| 15 | LLANGVYAA | + |
| 16 | VLAEGGEGV | +++ |
| 17 | MISRTPEV | ++ |
| 18 | FLLDQVQLGL | +++ |
| 19 | GLAPFLLNAV | +++ |
| 21 | IVREFLTAL | +++ |
| 22 | KLNDTYVNV | +++ |
| 23 | KLSDSATYL | +++ |
| 24 | LLFAGTMTV | ++ |
| 25 | LLPPPPPA | +++ |
| 26 | MLAEKLLQA | + |
| 27 | NLREGDQLL | +++ |
| 28 | SLDGFTIQV | ++ |
| 29 | SLDGTELQL | +++ |
| 30 | SLNGNQVTV | + |
| 31 | VLPKLYVKL | ++ |
| 32 | YMLDIFHEV | ++ |
| 33 | GLDVTSLRPFDL | +++ |
| 34 | SLVSEQLEPA | +++ |
| 35 | LLRFSQDNA | +++ |
| 36 | FLLRFSQDNA | ++ |
| 37 | YTQPFSHYGQAL | +++ |
| 38 | IAAIRGFLV | +++ |
| 39 | LVRDTQSGSL | ++ |
| 40 | GLAFSLYQA | ++ |
| 41 | GLESEELEPEEL | ++ |
| 42 | TQTAVITRI | + |
| 43 | KVVGKDYLL | + |
| 44 | ATGNDRKEAAENSL | +++ |
| 45 | MLTELEKAL | ++ |
| 46 | YTAQIGADIAL | +++ |
| 47 | VLASGFLTV | ++++ |
| 48 | SMHQMLDQTL | ++ |
| 49 | GLMKDIVGA | +++ |
| 51 | KLFGHLTSA | ++ |

TABLE 11-continued

MHC class I binding scores.
Binding of HLA-class I restricted peptides
to HLA-A*02:01 was ranged by peptide
exchange yield: ≥10% =+; ≥20% = ++;
≥50 = +++; ≥75% = ++++

| SEQ ID | Sequence | Peptide exchange |
|---|---|---|
| 52 | VAIGGVDGNVRL | ++ |
| 53 | VVVTGLTLV | ++ |
| 54 | YQDLLNVKM | +++ |
| 55 | GAIDLLHNV | ++ |
| 56 | ALVEVTEHV | ++ |
| 57 | GLAPNTPGKA | +++ |
| 58 | LILESIPVV | ++ |
| 59 | SLLDTLREV | +++ |
| 60 | VVMEELLKV | ++ |
| 61 | TQTTHELTI | +++ |
| 62 | ALYEYQPLQI | ++ |
| 63 | LAYTLGVKQL | +++ |
| 64 | GLTDVIRDV | ++++ |
| 65 | YVVGGFLYQRL | +++ |
| 66 | LLDEKVQSV | +++ |
| 67 | SMNGGVFAV | ++ |
| 68 | PAVLQSSGLYSL | ++ |
| 69 | GLLVGSEKVTM | +++ |
| 70 | FVLDTSESV | +++ |
| 71 | ASDPILYRPVAV | +++ |
| 72 | FLPPAQVTV | ++ |
| 73 | KITEAIQYV | +++ |
| 74 | ILASLATSV | +++ |
| 76 | KVADYIPQL | +++ |
| 77 | VLVPYEPPQV | ++ |
| 78 | KVANIIAEV | ++ |
| 79 | GQDVGRYQV | ++ |
| 80 | ALQEALENA | ++ |
| 81 | AVLPHVDQV | +++ |
| 82 | HLLGHLEQA | +++ |
| 83 | ALADGVVSQA | +++ |
| 84 | SLAESLDQA | +++ |
| 85 | NIIELVHQV | ++++ |
| 87 | FLDNGPKTI | +++ |
| 89 | SLADSLYNL | ++ |
| 90 | SIYEYYHAL | +++ |
| 91 | KLIDDVHRL | ++++ |
| 92 | SILRHVAEV | ++ |
| 93 | VLINTSVTL | +++ |

Example 6

Absolute Quantitation of Tumor Associated Peptides Presented on the Cell Surface The generation of binders, such as antibodies and/or TCRs, is a laborious process, which may be conducted only for a number of selected targets. In the case of tumor-associated and -specific peptides, selection criteria include but are not restricted to exclusiveness of presentation and the density of peptide presented on the cell surface. The quantitation of TUMAP copies per cell in solid tumor samples requires the absolute quantitation of the isolated TUMAP, the efficiency of TUMAP isolation, and the cell count of the tissue sample analyzed.

Peptide Quantitation by nanoLC-MS/MS

For an accurate quantitation of peptides by mass spectrometry, a calibration curve was generated for each peptide using the internal standard method. The internal standard is a double-isotope-labelled variant of each peptide, i.e. two isotope-labelled amino acids were included in TUMAP synthesis. It differs from the tumor-associated peptide only in its mass but shows no difference in other physicochemical properties (Anderson et al., 2012). The internal standard was spiked to each MS sample and all MS signals were normalized to the MS signal of the internal standard to level out potential technical variances between MS experiments.

The calibration curves were prepared in at least three different matrices, i.e. HLA peptide eluates from natural samples similar to the routine MS samples, and each preparation was measured in duplicate MS runs. For evaluation, MS signals were normalized to the signal of the internal standard and a calibration curve was calculated by logistic regression.

For the quantitation of tumor-associated peptides from tissue samples, the respective samples were also spiked with the internal standard; the MS signals were normalized to the internal standard and quantified using the peptide calibration curve.

Efficiency of Peptide/MHC Isolation

As for any protein purification process, the isolation of proteins from tissue samples is associated with a certain loss of the protein of interest. To determine the efficiency of TUMAP isolation, peptide/MHC complexes were generated for all TUMAPs selected for absolute quantitation. To be able to discriminate the spiked from the natural peptide/MHC complexes, single-isotope-labelled versions of the TUMAPs were used, i.e. one isotope-labelled amino acid was included in TUMAP synthesis. These complexes were spiked into the freshly prepared tissue lysates, i.e. at the earliest possible point of the TUMAP isolation procedure, and then captured like the natural peptide/MHC complexes in the following affinity purification. Measuring the recovery of the single-labelled TUMAPs therefore allows conclusions regarding the efficiency of isolation of individual natural TUMAPs.

The efficiency of isolation was analyzed in a low number of samples and was comparable among these tissue samples. In contrast, the isolation efficiency differs between individual peptides. This suggests that the isolation efficiency, although determined in only a limited number of tissue samples, may be extrapolated to any other tissue preparation. However, it is necessary to analyze each TUMAP individually as the isolation efficiency may not be extrapolated from one peptide to others.

Determination of the Cell Count in Solid, Frozen Tissue

In order to determine the cell count of the tissue samples subjected to absolute peptide quantitation, the inventors applied DNA content analysis. This method is applicable to a wide range of samples of different origin and, most importantly, frozen samples (Alcoser et al., 2011; Forsey and Chaudhuri, 2009; Silva et al., 2013). During the peptide isolation protocol, a tissue sample is processed to a homogenous lysate, from which a small lysate aliquot is taken. The aliquot is divided in three parts, from which DNA is isolated (QiaAmp DNA Mini Kit, Qiagen, Hilden, Germany). The total DNA content from each DNA isolation is quantified using a fluorescence-based DNA quantitation assay (Qubit dsDNA HS Assay Kit, Life Technologies, Darmstadt, Germany) in at least two replicates.

In order to calculate the cell number, a DNA standard curve from aliquots of single healthy blood cells, with a range of defined cell numbers, has been generated. The standard curve is used to calculate the total cell content from the total DNA content from each DNA isolation. The mean total cell count of the tissue sample used for peptide isolation is extrapolated considering the known volume of the lysate aliquots and the total lysate volume.

Peptide Copies Per Cell

With data of the aforementioned experiments, the inventors calculated the number of TUMAP copies per cell by dividing the total peptide amount by the total cell count of the sample, followed by division through isolation efficiency. Copy cell numbers for selected peptides are shown in Table 12.

TABLE 12

Absolute copy numbers. The table lists the results of absolute peptide quantitation in NSCLC tumor samples. The median number of copies per cell are indicated for each peptide: <100 =+; >100 = ++; >=1,000 +++; >=10,000 = ++++. The number of samples, in which evaluable, high quality MS data are available, is indicated.

| SEQ ID No. | Peptide Code | Copies per cell (median) | Number of samples |
|---|---|---|---|
| 9 | PTHL-001 | + | 31 |

REFERENCE LIST

Abbas, W. et al., Front Oncol 5 (2015): 75
Adams, S. et al., PLoS. One. 9 (2014): e112945
Al Moustafa, A. E. et al., Oncogene 21 (2002): 2634-2640
Al-Mandi, R. et al., Cell Adh. Migr. (2015): 0
Alcoser, S. Y. et al., BMC. Biotechnol. 11 (2011): 124
Alholle, A. et al., Epigenetics. 8 (2013): 1198-1204
Ali, R. H. et al., Hum. Pathol. 45 (2014): 2453-2462
Allison, J. P. et al., Science 270 (1995): 932-933
Alper, M. et al., Mol. Cell Biochem. 393 (2014): 165-175
Alsagaby, S. A. et al., J Proteome. Res 13 (2014): 5051-5062
Altmannsberger, M. et al., Am. J Pathol. 118 (1985): 85-95
Ammendola, M. et al., PLoS. One. 9 (2014): e99512
Andersen, R. S. et al., Nat. Protoc. 7 (2012): 891-902
Anderson, N. L. et al., J Proteome. Res 11 (2012): 1868-1878
Appay, V. et al., Eur. J Immunol. 36 (2006): 1805-1814
Arentz, G. et al., Clin Proteomics. 8 (2011): 16
Arif, Q. et al., Arch. Pathol. Lab Med. 139 (2015): 978-980
Auvinen, P. et al., Breast Cancer Res Treat. 143 (2014): 277-286
Avasarala, S. et al., PLoS. One. 8 (2013): e76895
Banchereau, J. et al., Cell 106 (2001): 271-274
Bandres, E. et al., Oncol Rep. 12 (2004): 287-292
Banerjee, K. et al., Int. J Cancer (2015)
Barros-Filho, M. C. et al., J Clin Endocrinol. Metab 100 (2015): E890-E899
Bashyam, M. D. et al., Neoplasia. 7 (2005): 556-562
Basu, S. et al., PLoS. One. 10 (2015): e0123979
Baxter, P. A. et al., Acta Neuropathol. Commun. 2 (2014): 160
Beatty, G. et al., J Immunol 166 (2001): 2276-2282
Becker, S. A. et al., Cancer Res 56 (1996): 5092-5097
Beggs, J. D., Nature 275 (1978): 104-109
Bellon, M. et al., Blood 121 (2013): 5045-5054
Benjamini, Y. et al., Journal of the Royal Statistical Society. Series B (Methodological), Vol. 57 (1995): 289-300
Bhattacharjee, R. B. et al., Cell Biol Int. 36 (2012): 697-704
Bin Amer, S. M. et al., Saudi. Med. J 29 (2008): 507-513
Blanch, A. et al., PLoS. One. 8 (2013): e66436
Blanco, M. A. et al., Cell Res 22 (2012): 1339-1355
Blenk, S. et al., Cancer Inform. 3 (2007): 399-420
Boulter, J. M. et al., Protein Eng 16 (2003): 707-711
Boyer, A. P. et al., Mol. Cell Proteomics. 12 (2013): 180-193
Bozza, W. P. et al., Oncotarget. 6 (2015): 32723-32736
Braulke, T. et al., Arch. Biochem. Biophys. 298 (1992): 176-181
Braumuller, H. et al., Nature (2013)

Bray, F. et al., Int J Cancer 132 (2013): 1133-1145
Brechmann, M. et al., Immunity. 37 (2012): 697-708
Bredholt, G. et al., Oncotarget. 6 (2015): 39676-39691
Breuninger, S. et al., Am. J Pathol. 176 (2010): 2509-2519
Brezinova, J. et al., Cancer Genet. Cytogenet. 173 (2007): 10-16
Broghammer, M. et al., Cancer Lett. 214 (2004): 225-229
Brossart, P. et al., Blood 90 (1997): 1594-1599
Bruckdorfer, T. et al., Curr. Pharm. Biotechnol. 5 (2004): 29-43
Buckley, N. E. et al., Cell Death. Dis. 5 (2014): e1070
Bui, P. H. et al., Mol. Pharmacol. 76 (2009): 1044-1052
Buim, M. E. et al., Oncology 69 (2005): 445-454
Bujas, T. et al., Eur. J Histochem. 55 (2011): e7
Cai, J. L. et al., Chin J Cancer Res 23 (2011): 59-63
Cai, Q. et al., Nat Genet. 46 (2014): 886-890
Calmon, M. F. et al., Epigenetics. 10 (2015): 622-632
Calvo, N. et al., Biochem. Cell Biol 92 (2014): 305-315
Canet, B. et al., Hum. Pathol. 42 (2011): 833-839
Cao, Z. et al., Mol. Oncol 8 (2014): 285-296
Card, K. F. et al., Cancer Immunol Immunother. 53 (2004): 345-357
Carinci, F. et al., Int. J Immunopathol. Pharmacol. 18 (2005): 513-524
Cazier, J. B. et al., Nat Commun. 5 (2014): 3756
Cetindis, M. et al., Eur. Arch. Otorhinolaryngol. (2015)
Chakrabarti, G. et al., Cancer Metab 3 (2015): 12
Chaneton, B. et al., Trends Biochem. Sci. 37 (2012): 309-316
Chang, I. W. et al., Tumour. Biol 36 (2015): 5441-5450
Chang, J. W. et al., Anticancer Res 32 (2012): 1259-1265
Chanock, S. J. et al., Hum. Immunol. 65 (2004): 1211-1223
Chauvet, C. et al., PLoS. One. 6 (2011): e22545
Che, J. et al., Tumour. Biol 36 (2015): 6559-6568
Chen, B. et al., Mol. Cancer Res 10 (2012): 305-315
Chen, K. D. et al., Cell Death. Dis. 5 (2014a): e1244
Chen, L. et al., Int. J Mol. Sci. 15 (2014b): 11435-11445
Chen, Q. et al., Cell Physiol Biochem. 35 (2015a): 1052-1061
Chen, R. S. et al., Oncogene 28 (2009): 599-609
Chen, S. et al., Cancer Epidemiol. 37 (2013): 172-178
Chen, W. M. et al., Dig. Dis. Sci. 60 (2015b): 1655-1662
Chen, Y. et al., Med. Oncol 31 (2014c): 304
Chen, Y. C. et al., Int. J Cancer 135 (2014d): 117-127
Chen, Z. T. et al., Int. J Mol. Sci. 16 (2015c): 15497-15530
Cheon, D. J. et al., Clin Cancer Res 20 (2014): 711-723
Cheuk, W. et al., Pathology 33 (2001): 7-12
Cho, S. J. et al., PLoS. One. 8 (2013): e71724
Choi, W. I. et al., Cell Physiol Biochem. 23 (2009): 359-370
Chuang, W. Y. et al., Histol. Histopathol. 28 (2013): 293-299
Chung, J. et al., J Cell Biol 158 (2002): 165-174
Chung, T. K. et al., Int. J Cancer 137 (2015): 776-783
Cimino, D. et al., Int. J Cancer 123 (2008): 1327-1338
Cipriano, R. et al., Mol. Cancer Res 12 (2014): 1156-1165
ClinicalTrials.gov, (2015), www.clinicaltrials.gov
Cohen, C. J. et al., J Mol Recognit. 16 (2003a): 324-332
Cohen, C. J. et al., J Immunol 170 (2003b): 4349-4361
Cohen, S. N. et al., Proc. Natl. Acad. Sci. U.S.A 69 (1972): 2110-2114
Coligan, J. E. et al., Current Protocols in Protein Science (1995)
Colombetti, S. et al., J Immunol. 176 (2006): 2730-2738
Council, L. et al., Mod. Pathol. 22 (2009): 639-650
Crossen, P. E. et al., Cancer Genet. Cytogenet. 113 (1999): 126-133
Cui, D. et al., Oncogene 33 (2014): 2225-2235
Daigeler, A. et al., J Exp. Clin Cancer Res 27 (2008): 82
Dang, C. V. et al., Clin Cancer Res 15 (2009): 6479-6483
Dang, Q. et al., Med. Oncol 31 (2014): 24
Dar, A. A. et al., Immunology (2015)
Davids, M. S. et al., Leuk. Lymphoma 53 (2012): 2362-2370
Davidson, B. et al., Hum. Pathol. 45 (2014): 691-700
de Groen, F. L. et al., Genes Chromosomes. Cancer 53 (2014): 339-348
de Jonge, H. J. et al., Leukemia 25 (2011): 1825-1833
de Sa, V. K. et al., Braz. J Med. Biol Res 46 (2013): 21-31
De, Keersmaecker K. et al., Haematologica 99 (2014): 85-93
De, Ponti A. et al., Cancer Lett. 369 (2015): 396-404
Deacu, E. et al., Cancer Res 64 (2004): 7690-7696
Deb, S. et al., Mod. Pathol. 27 (2014): 1223-1230
Debiec-Rychter, M. et al., Genes Chromosomes. Cancer 38 (2003): 187-190
DeLaBarre, B. et al., Chem Biol 21 (2014): 1143-1161
Delker, D. A. et al., PLoS. One. 9 (2014): e88367
Demirag, G. G. et al., Med. Oncol 29 (2012): 1518-1522
Demirci, H. et al., J Ophthalmic Vis. Res 8 (2013): 303-307
Dengjel, J. et al., Clin Cancer Res 12 (2006): 4163-4170
Denkberg, G. et al., J Immunol 171 (2003): 2197-2207
Depianto, D. et al., Nat Genet. 42 (2010): 910-914
Ding, L. et al., Nature 481 (2012): 506-510
Dotlic, S. et al., Appl. Immunohistochem. Mol. Morphol. 22 (2014): 537-542
Downie, D. et al., Clin Cancer Res. 11 (2005): 7369-7375
Draberova, E. et al., J Neuropathol. Exp. Neurol. 74 (2015): 723-742
Drayton, R. M. et al., Clin Cancer Res 20 (2014): 1990-2000
Du, J. et al., Int. J Mol. Sci. 13 (2012): 15755-15766
Duanmin, H. et al., Hepatogastroenterology 60 (2013): 870-875
Dubrowinskaja, N. et al., Cancer Med. 3 (2014): 300-309
Ehrlichova, M. et al., Genomics 102 (2013): 96-101
El-Naggar, A. M. et al., Cancer Cell 27 (2015): 682-697
Espinosa, A. M. et al., PLoS. One. 8 (2013): e55975
Esseghir, S. et al., J Pathol. 210 (2006): 420-430
Falk, K. et al., Nature 351 (1991): 290-296
Fang, J. et al., BMC. Cancer 8 (2008a): 69
Fang, W. et al., J Transl. Med. 6 (2008b): 32
Fejzo, M. S. et al., Int. J Mol. Sci. 14 (2013): 3094-3109
Fellenberg, F. et al., J Invest Dermatol. 122 (2004): 1510-1517
Feng, G. et al., Leuk. Lymphoma 55 (2014): 2699-2705
Ferlay et al., GLOBOCAN 2012 v1.0, Cancer Incidence and Mortality Worldwide: IARC CancerBase No. 11 [Internet], (2013), globocan.iarc.fr
Fong, L. et al., Proc. Natl. Acad. Sci. U.S.A 98 (2001): 8809-8814
Fontaine, J. F. et al., PLoS. One. 4 (2009): e7632
Forsey, R. W. et al., Biotechnol. Lett. 31 (2009): 819-823
Fu, A. et al., Mol. Med. Rep. 11 (2015a): 4727-4733
Fu, Y. et al., Cancer Biol. Ther 5 (2006): 741-744
Fu, Z. C. et al., Med. Sci. Monit. 21 (2015b): 1276-1287
Fujita, A. et al., Genet. Mol. Res 7 (2008): 371-378
Fujita, N. et al., J Biochem. 152 (2012): 407-413
Fujiwara, K. et al., PLoS. One. 9 (2014): e107247
Furukawa, C. et al., Cancer Res 65 (2005): 7102-7110
Gabrilovich, D. I. et al., Nat Med. 2 (1996): 1096-1103
Gao, Y. B. et al., Nat Genet. 46 (2014): 1097-1102
Gattinoni, L. et al., Nat Rev. Immunol 6 (2006): 383-393
Giallourakis, C. C. et al., J Immunol. 190 (2013): 5578-5587
Giovinazzo, F. et al., Cell Signal. 25 (2013): 651-659
Gkika, D. et al., J Cell Biol 208 (2015): 89-107
Gnjatic, S. et al., Proc Natl. Acad. Sci. U.S.A 100 (2003): 8862-8867
Godkin, A. et al., Int. Immunol 9 (1997): 905-911

Goode, G. et al., PLoS. One. 9 (2014): e100103
Gordon, G. J. et al., BMC. Cancer 11 (2011): 169
Gorski, J. J. et al., Breast Cancer Res Treat. 122 (2010): 721-731
Green, M. R. et al., Molecular Cloning, A Laboratory Manual 4th (2012)
Greenfield, E. A., Antibodies: A Laboratory Manual 2nd (2014)
Groulx, J. F. et al., Carcinogenesis 35 (2014): 1217-1227
Guo, X. et al., Sci. Rep. 5 (2015): 11846
Gupta, V. et al., Curr. Pharm. Des 20 (2014): 2595-2606
Nagel, C. et al., J Neurooncol. 112 (2013): 191-197
Haggman, M. J. et al., Urology 50 (1997): 643-647
Hammam, O. et al., J Egypt. Soc. Parasitol. 44 (2014): 733-740
Hapgood, G. et al., Blood 126 (2015): 17-25
Haraguchi, N. et al., Int. J Oncol 43 (2013): 425-430
Harris, T. M. et al., Arch. Pathol. Lab Med. 139 (2015): 494-507
Haslene-Hox, H. et al., Biochim. Biophys. Acta 1834 (2013): 2347-2359
Hatina, J. et al., Neoplasma 59 (2012): 728-736
Hauser, A. D. et al., Mol. Cancer Res 12 (2014): 130-142
He, X. et al., Int. J Biol Macromol. 72 (2015): 1081-1089
Heffler, M. et al., Anticancer Agents Med. Chem 13 (2013): 584-594
Heubeck, B. et al., Eur. J Cancer 49 (2013): e1-e7
Hoeflich, K. P. et al., Int. J Oncol 29 (2006): 839-849
Hofsli, E. et al., Br. J Cancer 99 (2008): 1330-1339
Hogan, L. E. et al., Blood 118 (2011): 5218-5226
Hountis, P. et al., Tumour. Biol 35 (2014): 7327-7333
Hu, C. K. et al., Mol. Biol Cell 23 (2012): 2702-2711
Huang, F. et al., Int. J Clin Exp. Pathol. 7 (2014a): 1093-1100
Huang, S. L. et al., Cancers (Basel) 7 (2015): 1052-1071
Huang, Y. D. et al., Hua Xi. Kou Qiang. Yi. Xue. Za Zhi. 25 (2007): 500-503
Huang, Z. et al., Indian J Otolaryngol. Head Neck Surg. 66 (2014b): 120-125
Huang, Z. et al., J Oral Pathol. Med. 43 (2014c): 191-198
Hussey, G. S. et al., Mol Cell 41 (2011): 419-431
Hwang, M. L. et al., J Immunol. 179 (2007): 5829-5838
Ichinose, J. et al., Cancer Sci. 105 (2014): 1135-1141
Ida-Yonemochi, H. et al., Mod. Pathol. 25 (2012): 784-794
Ii, M. et al., Int. J Oncol 39 (2011): 593-599
Inoue, H. et al., Int. J Cancer 63 (1995): 523-526
Inoue, K. et al., Subcell. Biochem. 85 (2014): 17-40
Iqbal, M. A. et al., FEBS Lett. 588 (2014): 2685-2692
Irifune, H. et al., Cancer Biol Ther. 4 (2005): 449-455
Ismail, M. F. et al., Tumour. Biol (2015)
Israelsen, W. J. et al., Semin. Cell Dev. Biol 43 (2015): 43-51
Jamieson, N. B. et al., Clin Cancer Res 17 (2011): 3316-3331
Januchowski, R. et al., Biomed. Pharmacother. 67 (2013): 240-245
Jiang, L. et al., Cell Cycle 14 (2015): 2881-2885
Jin, J. et al., Int. J Hematol. 99 (2014): 750-757
Johnson, R. H. et al., Oncotarget. (2015)
Johnstone, C. N. et al., Dis. Model. Mech. 8 (2015): 237-251
Joosse, S. A. et al., Clin Cancer Res 18 (2012): 993-1003
Jung, G. et al., Proc Natl Acad Sci USA 84 (1987): 4611-4615
Kabbage, M. et al., J Biomed. Biotechnol. 2008 (2008): 564127
Kanehira, M. et al., Cancer Res 67 (2007): 3276-3285
Kang, S. et al., J Proteome. Res 9 (2010): 5638-5645
Kao, C. J. et al., Oncogene 27 (2008): 1397-1403
Karlsson, J. et al., Cancer Lett. 357 (2015): 498-501
Kato, I. et al., Pathol. Int. 59 (2009): 38-43
Katoh, M., Int. J Oncol 41 (2012): 1913-1918
Kaz, A. M. et al., Genes Chromosomes. Cancer 51 (2012): 384-393
Kazma, R. et al., PLoS. One. 7 (2012): e51680
Kerley-Hamilton, J. S. et al., Oncogene 24 (2005): 6090-6100
Khakpour, G. et al., Tumour. Biol 36 (2015): 4905-4912
Khalil, A. A., Cancer Sci. 98 (2007): 201-213
Khapare, N. et al., PLoS. One. 7 (2012): e38561
Kibbe, A. H., Handbook of Pharmaceutical Excipients rd (2000)
Kido, T. et al., Genes (Basel) 1 (2010): 283-293
Kim, S. W. et al., OMICS. 15 (2011): 281-292
Kimura, H. et al., Int. J Oncol 30 (2007): 171-179
Kinoshita, T. et al., Oncotarget. 3 (2012): 1386-1400
Kirov, A. et al., J Cell Biochem. (2015)
Kita, Y. et al., Eur. J Surg. Oncol 35 (2009): 52-58
Klopfleisch, R. et al., J Proteome. Res 9 (2010): 6380-6391
Koizume, S. et al., Cancer Res 66 (2006): 9453-9460
Koizume, S. et al., World J Clin Oncol 5 (2014): 908-920
Koizume, S. et al., Biomark. Cancer 7 (2015): 1-13
Kono, K. et al., Cancer Sci. 100 (2009): 1502-1509
Kottorou, A. E. et al., Acta Histochem. 114 (2012): 553-561
Krieg, A. M., Nat Rev. Drug Discov. 5 (2006): 471-484
Krisenko, M. O. et al., Biochim. Biophys. Acta 1853 (2015): 254-263
Kruse, A. J. et al., Int. J Gynecol. Cancer 24 (2014): 1616-1622
Kulkarni, G. et al., Breast Cancer Res Treat. 102 (2007): 31-41
Kultti, A. et al., Biomed. Res Int. 2014 (2014): 817613
Kumar, M. et al., J Transl. Med. 13 (2015): 8
Kumarakulasingham, M. et al., Clin Cancer Res 11 (2005): 3758-3765
Kuramitsu, Y. et al., Anticancer Res 30 (2010): 4459-4465
Kurimoto, F. et al., Int. J Mol. Med. 8 (2001): 89-93
Kwon, 0. H. et al., Biochem. Biophys. Res Commun. 406 (2011): 539-545
Larrinaga, G. et al., Dis. Markers 35 (2013): 825-832
Lauvrak, S. U. et al., Br. J Cancer 109 (2013): 2228-2236
Leal, M. F. et al., World J Gastroenterol. 18 (2012): 1531-1537
Ledet, E. M. et al., Prostate 73 (2013): 614-623
Lee, E. J. et al., J Genet. Genomics 42 (2015a): 355-371
Lee, H. W. et al., Dis. Esophagus. (2015b)
Lee, J. et al., Oncoscience. 2 (2015c): 410-418
Lee, J. M., Reprod. Biol Endocrinol. 1 (2003): 69
Lee, M. H. et al., J Cell Sci. 126 (2013): 1744-1752
Lee, M. H. et al., Ann. N.Y. Acad. Sci. 1171 (2009): 87-93
Lee, S. H. et al., EMBO J 25 (2006): 4008-4019
Lee, S. Y. et al., J Clin Invest 122 (2012): 3211-3220
Lei, Y. Y. et al., Asian Pac. J Cancer Prev. 15 (2014): 8539-8548
Leithner, K. et al., BMC. Cancer 14 (2014): 40
Leitlinie Magenkarzinom, 032-0090L, (2012)
Lexander, H. et al., Anal. Quant. Cytol. Histol. 27 (2005): 263-272
Li, C. et al., Oncogene 23 (2004): 9336-9347
Li, C. et al., Am. J Cancer Res 5 (2015a): 1635-1648
Li, R. et al., Oncogene 25 (2006): 2628-2635
Li, X. et al., Pancreas 40 (2011): 753-761
Li, X. Q. et al., PLoS. One. 7 (2012): e31146
Li, Y. et al., Neoplasia. 7 (2005): 1073-1080
Li, Y. et al., Cell Rep. 12 (2015b): 388-395
Li, Y. et al., Lung Cancer 58 (2007): 171-183

Li, Z. et al., Biochim. Biophys. Acta 1846 (2014): 285-296
Liang, B. et al., World J Gastroenterol. 11 (2005a): 623-628
Liang, J. et al., Tumour. Biol 36 (2015): 6391-6399
Liang, L. et al., Int. J Oncol 45 (2014): 659-666
Liang, Z. et al., Zhonghua Zhong. Liu Za Zhi. 27 (2005b): 534-537
Liao, J. S. et al., Zhejiang. Da. Xue. Xue. Bao. Yi. Xue. Ban. 44 (2015a): 329-334
Liao, W. et al., Oncotarget. 6 (2015b): 24132-24147
Liddy, N. et al., Nat Med. 18 (2012): 980-987
Lim, M. Y. et al., Int. J Chronic. Dis. 2013 (2013): 578613
Lim, R. et al., Biochem. Biophys. Res Commun. 406 (2011): 408-413
Lin, C. et al., Oncotarget. 6 (2015): 8434-8453
Lin, S. J. et al., J Proteomics. 94 (2013): 186-201
Lin, X. et al., Med. Oncol 31 (2014): 42
Linher-Melville, K. et al., Mol. Cell Biochem. 405 (2015): 205-221
Liu, B. et al., J Clin Endocrinol. Metab 99 (2014a): E786-E795
Liu, C. et al., Int. J Clin Exp. Pathol. 7 (2014b): 690-698
Liu, D. et al., Genet. Mol. Res 13 (2014c): 8153-8162
Liu, J. P. et al., Zhonghua Yi. Xue. Za Zhi. 87 (2007a): 2719-2723
Liu, L. et al., Oncol Lett. 7 (2014d): 2192-2198
Liu, Y. et al., J Neurooncol. 99 (2010): 13-24
Liu, Y. et al., Cell Death. Dis. 6 (2015): e1630
Liu, Y. et al., Oncol Rep. 18 (2007b): 943-951
Liu, Y. F. et al., Tumour. Biol 35 (2014e): 3731-3741
Ljunggren, H. G. et al., J Exp. Med. 162 (1985): 1745-1759
Lo, P. K. et al., Oncogene 31 (2012): 2614-2626
Lo, R. K. et al., J Biol Chem 278 (2003): 52154-52165
Lo, W. Y. et al., J Proteome. Res 6 (2007): 2143-2151
Lohr, J. G. et al., Cancer Cell 25 (2014): 91-101
Long, W. et al., J Clin Invest 122 (2012): 1869-1880
Longenecker, B. M. et al., Ann N.Y. Acad. Sci. 690 (1993): 276-291
Longerich, T., Pathologe 35 Suppl 2 (2014): 177-184
Lonsdale, J., Nat. Genet. 45 (2013): 580-585
Lou, S. et al., Stem Cells 31 (2013): 1942-1953
Lu, Z. et al., Cell Physiol Biochem. 33 (2014): 859-868
Lukas, T. J. et al., Proc. Natl. Acad. Sci. U.S.A 78 (1981): 2791-2795
Lundblad, R. L., Chemical Reagents for Protein Modification 3rd (2004)
Luo, W. et al., Trends Endocrinol. Metab 23 (2012): 560-566
Lv, Z. et al., J Exp. Clin Cancer Res 33 (2014): 100
Ma, Y. et al., Mol. Cell Proteomics. 8 (2009): 1878-1890
Madanayake, T. W. et al., BMC. Genomics 14 (2013): 833
Maiso, P. et al., Cancer Res 75 (2015): 2071-2082
Manenti, G. et al., Toxicol. Lett. 112-113 (2000): 257-263
Mao, P. et al., J Biol Chem 286 (2011): 19381-19391
Mao, P. et al., PLoS. One. 8 (2013): e81803
Marcinkiewicz, K. M. et al., Exp. Cell Res 320 (2014): 128-143
Marg, A. et al., Biochem. Biophys. Res Commun. 401 (2010): 143-148
Marhold, M. et al., Mol. Cancer Res 13 (2015): 556-564
Martin-Rufian, M. et al., J Mol. Med. (Berl) 92 (2014): 277-290
Matassa, D. S. et al., Cell Death. Dis. 4 (2013): e851
Mayas, M. D. et al., Anticancer Res 32 (2012): 3675-3682
Mazan-Mamczarz, K. et al., PLoS. Genet. 10 (2014): e1004105
Mazurek, S., Ernst. Schering. Found. Symp. Proc. (2007): 99-124
Mazurek, S., Int. J Biochem. Cell Biol 43 (2011): 969-980
McBride, D. J. et al., J Pathol. 227 (2012): 446-455
Melaiu, O. et al., Mutat. Res 771 (2015): 6-12
Messina, M. et al., Blood 123 (2014): 2378-2388
Meziere, C. et al., J Immunol 159 (1997): 3230-3237
Mimori, K. et al., Int. J Oncol 11 (1997): 959-964
Mirza, Z. et al., Anticancer Res 34 (2014): 1873-1884
Missero, C. et al., Exp. Dermatol. 23 (2014): 143-146
Moretti, R. M. et al., Oncol Rep. 9 (2002): 1139-1143
Morgan, R. A. et al., Science 314 (2006): 126-129
Mori, M. et al., Transplantation 64 (1997): 1017-1027
Morris, L. G. et al., Nat Genet. 45 (2013): 253-261
Mortara, L. et al., Clin Cancer Res. 12 (2006): 3435-3443
Mountzios, G. et al., Ann. Oncol 25 (2014): 1889-1900
Mueller, L. N. et al., J Proteome. Res 7 (2008): 51-61
Mueller, L. N. et al., Proteomics. 7 (2007): 3470-3480
Mumberg, D. et al., Proc. Natl. Acad. Sci. U.S.A 96 (1999): 8633-8638
Murray, G. I. et al., Histopathology 57 (2010): 202-211
Mustacchi, G. et al., Int. J Mol. Sci. 14 (2013): 9686-9702
Naba, A. et al., Elife. 3 (2014): e01308
Naboulsi, W. et al., J Proteome. Res (2015)
Naderi, A., Exp. Cell Res 331 (2015): 239-250
Nakao, K. et al., J Gastroenterol. 49 (2014): 589-593
Navara, C. S., Curr. Pharm. Des 10 (2004): 1739-1744
Naz, S. et al., Carcinogenesis 35 (2014): 14-23
Neumann, M. et al., Blood 121 (2013): 4749-4752
Ng, S. K. et al., Clin Experiment. Ophthalmol. 43 (2015): 367-376
Nikitakis, N. G. et al., Am. J Clin Pathol. 119 (2003): 574-586
Nishida, C. R. et al., Mol. Pharmacol. 78 (2010): 497-502
Nwosu, V. et al., Hum. Mol Genet. 10 (2001): 2313-2318
Nykopp, T. K. et al., BMC. Cancer 10 (2010): 512
O'Gorman, D. B. et al., Endocrinology 143 (2002): 4287-4294
Oh, H. R. et al., Cell Oncol (Dordr.) 37 (2014): 455-461
Ohigashi, Y. et al., Clin Cancer Res. 11 (2005): 2947-2953
Okayama, H. et al., Cancer Epidemiol. Biomarkers Prev. 23 (2014): 2884-2894
Okoh, V. O. et al., PLoS. One. 8 (2013): e54206
Olstad, O. K. et al., Anticancer Res 23 (2003): 2201-2216
Ordonez, N. G., Arch. Pathol. Lab Med. 129 (2005): 1407-1414
Orzol, P. et al., Histol. Histopathol. 30 (2015): 503-521
Padden, J. et al., Mol. Cell Proteomics. 13 (2014): 2661-2672
Pan, B. et al., Mol. Biol Rep. 40 (2013): 27-33
Pan, T. et al., Biochem. Biophys. Res Commun. 456 (2015): 452-458
Papagerakis, S. et al., Hum. Pathol. 34 (2003): 565-572
Park, Y. et al., Oncogene 34 (2015): 5037-5045
Parker, L. P. et al., Cancer Genomics Proteomics. 6 (2009): 189-194
Pathak, S. et al., Nutr. Cancer 66 (2014): 818-824
Peng, H. et al., Cell Oncol (Dordr.) 38 (2015): 165-172
Penney, K. L. et al., Cancer Epidemiol. Biomarkers Prev. 24 (2015): 255-260
Perez, I. et al., Int. J Med. Sci. 12 (2015): 458-467
Persson, F. et al., Cancer Lett. 260 (2008): 37-47
Pflueger, D. et al., Neoplasia. 15 (2013): 1231-1240
Pickering, C. R. et al., Clin Cancer Res 20 (2014): 6582-6592
Pillay, V. et al., S. Afr. Med. J 105 (2015): 656-658
Pils, D. et al., BMC. Cancer 13 (2013): 178
Pinheiro, J. et al., nlme: Linear and Nonlinear Mixed Effects Models (CRAN.R-project.org/packe=nlme) (2015)
Plebanski, M. et al., Eur. J Immunol 25 (1995): 1783-1787

Porta, C. et al., Virology 202 (1994): 949-955
Prasad, N. B. et al., Mod. Pathol. 27 (2014): 945-957
Puente, X. S. et al., Nature 526 (2015): 519-524
Qendro, V. et al., J Proteome. Res 13 (2014): 5031-5040
Qi, Y. et al., Proteomics. 5 (2005): 2960-2971
Qi, Y. et al., J Breast Cancer 18 (2015): 218-224
Qie, S. et al., J Cell Biochem. 115 (2014): 498-509
Qu, Y. M. et al., Zhonghua Yi. Xue. Za Zhi. 90 (2010): 1958-1962
Qu, Z. et al., Cancer Med. 3 (2014): 453-461
Quillien, V. et al., Anticancer Res. 17 (1997): 387-391
Rabinovitz, I. et al., Biochem. Cell Biol 74 (1996): 811-821
Rabinovitz, I. et al., Clin Exp. Metastasis 13 (1995): 481-491
Rad, E. et al., Mol. Cancer Res 13 (2015): 1149-1160
Rai, R. et al., Oral Oncol 40 (2004): 705-712
Raica, M. et al., Anticancer Res 28 (2008): 2997-3006
Ramirez-Exposito, M. J. et al., Maturitas 72 (2012): 79-83
Rammensee, H. G. et al., Immunogenetics 50 (1999): 213-219
Reeb, A. N. et al., J Clin Endocrinol. Metab 100 (2015): E232-E242
RefSeq, The NCBI handbook [Internet], Chapter 18, (2002), www.ncbi.nlm.nih.gov/books/NBK21091/
Rehman, I. et al., PLoS. One. 7 (2012): e30885
Reis, S. T. et al., Clinics. (Sao Paulo) 68 (2013): 652-657
Remmelink, M. et al., Int. J Oncol 26 (2005): 247-258
Revill, K. et al., Gastroenterology 145 (2013): 1424-1435
Ricketts, C. J. et al., Clin Epigenetics. 5 (2013): 16
Rini, B. I. et al., Cancer 107 (2006): 67-74
Rock, K. L. et al., Science 249 (1990): 918-921
Rodenko, B. et al., Nat Protoc. 1 (2006): 1120-1132
Roemer, A. et al., J Urol. 172 (2004): 2162-2166
Romana, S. P. et al., Leukemia 20 (2006): 696-706
Rozenblum, E. et al., Hum. Genet. 110 (2002): 111-121
Ruminy, P. et al., Leukemia 25 (2011): 681-688
Safadi, R. A. et al., Oral Surg. Oral Med. Oral Pathol. Oral Radiol. 121 (2016): 402-411
Saiki, R. K. et al., Science 239 (1988): 487-491
Sanchez-Palencia, A. et al., Int. J Cancer 129 (2011): 355-364
Santarpia, L. et al., Oncologist. 18 (2013): 1063-1073
Sarma, S. N. et al., Environ. Toxicol. Pharmacol. 32 (2011): 285-295
Sathyanarayana, U. G. et al., Cancer Res 64 (2004): 1425-1430
Sato, T. et al., Oncogene 33 (2014): 2215-2224
Sato, Y. et al., J Gastroenterol. Hepatol. 28 (2013): 1422-1429
Savaskan, N. E. et al., Ann. Anat. 192 (2010): 309-313
Savaskan, N. E. et al., Curr. Neuropharmacol. 13 (2015): 258-265
Savoy, R. M. et al., Endocr. Relat Cancer 20 (2013): R341-R356
Schlieben, P. et al., Vet. J 194 (2012): 210-214
Schmitt-Graeff, A. et al., Histopathology 51 (2007): 87-97
Schuld, N. J. et al., Cell Cycle 13 (2014): 941-952
Schumann, H. et al., Br. J Dermatol. 167 (2012): 929-936
Scrideli, C. A. et al., J Neurooncol. 88 (2008): 281-291
Seda, V. et al., Eur. J Haematol. 94 (2015): 193-205
Seeger, F. H. et al., Immunogenetics 49 (1999): 571-576
Seitz, S. et al., Eur. J Cancer 36 (2000): 1507-1513
Semenza, G. L., Cold Spring Harb. Symp. Quant. Biol 76 (2011): 347-353
Seong, J. et al., Mol. Biol. Rep. 39 (2012): 3597-3601
Sethi, M. K. et al., J Proteomics. 126 (2015): 54-67
Sherman, F. et al., Laboratory Course Manual for Methods in Yeast Genetics (1986)
Shi, Z. et al., Int. J Gynecol. Cancer 22 (2012): 1125-1129
Shi, Z. G. et al., Clin Transl. Oncol 17 (2015): 65-73
Shibano, T. et al., PLoS. One. 10 (2015): e0127271
Shin, S. H. et al., Lab Invest 94 (2014): 1396-1405
Shruthi, D. K. et al., J Oral Maxillofac. Pathol. 18 (2014): 365-371
Silva, J. M. et al., Cell 137 (2009): 1047-1061
Silva, L. P. et al., Anal. Chem. 85 (2013): 9536-9542
Singh, V. et al., OMICS. 19 (2015): 688-699
Singh-Jasuja, H. et al., Cancer Immunol. Immunother. 53 (2004): 187-195
Slaga, T. J. et al., J Investig. Dermatol. Symp. Proc. 1 (1996): 151-156
Small, E. J. et al., J Clin Oncol. 24 (2006): 3089-3094
Sobolik-Delmaire, T. et al., Cell Commun. Adhes. 14 (2007): 99-109
Spurr, I. B. et al., Chembiochem. 13 (2012): 1628-1634
Stahl, M. et al., Ann. Oncol. 24 Suppl 6 (2013): vi51-vi56
Stull, R. A. et al., BMC. Genomics 6 (2005): 55
Sturm, M. et al., BMC. Bioinformatics. 9 (2008): 163
Sugimoto, K. J. et al., Int. J Clin Exp. Pathol. 7 (2014): 8980-8987
Suh, J. H. et al., J Korean Med. Sci. 28 (2013): 593-601
Sun, M. et al., Biochem. Biophys. Res Commun. 340 (2006): 209-214
Sun, Y. et al., Biochem. Biophys. Res Commun. 450 (2014): 1-6
Suzuki, S. et al., Pathol. Res Pract. 210 (2014): 130-134
Swain, N. et al., Tumour. Biol 35 (2014): 8407-8413
Szeliga, M. et al., Tumour. Biol 35 (2014): 1855-1862
Takabe, P. et al., Exp. Cell Res 337 (2015): 1-15
Takahashi, H. et al., Urology 79 (2012): 240-248
Takeda, H. et al., Nat Genet. 47 (2015): 142-150
Tamada, M. et al., Clin Cancer Res 18 (2012): 5554-5561
Tan, B. S. et al., Mol. Cancer Ther. 10 (2011): 1982-1992
Tanaka, F. et al., Int. J Oncol 10 (1997): 1113-1117
Tang, H. et al., Anticancer Drugs 18 (2007): 633-639
Tang, H. et al., Clin Cancer Res 19 (2013): 1577-1586
Tang, J. Q. et al., Beijing Da. Xue. Xue. Bao. 41 (2009): 531-536
Tang, J. Q. et al., Chin Med. J (Engl.) 123 (2010): 3559-3565
Tanis, T. et al., Arch. Oral Biol 59 (2014): 1155-1163
Tech, K. et al., Cancer Lett. 356 (2015): 268-272
Teng, B. P. et al., Anticancer Agents Med. Chem 11 (2011): 620-628
Terada, T., Int. J Clin Exp. Pathol. 5 (2012): 596-600
Teufel, R. et al., Cell Mol Life Sci. 62 (2005): 1755-1762
Tew, G. W. et al., J Biol Chem 283 (2008): 963-976
Thomas, A. et al., Cancer Med. 2 (2013): 836-848
Tian, S. Y. et al., Int. J Clin Exp. Pathol. 7 (2014): 3752-3762
Tofuku, K. et al., Int. J Oncol 29 (2006): 175-183
Toh, U. et al., Int. J Clin Oncol 7 (2002): 372-375
Toh, U. et al., Clin Cancer Res. 6 (2000): 4663-4673
Toomey, P. G. et al., Cancer Control 20 (2013): 32-42
Tota, G. et al., BMC. Cancer 14 (2014): 963
Tran, E. et al., Science 344 (2014): 641-645
Truong, T. et al., Endocr. Relat Cancer 21 (2014): 629-638
Tsujimoto, H. et al., Mol. Carcinog 26 (1999): 298-304
Tuupanen, S. et al., Br. J Cancer 111 (2014): 1657-1662
Tuval-Kochen, L. et al., PLoS. One. 8 (2013): e77260
Twa, D. D. et al., J Pathol. 236 (2015): 136-141
Twarock, S. et al., Mol. Cancer 10 (2011): 30
Tzellos, T. G. et al., J Eur. Acad. Dermatol. Venereol. 25 (2011): 679-687
Urosevic, J. et al., Nat Cell Biol 16 (2014): 685-694

Vachani, A. et al., Clin Cancer Res. 13 (2007): 2905-2915
Valladares-Ayerbes, M. et al., Cancer Epidemiol. Biomarkers Prev. 19 (2010): 1432-1440
Valletta, D. et al., Carcinogenesis 35 (2014): 1407-1415
van, Geldermalsen M. et al., Oncogene (2015)
Varga, A. E. et al., Oncogene 24 (2005): 5043-5052
Varona, A. et al., Am. J Physiol Renal Physiol 292 (2007): F780-F788
Vasca, V. et al., Oncol Lett. 8 (2014): 2501-2504
Venneti, S. et al., Brain Pathol. 23 (2013): 217-221
Virtakoivu, R. et al., Cancer Res 75 (2015): 2349-2362
Volkmer, J. P. et al., Proc. Natl. Acad. Sci. U.S.A 109 (2012): 2078-2083
Volpi, A. et al., G. Chir 32 (2011): 59-63
Vui-Kee, K. et al., Kaohsiung. J Med. Sci. 28 (2012): 243-250
Walter, S. et al., J Immunol 171 (2003): 4974-4978
Walter, S. et al., Nat Med. 18 (2012): 1254-1261
Wang, D. et al., Biochem. Biophys. Res Commun. 458 (2015a): 313-320
Wang, H. et al., Front Oncol 4 (2014): 377
Wang, H. et al., Cancer Cell 18 (2010): 52-62
Wang, J. et al., Oncol Rep. 33 (2015b): 1326-1334
Wang, T. et al., Tumour. Biol (2015c)
Wang, W. M. et al., J Biol Chem 278 (2003): 19549-19557
Wang, X. et al., Eur. J Pharmacol. 768 (2015d): 116-122
Wang, X. M. et al., PLoS. One. 8 (2013a): e55714
Wang, X. Y. et al., Int J Hyperthermia 29 (2013): 364-375
Wang, Y. et al., Neoplasma 62 (2015e): 966-973
Wang, Z. et al., Oncotarget. 4 (2013b): 2476-2486
Wang, Z. et al., Melanoma Res 14 (2004): 107-114
Warner, S. L. et al., Future. Med. Chem 6 (2014): 1167-1178
Watanabe, Y. et al., Gastroenterology 136 (2009): 2149-2158
Wegdam, W. et al., PLoS. One. 9 (2014): e108046
Wehner, M. et al., FEBS J 277 (2010): 1597-1605
Weiss, I. et al., Int. J Mol. Sci. 13 (2012): 12925-12938
Weissbach, S. et al., Br. J Haematol. 169 (2015): 57-70
Wiedl, T. et al., J Proteomics. 74 (2011): 1884-1894
Willcox, B. E. et al., Protein Sci. 8 (1999): 2418-2423
Willoughby, V. et al., Appl. Immunohistochem. Mol. Morphol. 16 (2008): 344-348
Wittke, I. et al., Cancer Lett. 162 (2001): 237-243
Wojtalewicz, N. et al., PLoS. One. 9 (2014): e90461
Wong, N. et al., Cancer Lett. 356 (2015): 184-191
Woo, T. et al., PLoS. One. 10 (2015): e0142642
World Cancer Report, (2014)
Wu, G. et al., Onco. Targets. Ther. 8 (2015): 2067-2074
Wu, S. et al., Acta Biochim. Biophys. Sin. (Shanghai) 45 (2013): 27-35
Wu, X. et al., Cancer Res 70 (2010): 2718-2727
Xiang, Y. et al., J Clin Invest 125 (2015): 2293-2306
Xu, J. et al., Genet. Mol. Res 13 (2014): 5732-5744
Xu, X. et al., Oncotarget. 6 (2015): 26161-26176
Xue, L. Y. et al., Zhonghua Zhong. Liu Za Zhi. 32 (2010): 838-844
Yager, M. L. et al., Br. J Cancer 89 (2003): 860-863
Yamaguchi, T. et al., Dis. Colon Rectum 49 (2006): 399-406
Yamamoto, M. et al., PLoS. One. 6 (2011): e17149
Yamamoto, N. et al., Int. J Oncol 42 (2013): 1523-1532
Yang, C. et al., Tumour. Biol (2015a)
Yang, C. et al., Exp. Cell Res 331 (2015b): 377-386
Yang, H. Y. et al., J Proteomics. 75 (2012): 3639-3653
Yang, J. Y. et al., BMC. Cancer 10 (2010): 388
Yang, S. et al., J Cancer Res Clin Oncol 141 (2015c): 1265-1275
Yang, W. et al., Cancer Lett. 339 (2013): 153-158
Yang, W. et al., Nature 499 (2013a): 491-495
Yang, W. et al., Int. J Oncol 42 (2013b): 690-698
Yao, M. et al., Cancer Med. 3 (2014): 845-854
Yao, R. et al., Histol. Histopathol. 22 (2007): 1025-1032
Yu, D. et al., Oncotarget. 6 (2015a): 7619-7631
Yu, X. et al., Cancer Res 73 (2013): 2093-2103
Yu, Y. et al., Cancer Cell 28 (2015b): 82-96
Yuan, B. et al., Immunobiology 217 (2012): 738-742
Zang, W. et al., Mol. Cancer 14 (2015): 37
Zanini, S. et al., Cell Signal. 27 (2015): 899-907
Zare, M. et al., Mol. Carcinog 51 (2012): 796-806
Zaremba, S. et al., Cancer Res. 57 (1997): 4570-4577
Zha, C. et al., PLoS. One. 10 (2015): e0122322
Zhang, D. et al., J Cell Mol. Med. 16 (2012): 1047-1059
Zhang, H. Y. et al., Mol. Biol Rep. 41 (2014): 5519-5524
Zhang, Q. et al., J Cancer Res Clin Oncol 141 (2015a): 691-703
Zhang, S. et al., Cancer Res 64 (2004): 2977-2983
Zhang, S. et al., J Mol. Histol. 45 (2014): 283-292
Zhang, S. N. et al., Zhonghua Yi. Xue. Za Zhi. 85 (2005): 1348-1351
Zhang, T. et al., Mol. Cancer 9 (2010): 72
Zhang, X. et al., Int. J Cancer 137 (2015b): 2803-2814
Zhang, X. et al., Tumour. Biol 36 (2015c): 5979-5985
Zhang, X. et al., PLoS. One. 8 (2013): e72458
Zhang, Y. et al., Cancer Metastasis Rev 34 (2015d): 249-264
Zhang, Z. Z. et al., Mol. Cancer Ther. 14 (2015e): 1162-1170
Zhao, D. et al., J Neurooncol. 118 (2014a): 39-47
Zhao, G. et al., Biochem. Biophys. Res Commun. 408 (2011): 154-159
Zhao, H. et al., Gene 548 (2014b): 234-243
Zhao, L. J. et al., Chin Med. J (Engl.) 126 (2013): 4260-4264
Zheng, Q. et al., Tumour. Biol 35 (2014): 6255-6264
Zheng, R. et al., Int. Immunopharmacol. 29 (2015): 919-925
Zhi, H. et al., J Pathol. 217 (2009): 389-397
Zhou, Y. F. et al., World J Gastroenterol. 20 (2014): 13172-13177
Zhu, H. et al., Cancer Lett. 245 (2007a): 303-314
Zhu, L. et al., J Dermatol. Sci. 72 (2013a): 311-319
Zhu, S. et al., J Biol Chem 282 (2007b): 14328-14336
Zhu, Y. et al., Prostate 73 (2013b): 1614-1622
Zhu, Y. P. et al., Oncotarget. 6 (2015): 14488-14496

The invention claimed is:

1. A method of treating a patient who has a cancer overexpressing KRT5 polypeptide comprising the amino acid sequence of SEQ ID NO: 2, comprising administering to said patient a composition comprising a population of activated T cells that kill the cancer cells,
   wherein the activated T cells are cytotoxic T cells produced by contacting T cells with an antigen presenting cell that presents a peptide consisting of the amino acid sequence of SEQ ID NO: 2 in a complex with an MHC class I molecule on the surface of the antigen presenting cell in vitro, for a period of time sufficient to activate said T cell,
   wherein said cancer is selected from the group consisting of esophageal cancer, lung cancer, urinary bladder cancer, head and neck cancer, and gastric cancer.

2. The method of claim 1, wherein the T cells are autologous to the patient.

3. The method of claim 1, wherein the T cells are obtained from a healthy donor.

4. The method of claim 1, wherein the T cells are derived from tumor infiltrating lymphocytes or peripheral blood mononuclear cells.

5. The method of claim 1, further comprising expanding T cells in vitro.

6. The method of claim 5, wherein the expansion is in the presence of an anti-CD28 antibody and IL-12.

7. The method of claim 1, wherein the composition further comprises an adjuvant.

8. The method of claim 7, wherein the adjuvant is selected from the group consisting of anti-CD40 antibody, imiquimod, resiquimod, GM-CSF, cyclophosphamide, sunitinib, bevacizumab, interferon-alpha, interferon-beta, CpG, oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

9. The method of claim 7, wherein the adjuvant comprises IL-21.

10. The method of claim 7, wherein the adjuvant comprises IL-7.

11. The method of claim 7, wherein the adjuvant comprises IL-15.

12. The method of claim 1, wherein the antigen presenting cell is infected with a recombinant virus expressing the peptide.

13. The method of claim 12, wherein the antigen presenting cell is a dendritic cell or a macrophage.

14. The method of claim 1, wherein the population of activated T cells comprises CD8-positive cells.

15. The method of claim 1, wherein the MHC class I molecule comprises HLA-A*02:01.

16. The method of claim 1, wherein the cancer is esophageal cancer.

17. The method of claim 1, wherein the cancer is lung cancer.

18. The method of claim 1, wherein the cancer is urinary bladder cancer.

19. The method of claim 1, wherein the cancer is head and neck cancer.

20. The method of claim 1, wherein the cancer is gastric cancer.

* * * * *